US006859275B2

(12) United States Patent
Fateley et al.

(10) Patent No.: US 6,859,275 B2
(45) Date of Patent: Feb. 22, 2005

(54) SYSTEM AND METHOD FOR ENCODED SPATIO-SPECTRAL INFORMATION PROCESSING

(75) Inventors: William G. Fateley, Manhattan, KS (US); Ronald R. Coifman, North Haven, CT (US); Frank Geshwind, Madison, CT (US); Richard A. DeVerse, Kailua-Kona, HI (US)

(73) Assignee: Plain Sight Systems, Inc., Hamden, CT (US)

( * ) Notice: Subject to any disclaimer, the term of this patent is extended or adjusted under 35 U.S.C. 154(b) by 0 days.

(21) Appl. No.: 09/798,860

(22) Filed: Mar. 1, 2001

(65) Prior Publication Data

US 2002/0057431 A1 May 16, 2002

Related U.S. Application Data

(63) Continuation-in-part of application No. 09/672,257, filed on Sep. 28, 2000, now Pat. No. 6,392,748, which is a continuation of application No. 09/502,758, filed on Feb. 11, 2000, now Pat. No. 6,128,078, which is a continuation of application No. 09/289,482, filed on Apr. 9, 1999, now Pat. No. 6,046,808.

(51) Int. Cl.[7] ............................... G01J 3/02; G01J 3/04
(52) U.S. Cl. ........................ 356/330; 356/328; 356/310
(58) Field of Search ................................. 356/310, 330

(56) References Cited

U.S. PATENT DOCUMENTS

| 4,193,691 A | * | 3/1980 | Fjarlie ...................... 356/330 |
| 5,567,937 A | | 10/1996 | Pinkus |
| 6,373,568 B1 | | 4/2002 | Miller et al. |

FOREIGN PATENT DOCUMENTS

| EP | 0916981 A1 | * | 5/1999 |
| WO | WO-98/35211 | * | 8/1998 |

* cited by examiner

*Primary Examiner*—F. L. Evans
(74) *Attorney, Agent, or Firm*—Jones Day

(57) ABSTRACT

Encoded spatio-spectral information processing is performed using a system having a radiation source, wavelength dispersion device and two-dimensional switching array, such as digital micro-mirror array (DMA). In one aspect, spectral components from a sample are dispersed in space and modulated separately by the switching array, each element of which may operate according to a predetermined encoding pattern. The encoded spectral components can then be detected and analyzed. In a different aspect, the switching array can be used to provide a controllable radiation source for illuminating a sample with radiation patterns that have predetermined characteristics and separately encoded components. Various applications are disclosed.

14 Claims, 57 Drawing Sheets

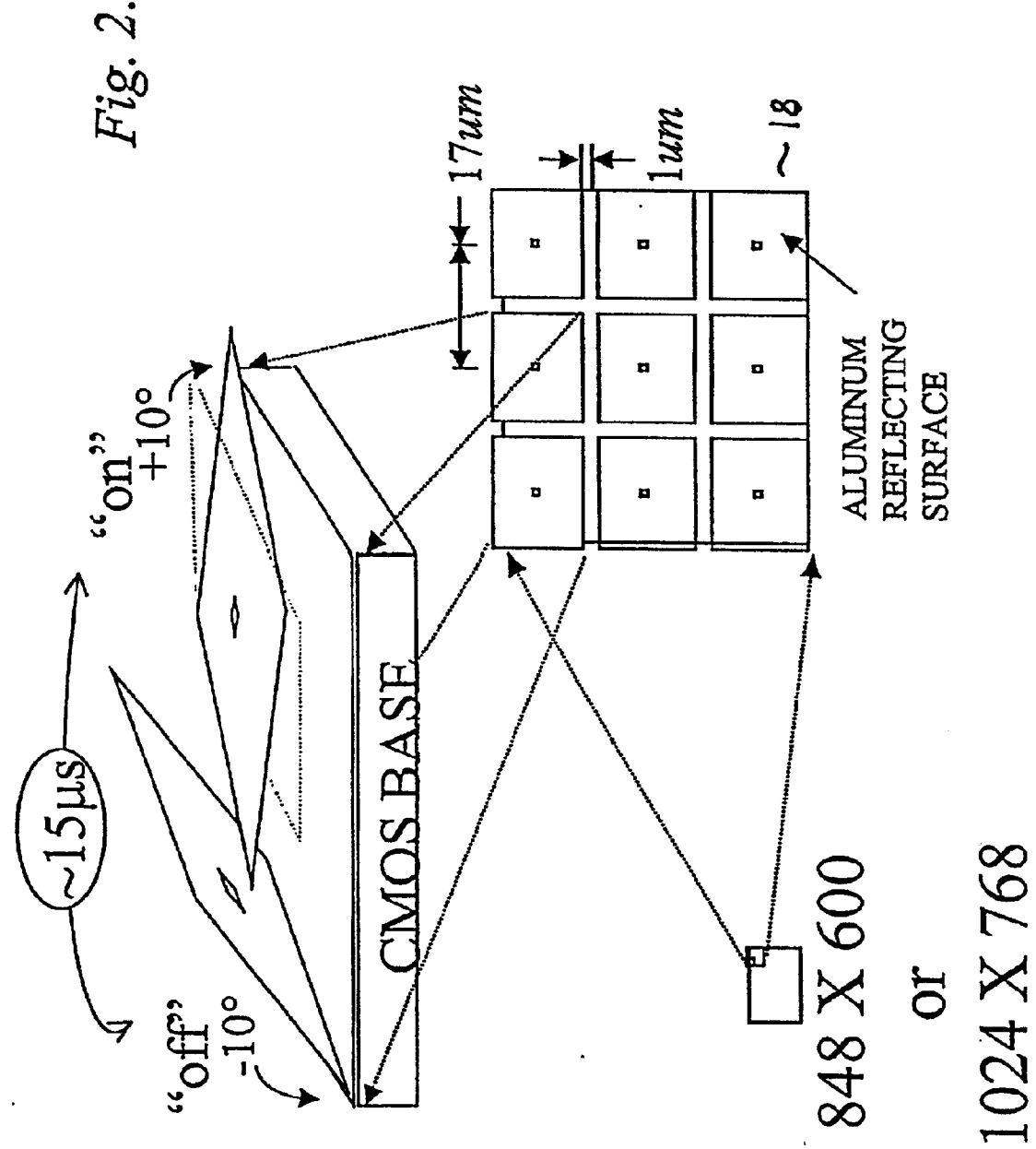

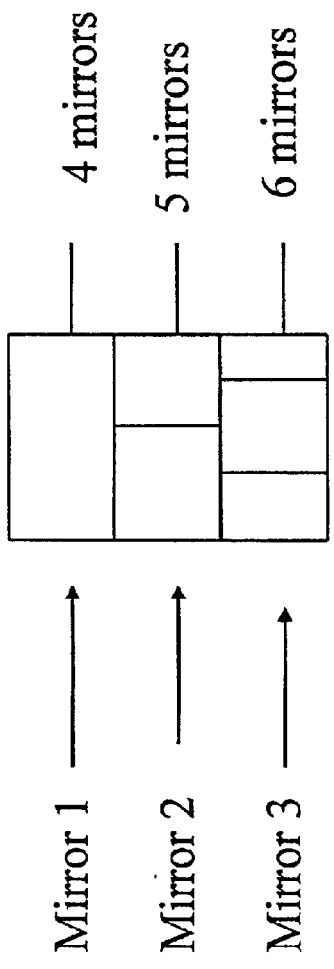
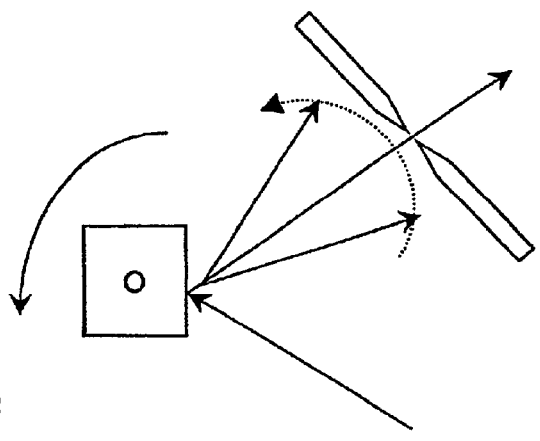
Fig. 14.

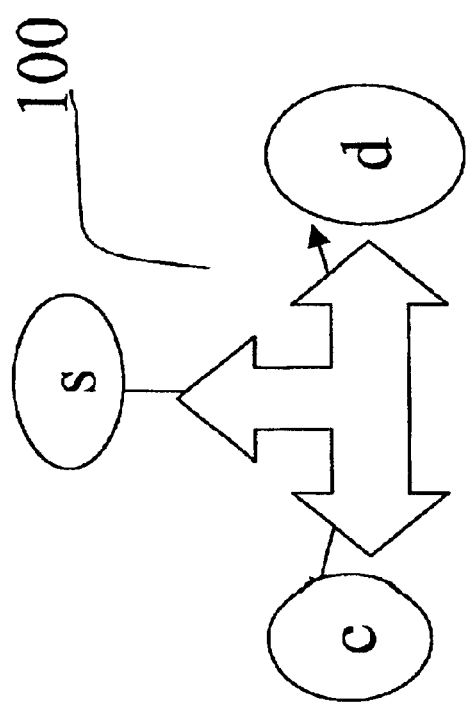
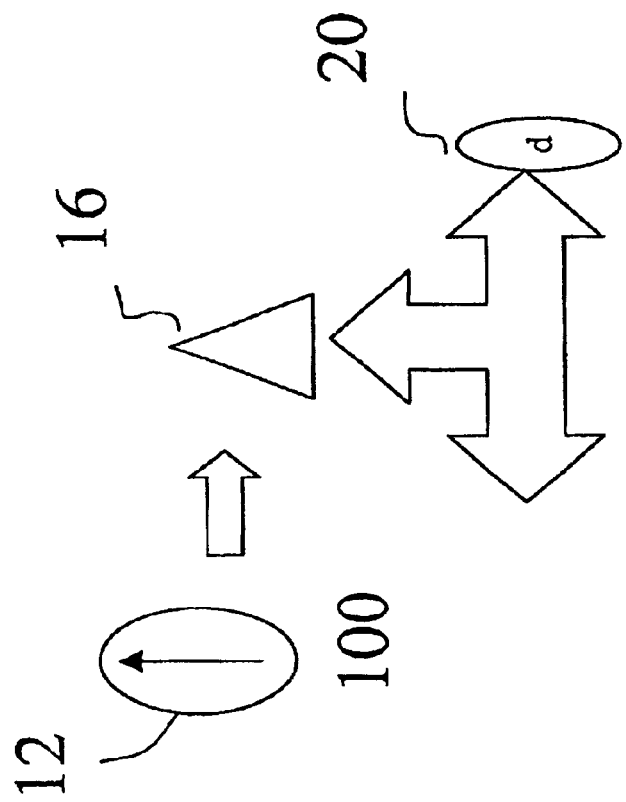

Light mixing

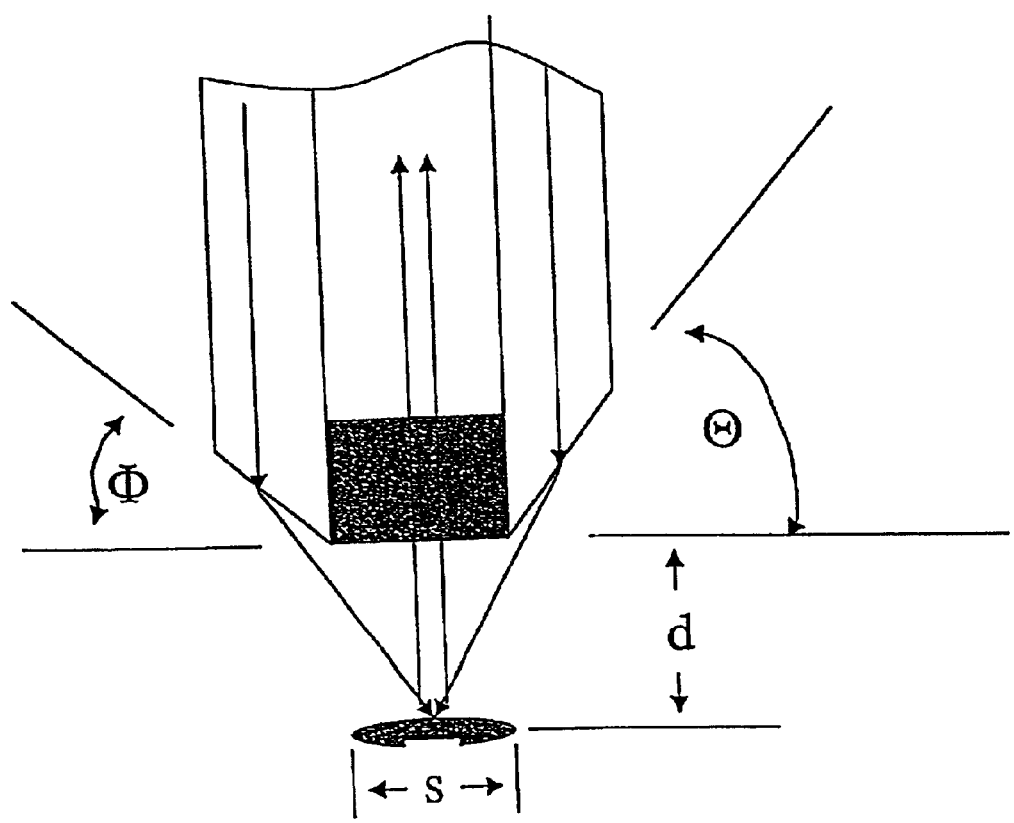
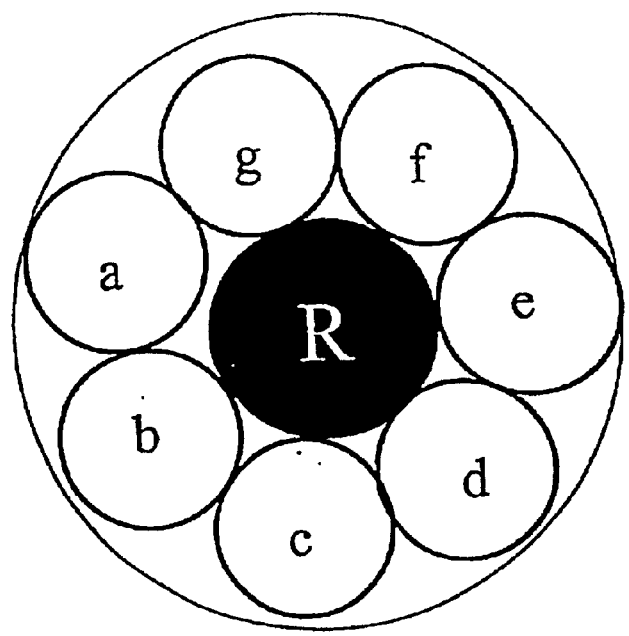
Fig. 32

E-probe for pierced ears

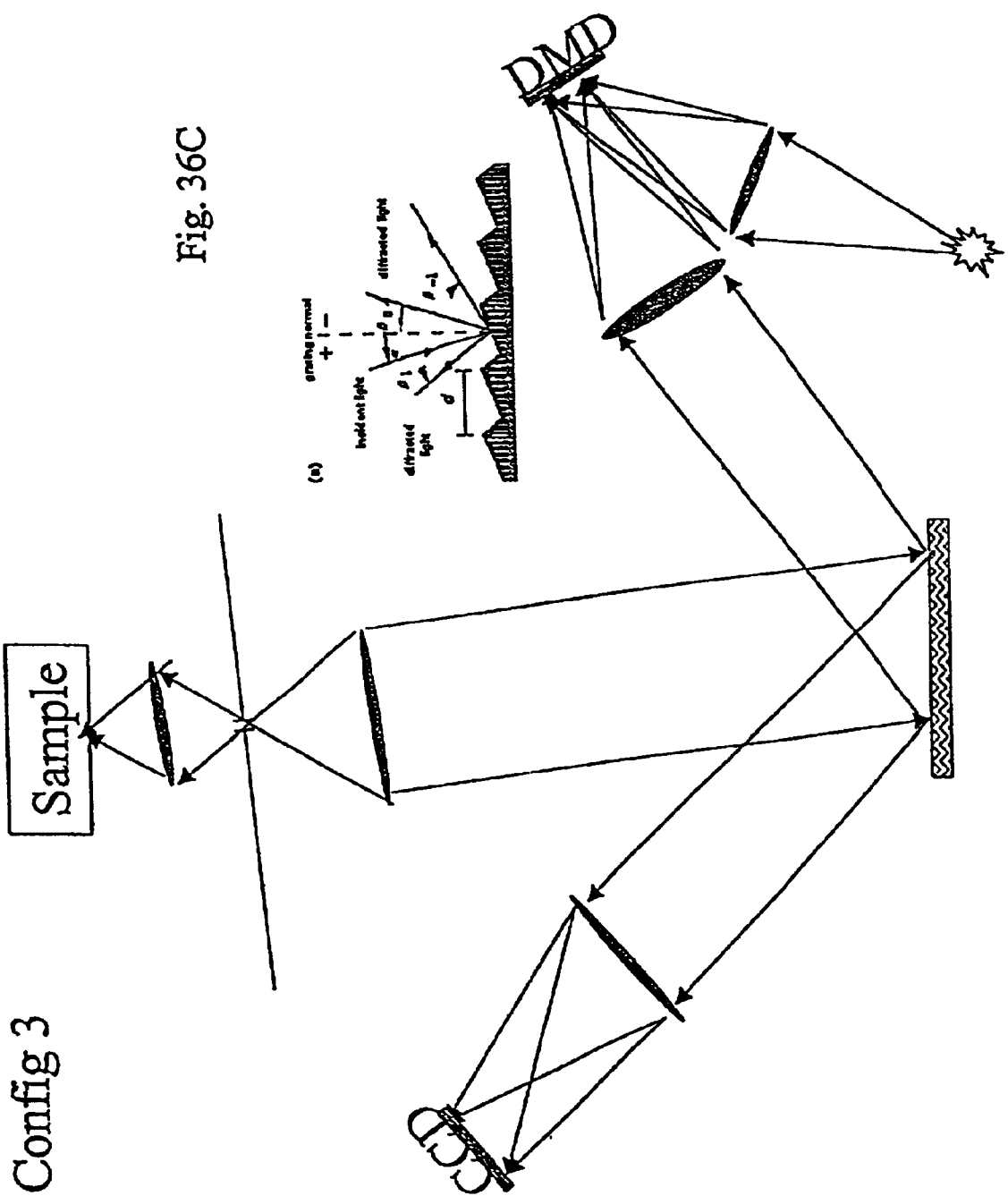

SYSTEM AND METHOD FOR ENCODED SPATIO-SPECTRAL INFORMATION PROCESSING

This application is a continuation-in-part of application Ser. No. 09/672,257, filed Sep. 28, 2000, now U.S. Pat. No. 6,392,748, which is a continuation of application Ser. No. 09/502,758 filed Feb. 11, 2000, now U.S. Pat. No. 6,128,078, which is a continuation of application Ser. No. 09/289,482 filed Apr. 9, 1999, now U.S. Pat. No. 6,046,808.

FIELD OF THE INVENTION

The present invention relates generally to signal processing, and more particularly to devices and methods for use in spectroscopy, imaging, spatial and spectral modulation filtering, controllable radiation source design and related signal processing.

BACKGROUND OF THE INVENTION

Imagers employ either a two-dimensional (2D) multi-channel detector array or a single element detector. Imagers using a 2D detector array measure the intensity distribution of all spatial resolution elements simultaneously during the entire period of data acquisition. Imagers using a single detector require that the individual spatial resolution elements be measured consecutively via a raster scan so that each one is observed for a small fraction of the period of data acquisition. Prior art imagers using a plurality of detectors at the image plane can exhibit serious signal-to-noise ratio problems. Prior art imagers using a single element detector can exhibit more serious signal-to-noise ratio problems. Signal-to-noise ratio problems limit the utility of imagers applied to chemical imaging applications where subtle differences between a sample's constituents become important.

Spectrometers are commonly used to analyze the chemical composition of samples by determining the absorption or attenuation of certain wavelengths of electromagnetic radiation by the sample or samples. Because it is typically necessary to analyze the absorption characteristics of more than one wavelength of radiation to identify a compound, and because each wavelength must be separately detected to distinguish the wavelengths, prior art spectrometers utilize a plurality of detectors, have a moving grating, or use a set of filter elements. However, the use of a plurality of detectors or the use of a macro moving grating has signal-to-noise limitations. The signal-to-noise ratio largely dictates the ability of the spectrometer to analyze with accuracy all of the constituents of a sample, especially when some of the constituents of the sample account for an extremely small proportion of the sample. There is, therefore, a need for imagers and spectrometers with improved signal-to-noise ratios.

Prior art variable band pass filter spectrometers, variable band reject filter spectrometers, variable multiple band pass filter spectrometers or variable multiple band reject filter spectrometers typically employ a multitude of filters that require macro moving parts or other physical manipulation in order to switch between individual filter elements or sets of filter elements for each measurement Each filter element employed can be very expensive, difficult to manufacture and all are permanently set at the time of manufacture in the wavelengths (bands) of radiation that they pass or reject. Physical human handling of the filter elements can damage them and it is time consuming to change filter elements. There is, therefore, a need for variable band pass filter spectrometers, variable band reject filter spectrometers, variable multiple band pass filter spectrometers or variable multiple band reject filter spectrometers without a requirement for discrete (individual) filter elements that have permanently set band pass or band reject properties. There is also a need for variable band pass filter spectrometers, variable band reject filter spectrometers, variable multiple band pass filter spectrometers or variable multiple band reject filter spectrometers to be able to change the filters corresponding to the bands of radiation that are passed or rejected rapidly, without macro moving parts and without human interaction.

In several practical applications it is required that an object be irradiated with radiation having particularly shaped spectrum. In the simplest case when only a few spectrum lines (or bands) are necessary, one can use a combination of corresponding sources, each centered near a required spectrum band. Clearly, however, this approach does not work in a more general case, and therefore it is desirable to have a controllable radiation source capable of providing arbitrary spectrum shapes and intensities. Several types of prior art devices are known that are capable of providing controllable radiation. Earlier prior art devices primarily relied upon various "masking" techniques, such as electronically alterable masks interposed in the optical pathway between a light source and a detector. More recent prior art devices use a combination of two or more light-emitting diodes (LEDs) as radiation sources. In such cases, an array of LEDs or light-emitting lasers is configured for activation using a particular encoding pattern, and can be used as a controllable light source. A disadvantage of these systems is that they rely on an array of different LED elements (or lasers), each operating in a different, relatively narrow spectrum band. In addition, there are technological problems associated with having an array of discrete radiation elements with different characteristics. Accordingly, there is a need for a controllable radiation source, where virtually arbitrary spectrum shape and characteristics can be designed, and where disadvantages associated with the prior art are obviated. Further, it is desirable not only to shape the spectrum of the radiation source, but also encode its components differently, which feature can be used to readily perform several signal processing functions useful in a number of practical applications. The phrase "a spectrum shape" in this disclosure refers not to a mathematical abstraction but rather to configurable spectrum shapes having range (s) and resolution necessarily limited by practical considerations.

In addition to the signal-to-noise issues discussed above, one can consider the tradeoff between signal-to-noise and, for example, one or more of the following resources: system cost, time to measure a scene, and inter-pixel calibration. Thus, in certain prior art systems, a single sensor system may cost less to produce, but will take longer to fully measure an object under study. In prior art multi-sensor systems, one often encounters a problem in which the different sensor elements have different response characteristics, and it is necessary to add components to the system to calibrate for this. It is desirable to have a system with which one gains the lower-cost, better signal-to-noise, and automatic inter-pixel calibration advantages of a single-sensor system, while not suffering all of the time loss usually associated with using single sensors.

SUMMARY OF THE INVENTION

In one aspect, the present invention solves the above-described problems and provides a distinct advance in the art by providing an imager or spectrometer that is less sensitive to ambient noise and that can effectively operate even when used in environments with a high level of ambient radiation. The invention further advances the art of variable band pass filter spectrometers, variable band reject filter spectrometers, variable multiple band pass filter spectrometers or variable multiple band reject filter spectrometers by providing a variable band pass filter spectrometer, variable band reject filter spectrometer, variable multiple band pass filter spectrometer or variable multiple band reject filter spectrometer that: (1) does not require the selection of the bands of wavelengths passed or rejected at the time of manufacture; (2) allows the selection of any desired combination of bands of wavelengths that are passed or rejected; (3) reduces the time to change the bands of wavelengths passed or rejected; and (4) requires no macro moving parts to accomplish a change in the bands of wavelengths passed or rejected.

In a first aspect, the system of the present invention generally includes one or more radiation sources, a two-dimensional array of modulateable micro-mirrors or an equivalent switching structure, a detector, and an analyzer. In a specific embodiment, the two-dimensional switching array is positioned for receiving an image. The micro-mirrors (or corresponding switching elements of the array) are modulated in order to reflect individual spatially-distributed radiation components of the image toward the detector. In a preferred embodiment, the modulation is performed using known and selectively different modulation rates.

According to this aspect of the invention, a detector is oriented to receive the combined radiation components reflected from the array and is operable to generate an output signal representative of the combined radiation incident thereon. The analyzer is operably coupled with the detector to receive the output signal and to demodulate the signal to recover signals representative of each of the individual spatially distributed radiation components of the image. The analyzer can be configured to recover all reflected components or to reject some unnecessary components of the recovered signals from the combined reflections.

By using micro-mirrors that receive the individual spectral or spatial radiation components and then modulate these components at different modulation rates, all of the radiation components can be focused onto a single detector and then demodulated to maximize the signal-to-noise ratio (SNR) of the detector. Various techniques for enhancing the SNR of the system are presented as well.

In another important aspect, the present invention provides a distinct advance in the state of the art by enabling the design of a controllable radiation source, which uses no masking elements, which are generally slow and cumbersome to operate, and no discrete light sources, which also present a number of technical issues in practice. Instead, the controllable radiation source in accordance with a preferred embodiment is implemented using a broadband source illuminating a two-dimensional array of switching elements, such as a DMA. Modulation of the individual switching elements of the array provides an easy mechanism for spatio-spectral encoding of the input radiation, which encoding can be used in a number of practical applications.

In accordance with another aspect of the invention, a two-dimensional array of switching elements, such as a DMA, can be configured and used as a basic building block for various optical processing tasks, and is referred to as an optical synapse processing unit (OSPU). Combinations of OSPUs with standard processing components can be used in the preferred embodiments of the present invention in a number of practical applications, including data compression, feature extraction and others. In a specific embodiment, a spectrometer using a controlled radiation source provides for very rapid analysis of a sample using an orthogonal set of basis functions, such as Hadamard or Fourier transform techniques, resulting in significantly enhanced signal-to-noise ratio.

The present invention gains the lower-cost, better signal-to-noise, and automatic inter-pixel calibration advantages of single-sensor systems, while not suffering all of the time loss usually associated with using single sensors, because it allows for adaptive and tunable acquisition of only the desired information, as opposed to prior-art systems which are generally full data-cube acquisition devices requiring additional post processing to discover or recover the knowledge ultimately sought in the application of the system. One skilled in the art will recognize that, while the invention here is described using 2D arrays of micro-mirrors, any 2D spatial light modulator can be used. It should also be noted, that a pair, or a few 1D spatial light modulators can be combined to effectively produce a 2D spatial light modulator for applications that involve raster scanning, Walsh-Hadamard scanning, or scanning or acquisition with any separable library of patterns.

It is intended that the devices and methods in this application in general are capable of operating in various ranges of electromagnetic radiation, including the ultraviolet, visible, infrared, and microwave spectrum portions. Further, it will be appreciated by those of skill in the art of signal processing, be it acoustic, electric, magnetic, etc., that the devices and techniques disclosed herein for optical signal processing can be applied in a straight-forward way to those other signals as well.

BRIEF DESCRIPTION OF THE DRAWINGS

The present invention will be understood and appreciated more fully from the following detailed description, taken in conjunction with the drawings in which:

FIG. 2 is a plan view of a micro-mirror array used in the present invention;

FIGS. 11–14 illustrate alternative embodiments of a modulating spectrometer in accordance with this invention; FIG. 12 illustrates an embodiment of a complete modulating spectrometer in which the DMA element is replaced by the concave mirrors of FIG. 11. FIG. 13 illustrates a modulating lens spectrometer using lenses instead of DMA, and a "barber pole" arrangement of mirrors to implement variable modulation. FIG. 14 illustrates a "barber pole" modulator arrangement;

FIGS. 18A and 18B illustrate in a diagram form an optical synapse processing unit (OSPU) used as a processing element in accordance with the present invention;

FIG. 19 illustrates in a diagram form the design of a spectrograph using OSPU;

FIG. 24 is a flow chart of a raster-scan used in one embodiment of the present invention; FIG. 25 is a flowchart of a Walsh-Hadamard scan used in accordance with another embodiment of the invention. FIG. 26 is a flowchart of a multi-scale scan, used in a different embodiment.

FIG. 31 illustrates hyperspectral imaging from airborne camera;

FIG. 32 is an illustration of a hyperspectral image of human skin;

FIG. 32 shows an axial and a cross-sectional views of a fiber optic assembly;

FIGS. 36A, 36B and 36C illustrate different configurations of a hyperspectral adaptive wavelength advanced illuminating imaging spectrograph (HAWAIIS) in accordance with this invention;

DETAILED DESCRIPTION OF THE PREFERRED EMBODIMENTS

In one aspect, the present invention concerns the analysis of radiation passing through or reflected from a sample of a material of interest. Since signal processing in this aspect of the invention is performed after the sample has been irradiated, in the disclosure in Section I below it is referred to as post-sample processing. Section II deals with the aspect of the invention in which radiation has already been processed prior to its interaction with the sample (e.g. based on a priori knowledge), and is accordingly referred to as pre-sample processing. Various processing techniques applicable in both pre-sample and post-sample processing are considered in Section III. Finally, Section IV illustrates the use of the proposed techniques and approaches in the description of various practical applications.

I. Post-sample Processing
A. The Basic System

Figure 1A:
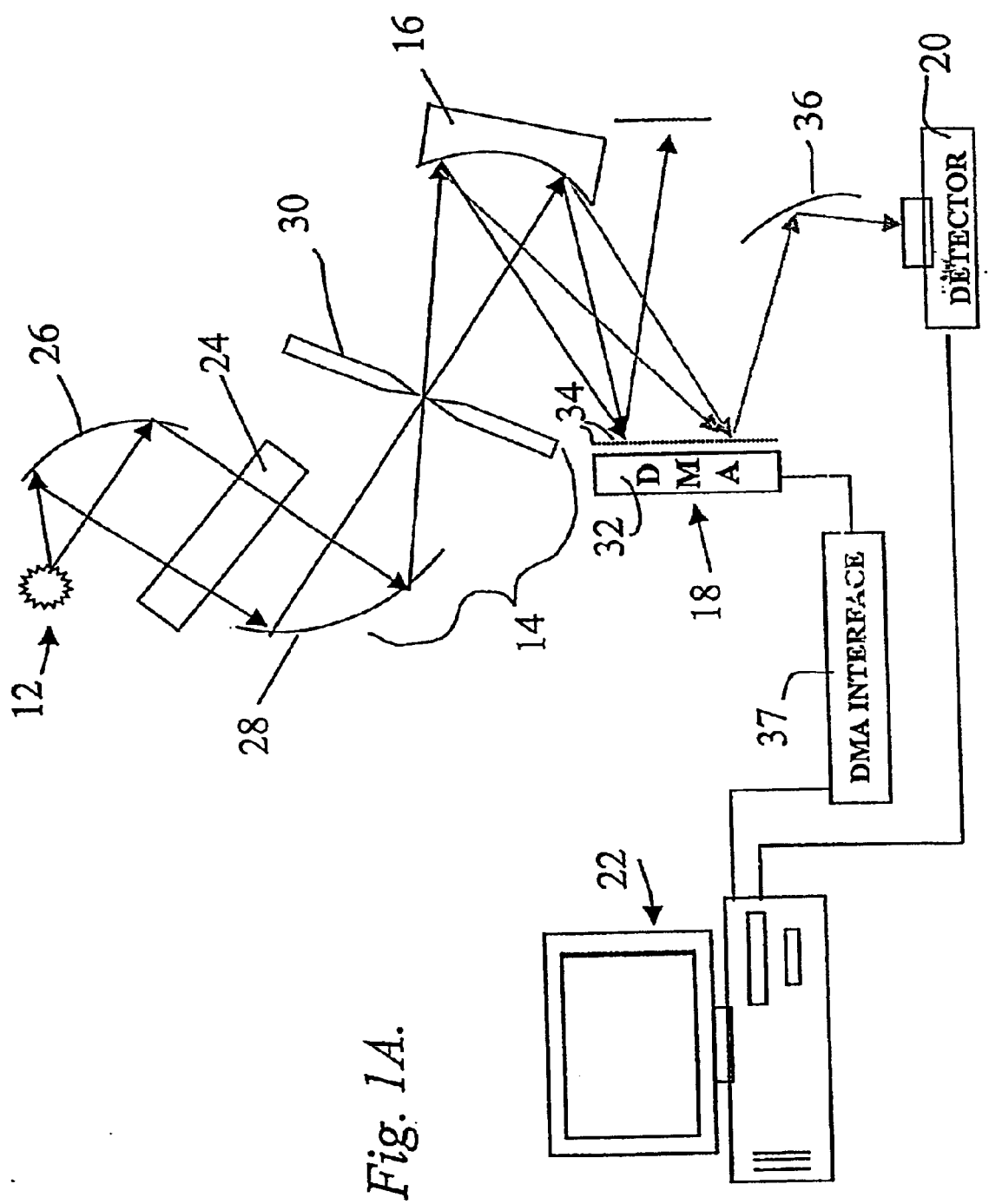
FIGS. 1A and 1B are schematic diagrams illustrating a spectrometer constructed in accordance with two embodiments of the invention.
Figure 1B:
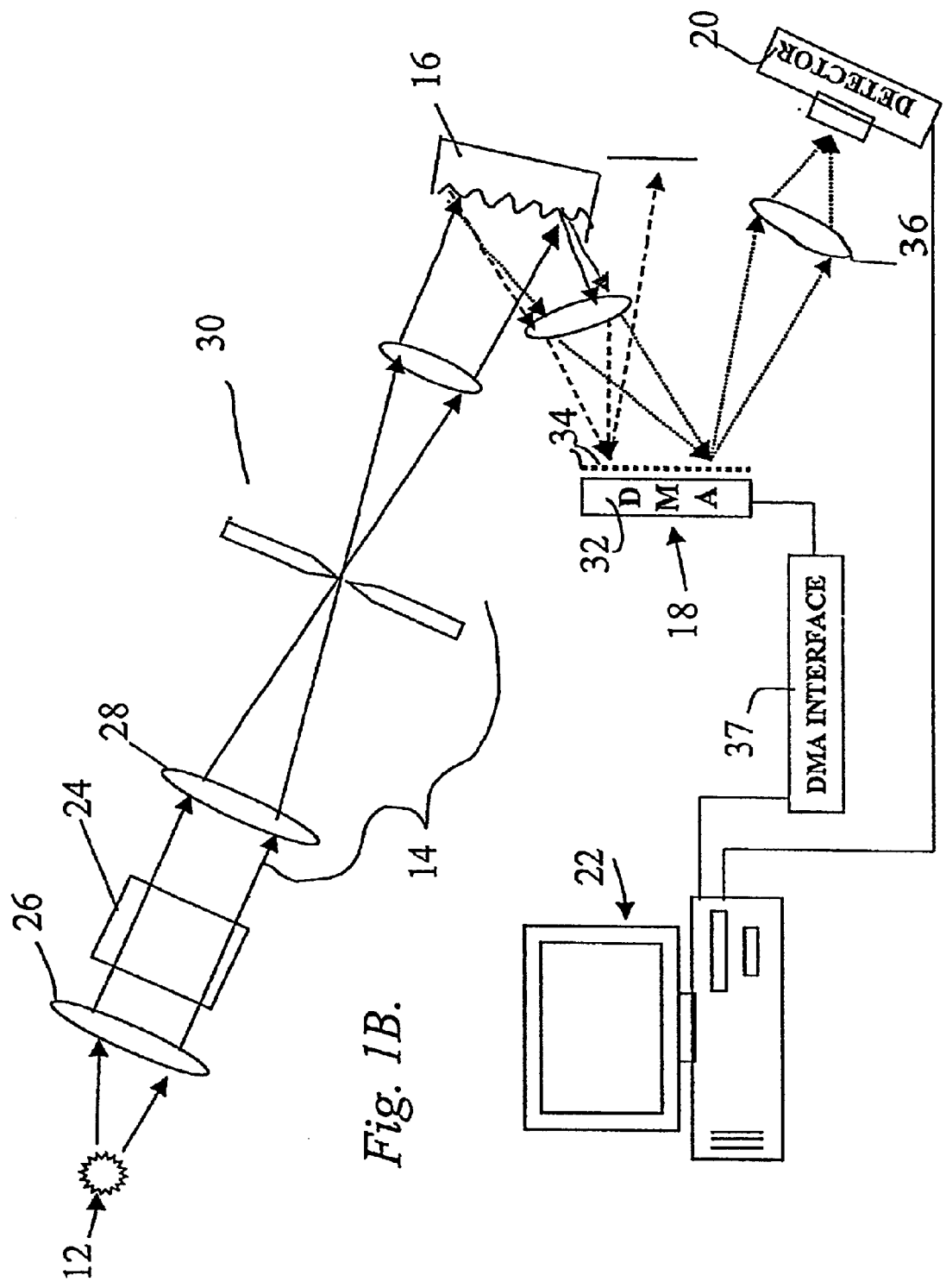

Turning now to the drawing figures and particularly FIG. 1A and 1B, a spectrometer assembly 10 constructed in accordance with one embodiment of the invention is illustrated. With reference to FIG. 1A the device broadly includes a source 12 of electromagnetic radiation, a mirror and slit assembly 14, a wavelength dispersing device 16, a spatial light modulator 18, a detector 20, and an analyzing device 22.

In particular, the electromagnetic radiation source 12 is operable to project rays of radiation onto or through a sample 24 that is to be analyzed, such as a sample of body tissue or blood. The radiation source may be any device that generates electromagnetic radiation in a known wavelength spectrum such as a globar, hot wire, or light bulb that produces radiation in the infrared spectrum. To increase the amount of rays that are directed to the sample, a parabolic reflector 26 may be interposed between the source 12 and the sample 24. In a specific embodiment, the source of electromagnetic radiation is selected as to yield a continuous band of spectral energies, and is referred to as the source radiation. It should be apparent that the energies of the radiation source are selected to cover the spectral region of interest for the particular application.

The mirror and slit assembly 14 is positioned to receive the radiation rays from the source 12 after they have passed through the sample 24 and is operable to focus the radiation onto and through an entrance slit 30. The collection mirror 28 focuses the radiation rays through slit 30 and illuminates the wavelength dispersing device 16. As shown in diagram form in FIG. 1B, in different embodiments of the invention radiation rays from the slit may also be collected through a lens 15, before illuminating a wavelength dispersion device 16.

The wavelength dispersing device 16 receives the beams of radiation from the mirror and slit assembly 14 and disperses the radiation into a series of lines of radiation each corresponding to a particular wavelength of the radiation spectrum. The preferred wavelength dispersing device is a concave diffraction grating; however, other wavelength dispersing devices, such as a prism, may be utilized. In a specific embodiment, the wavelengths from the dispersing device 16 are in the near infrared portion of the spectrum and may cover, for example, the range of 1650–1850 nanometers (nm). It should be emphasized, however, that in general this device is not limited to just this or to any spectral region. It is intended that the dispersion device in general is capable of operating in other ranges of electromagnetic radiation, including the ultraviolet, visible, infrared, and microwave spectrum portions, as well as acoustic, electric, magnetic, and other signals, where applicable.

The spatial light modulator (SLM) 18 receives radiation from the wavelength dispersing device 16, individually modulates each spectral line, and reflects the modulated lines of radiation onto the detector 20. As illustrated in FIG. 2, the SLM is implemented in a first preferred embodiment as a micro-mirror array that includes a semi-conductor chip or piezoelectric device 32 having an array of small reflecting surfaces 34 thereon that act as mirrors. One such micro-mirror array is manufactured by Texas Instruments and is described in more detail in U.S. Pat. No. 5,061,049, hereby incorporated into the present application by reference. Those skilled in the art will appreciate that other spatial light modulators, such as a magneto-optic modulator or a liquid crystal device may be used instead of the micro-mirror array. Various embodiments of such devices are discussed in more detail below.

Figure 3:
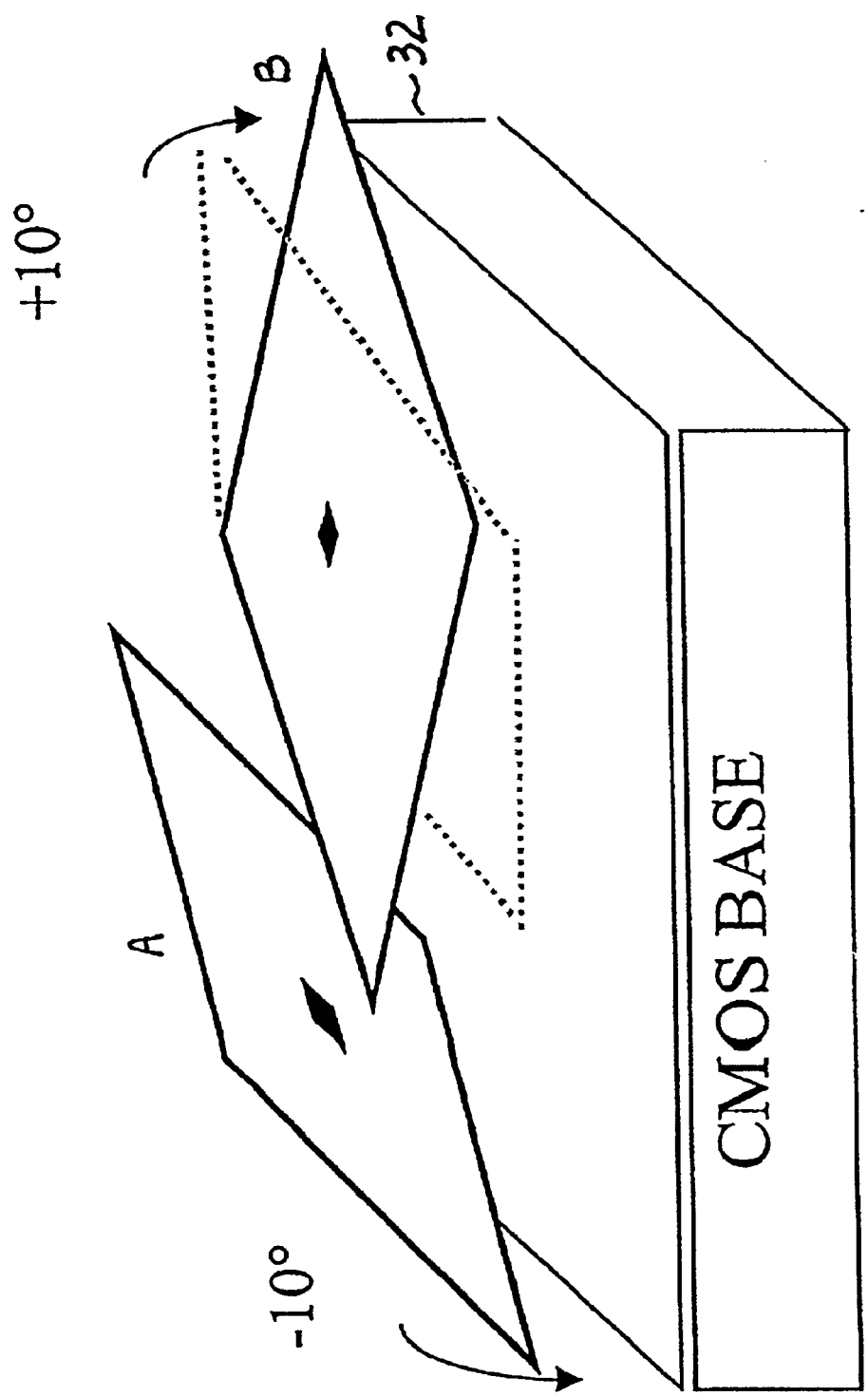
FIG. 3 is a schematic diagram of two micro-mirrors illustrating the modulations of the mirrors of the micro-mirror device of FIG. 2.

The semi-conductor 32 of the micro-mirror array 18 is operable to individually tilt each mirror along its diagonal between a first position depicted by the letter A and a second position depicted by the letter B in FIG. 3. In preferred forms, the semi-conductor tilts each mirror 10 degrees in each direction from the horizontal. The tilting of the mirrors 34 is preferably controlled by the analyzing device 22, which may communicate with the micro-mirror array 18 through an interface 37.

The micro-mirror array 18 is positioned so that the wavelength dispersing device 16 reflects each of the lines of radiation upon a separate column or row of the array. Each column or row of mirrors is then tilted or wobbled at a specific and separate modulation frequency. For example, the first row of mirrors may be wobbled at a modulation frequency of 100 Hz, the second row at 200 Hz, the third row at 300 Hz, etc. In a specific embodiment, the mirrors are calibrated and positioned so that they reflect all of the modulated lines of radiation onto a detector 20. Thus, even though each column or row of mirrors modulates its corresponding line of radiation at a different modulation frequency, all of the lines of radiation are focused onto a single detector.

The detector 20, which may be any conventional radiation transducer or similar device, is oriented to receive the combined modulated lines of radiation from the micro-mirror array 18. The detector is operable for converting the radiation signals into a digital output signal that is representative of the combined radiation lines that are reflected from the micro-mirror array. A reflector 36 may be interposed between the micro-mirror array 18 and the detector 20 to receive the combined modulated lines of radiation from the array and to focus the reflected lines onto the detector.

The analyzing device 22 is operably coupled with the detector 20 and is operable to receive and analyze the digital output signal from the detector. The analyzing device uses digital processing techniques to demodulate the signal into separate signals each representative of a separate line of radiation reflected from the micro-mirror array. For example, the analyzing device may use discrete Fourier transform processing to demodulate the signal to determine, in real time, the intensity of each line of radiation reflected onto the detector. Thus, even though all of the lines of radiation from the micro-mirror array are focused onto a single detector, the analyzing device can separately analyze the characteristics of each line of radiation for use in analyzing the composition of the sample.

Figure 4:
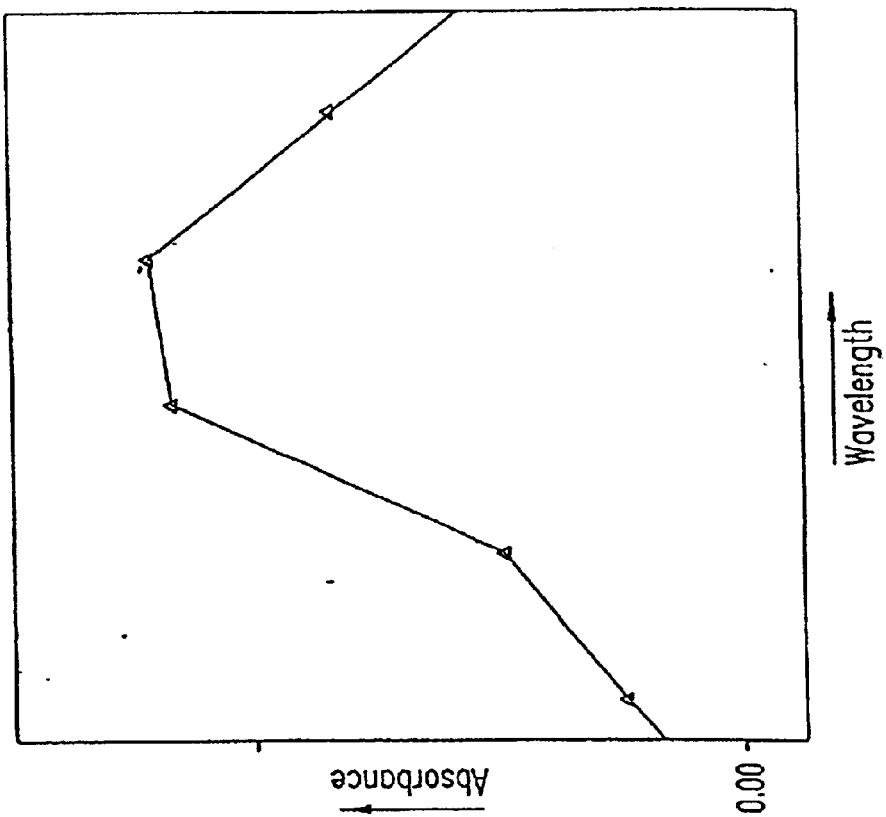
FIG. 4 is a graph illustrating an output signal of the spectrometer when used to analyze the composition of a sample.

In accordance with one embodiment of this invention, the analyzing device is preferably a computer that includes spectral analysis software. FIG. 4 illustrates an output signal generated by the analyzing device in accordance with one embodiment. The output signal illustrated in FIG. 4 is a plot of the absorption characteristics of five wavelengths of radiation from a radiation source that has passed through a sample.

Figure 5:
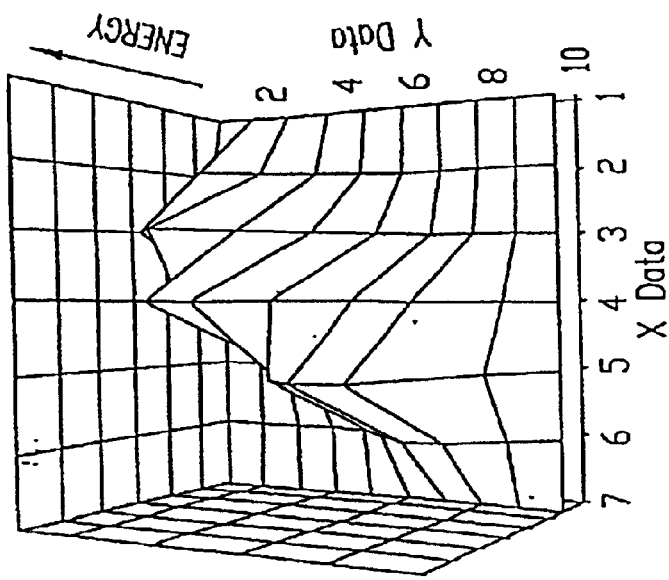
FIG. 5 is a graph illustrating an output signal of the imager when used for imaging purposes.
Figure 6:
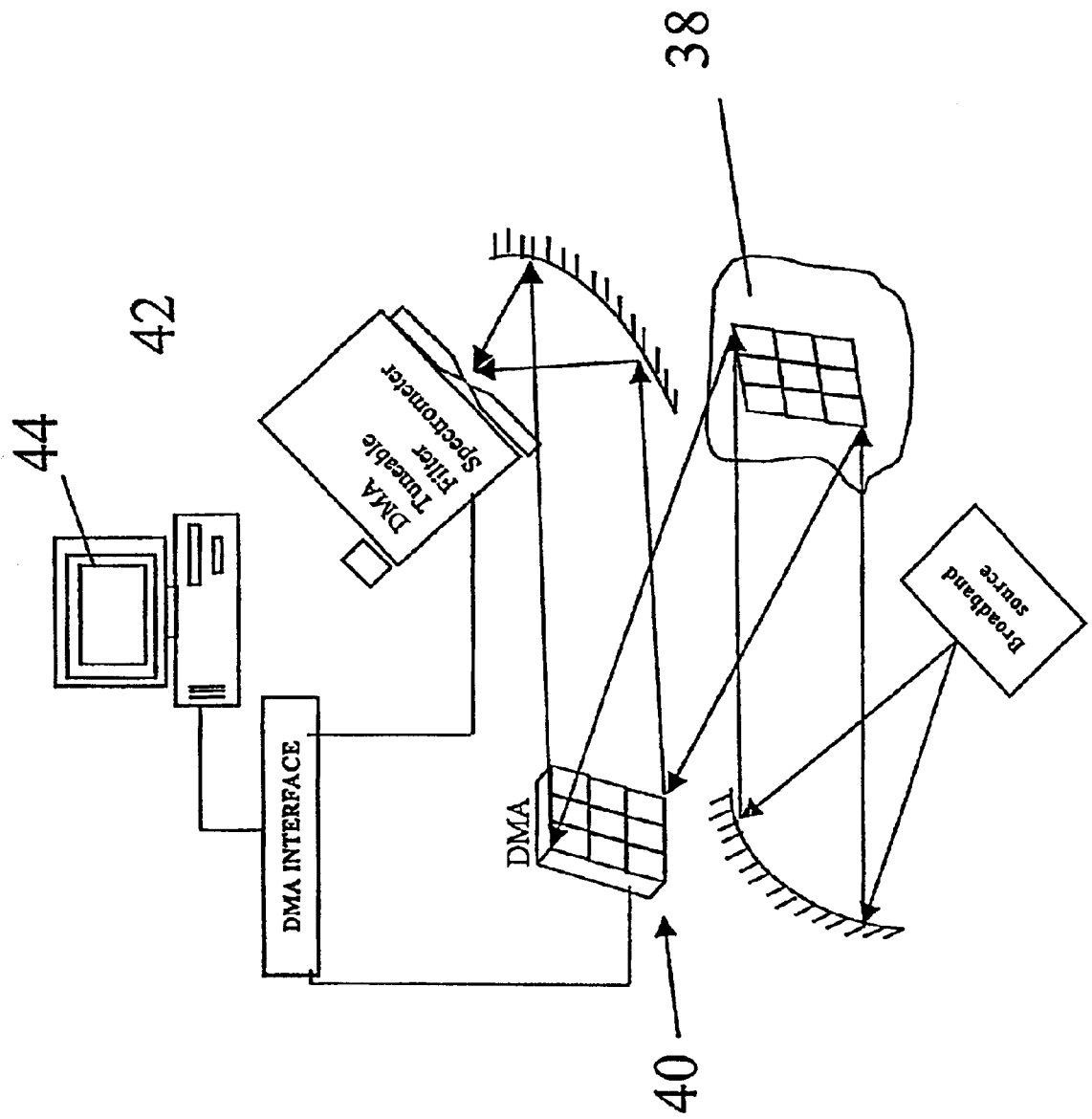
FIG. 6 is a schematic diagram illustrating an imager constructed in accordance with a preferred embodiment of the invention.
Figure 6A:
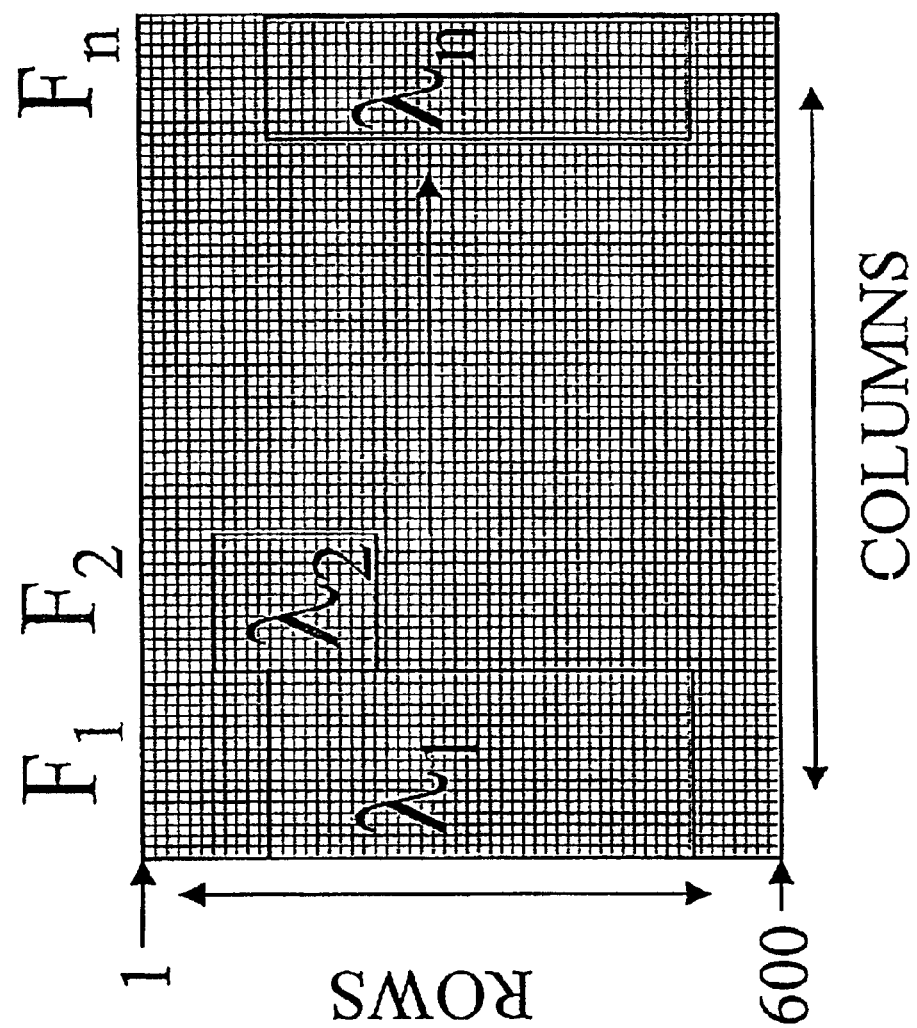
FIG. 6A illustrates spatio-spectral distribution of a DMA, where individual elements can be modulated.

In one embodiment of the system of this invention illustrated in FIG. 6A, it is used for digital imaging purposes. In particular, when used as an imaging device, an image of a sample 38 is focused onto a micro-mirror array 40 and each micro-mirror in the array is modulated at a different modulation rate. The micro-mirror array geometry is such that some or all of the reflected radiation impinges upon a single detector element 42 and is subsequently demodulated to reconstruct the original image improving the signal-to-noise ratio of the imager. Specifically, an analyzing device 44 digitally processes the combined signal to analyze the magnitude of each individual pixel. FIG. 6B illustrates spatio-spectral distribution of the DMA, where individual elements can be modulated. FIG. 5 is a plot of a three dimensional image showing the magnitude of each individual pixel.

Figure 7:
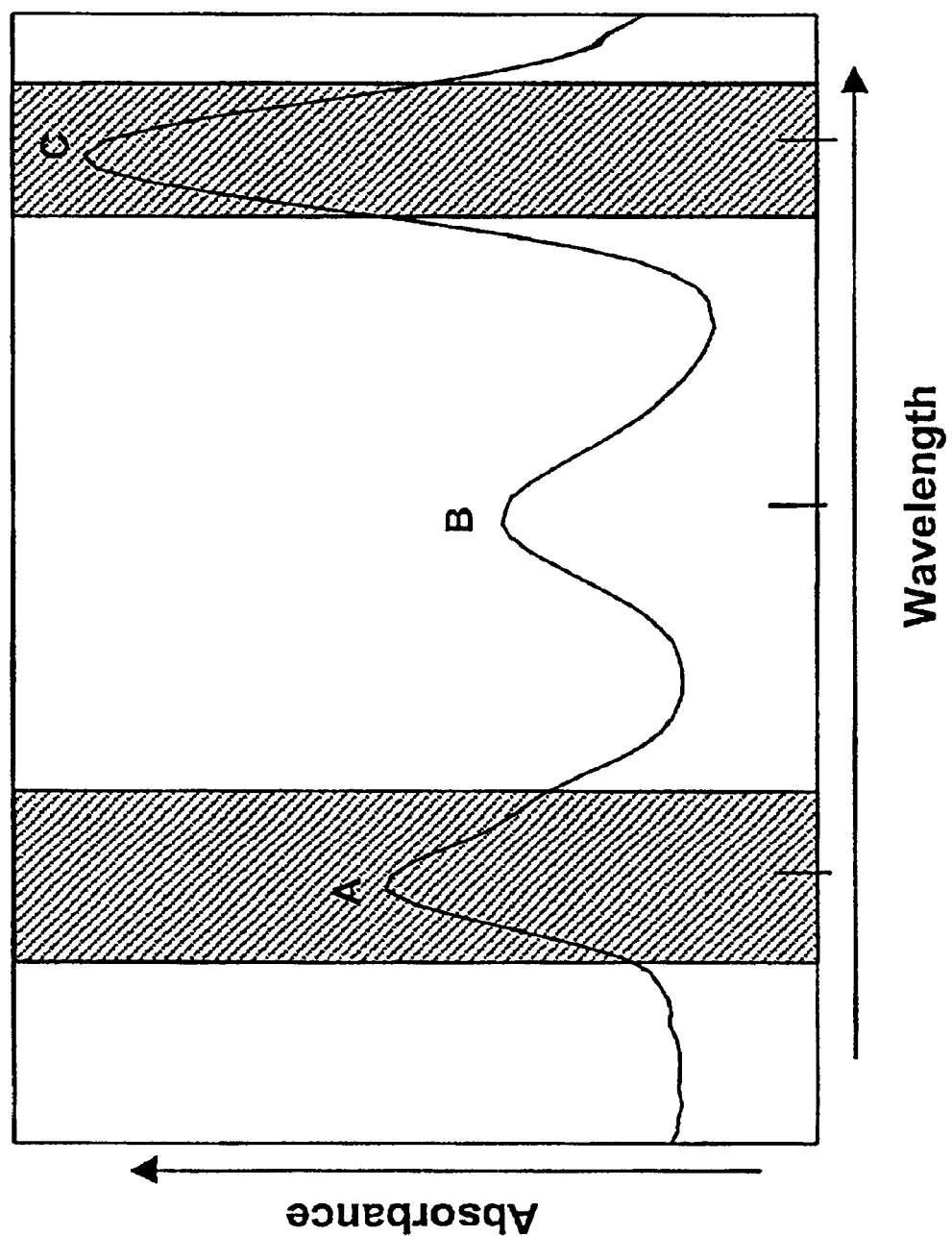
FIG. 7 is an illustration of the input to the DMA Filter Spectrometer and its use to pass or reject wavelength of radiation specific to constituents in a sample.

FIG. 7 illustrates the output of a digital micro-mirror array (DMA) filter spectrometer used as a variable band pass filter spectrometer, variable band reject filter spectrometer, variable multiple band pass filter spectrometer or variable multiple band reject filter spectrometer. In this embodiment, the combined measurement of the electromagnetic energy absorbed by sample constituents A and C is of interest. The shaded regions in FIG. 7 illustrate the different regions of the electromagnetic spectrum that will be allowed to pass to the detector by the DMA filter spectrometer. The wavelengths of electromagnetic radiation selected to pass to the detector correspond to the absorption band for compound A and absorption band for compound C in a sample consisting of compounds A, B, and C. The spectral region corresponding to the absorption band of compound B and all other wavelengths of electromagnetic radiation are rejected. Those skilled in the art will appreciate that the DMA filter spectrometer is not limited to the above example and can be used to pass or reject any combination of spectral resolution elements available to the DMA. Various examples and modifications are considered in detail below.

As a DMA filter imager the spatial resolution elements (pixels) of an image can be selectively passed or rejected (filtered) according to the requirements of the image measurement. The advantages of both the DMA filter spectrometer and DMA filter imager are:

(1) All spectral resolution elements or spatial resolution elements corresponding to the compounds of interest in a particular sample can be directed simultaneously to the detector for measurement This has the effect of increasing the signal-to-noise ratio of the measurement.

(2) The amount of data requiring processing is reduced. This reduces storage requirements and processing times.

B. Modulated Spectral Filter Design (i) Design Basics

The preceding section described the components of the basic system used in accordance with the present invention, and their operation. The focus of this section is on the design of specific modulated spectral filters using the spatial light modulator (SLM) 18, which in a preferred embodiment is implemented using a digital micro-mirror array (DMA).

Figure 8:
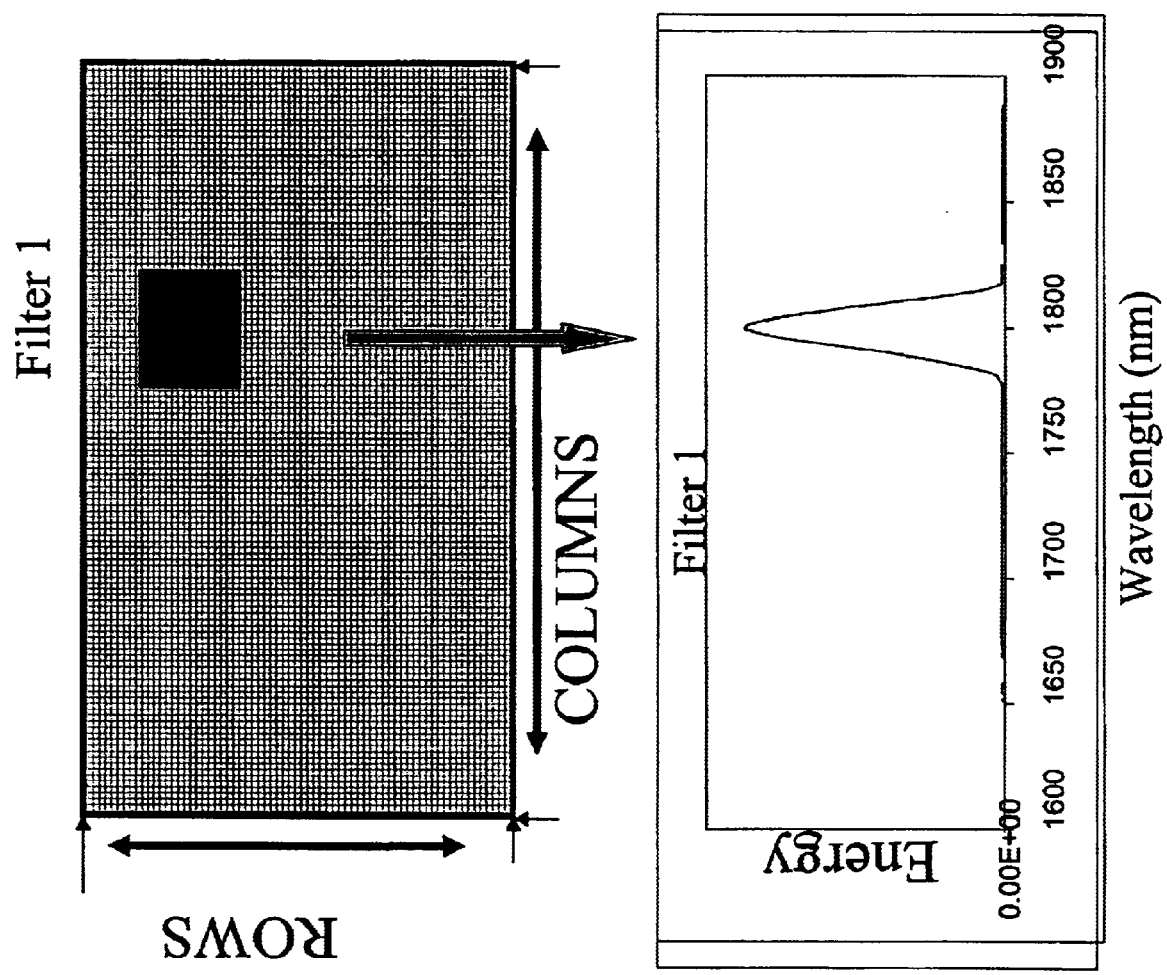
FIG. 8 illustrates the design of a band pass filter in accordance with the present invention (top portion) and the profile of the radiation passing through the filter (bottom portion)

As noted above, using a DMA one can provide one or more spectral band pass or band-reject filter (s) with a chosen relative intensity. In particular, in accordance with the present invention the radiation wavelengths that are reflected in the direction of the detector are selected by specific columns of micro-mirrors of the DMA, as illustrated in FIG. 8. The relative intensity of the above spectral band is controlled by the selection of specific area of micro-mirrors on the DMA, represented by the dark area designated "A" in FIG. 8. Thus, the dark area shown in FIG. 8 is the mirrors that direct specific wavelength radiation, i.e., spectral band, to the detector. Clearly, the "on" mirrors in the dark area create a band-pass filter, the characteristics of which are determined by the position of the "on" area in the DMA. The bottom portion of the figure illustrates the profile of the radiation reaching the detector.

FIG. 8 also demonstrates the selection of specific rows and columns of mirrors in the DMA used to create one spectral band filter with a single spectral mode. It should be apparent, however, that using the same technique of blocking areas in the DMA one can obtain a plurality of different specific spectral band filters, which can have multi-modal characteristics. The design of such filters is illustrated in FIG. 9.

Figure 9:
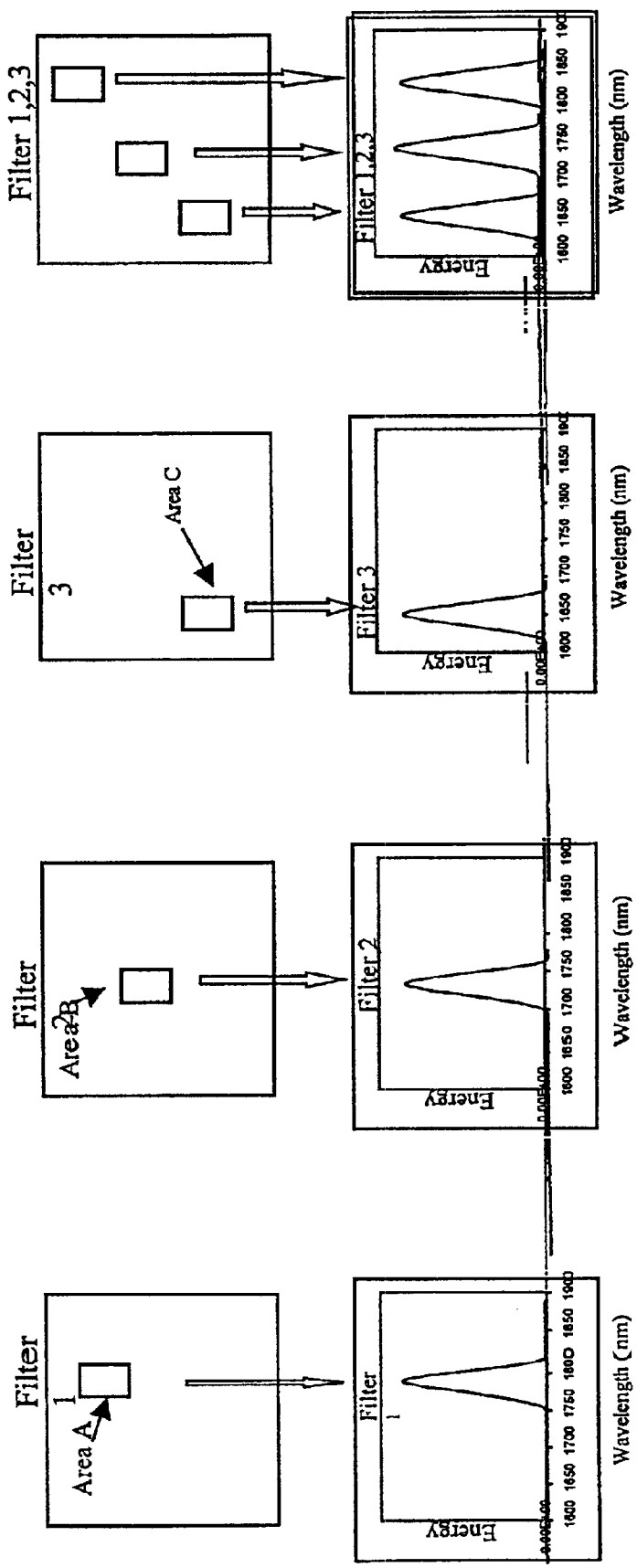
FIG. 9 illustrates the design of multi-modal band-pass or band-reject filters with corresponding intensity plots, in accordance with the present invention.

As shown in FIG. 9, a multitude of different specific filters can be designed on one DMA using simple stacking. FIG. 9 illustrates the creation of several filters by selective reflection from specific micro-mirrors. In particular, the left side of the figure illustrates the creation of three different filters, designated 1, 2, and 3. This is accomplished by the selection of specific mirrors on the DMA, as described above with reference to FIG. 8. The total collection of spectral band filters is shown at the bottom-left of this figure. The spectral band provided by each filter is shown on the right-hand side of the figure. The bottom right portion illustrates the radiation passing through the combination of filters 1, 2 and 3.

The above discussion describes how the relative intensity of each spectral band can be a function of the DMA area used in the reflection. The following table illustrates the linear relationship between areas of the DMA occupied by individual filters, and the resulting filter. Clearly, if the entire DMA array is in the "on" position, there will be no filtering and in principle the input radiation passes through with no attenuation.

| FIG. 9, left side Reflected radiation from micro-mirrors | FIG. 9, right side Filter created |
|---|---|
| area A | 1 |
| area B | 2 |

-continued

| FIG. 9, left side Reflected radiation from micro-mirrors | FIG. 9, right side Filter created |
|---|---|
| area C | 3 |
| areas a + b + c | 1 + 2 + 3 |

Figure 10:
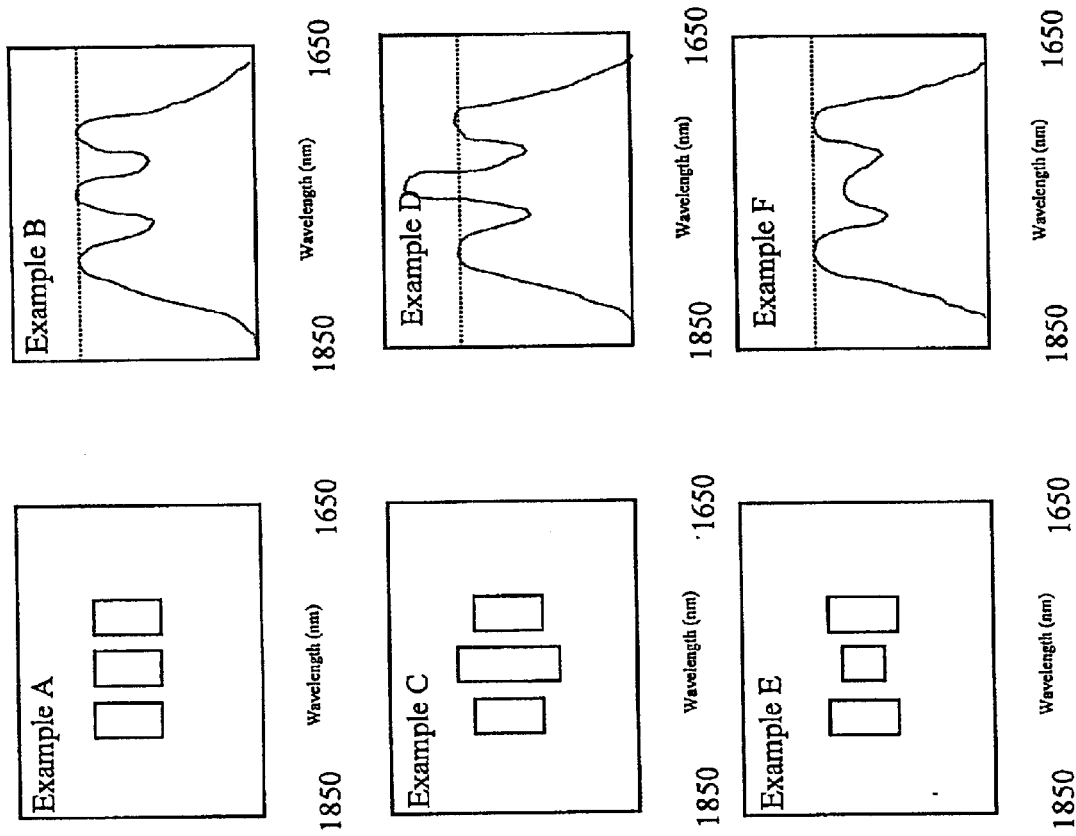
FIG. 10 illustrates the means for the intensity variation of a spectral filter built in accordance with this invention.

FIG. 10 illustrates the means for the intensity variation of a spectral filter built in accordance with this invention, and is summarized in the table below.

| Example A | Example B |
|---|---|
| Reflection from a DMA See FIGS. 8 and 9. Reflection areas 1, 2, and 3 create spectral filter 1, 2 and 3 respectively. area 1 = area 2 = area 3 | The intensity recorded at the detector for example A for the combination filter 1, 2, and 3, Intensity, I, $I_1 = I_2 = I_3$ |

| Example C | Example D |
|---|---|
| The reflection of area 2 of the DMA is increased. area 1 = area 3 < area 2 | The intensity recorded at the detector for filters 1, 2, and 3 is $I_1 \approx I_3 < I_2$ |

| Example E | Example F |
|---|---|
| The reflection of area 2 of the DMA is decreased area 1 = area 3 < area 2 | The intensity recorded at the detector for filter 1, 2, and 3 is $I_1 = I_3 < I_2$ |

(ii) Modulation

FIGS. 9 and 10 illustrate the ability to design spectral filters with different characteristics using a DMA. The important point to keep in mind is that different spectral components of the radiation from the sample have been separated in space and can be filtered individually. It is important to retain the ability to process individual spectral components separately. To this end, in accordance with the present invention, spectral components are modulated.

The basic idea is to simply modulate the output from different filters differently, so one can identify and process them separately. In a preferred embodiment, different modulation is implemented by means of different modulation rates. Thus, with reference to FIG. 9, the output of filter 1 is modulated at rate $M_1$; output of filter 2 is modulated at rate $M_2$, and filter 3 is modulated using rate $M_3$, where $M_1 \neq M_2 \neq M_3$. In different embodiments, modulation may be achieved by assigning a different modulation encodement to each filter, with which it is modulated over time.

As a result, a system built in accordance with the present invention is capable of providing: a) Spectral bandwidth by selection of specific columns of micro-mirrors in an array; b) Spectral intensity by selection of rows of the array; and c) Spectral band identification by modulation. All of the above features are important in practical applications, as discussed in Section IV below.

C. Alternative Embodiments (i) Modulating Spectrometers without a DMD.

FIGS. 11–14 illustrate alternative embodiments of a modulating spectrometer in accordance with this invention, where the DMA is replaced with different components. In particular, FIGS. 11A and B show an embodiment in which the DMA is replaced with fixed elements, in this case concave mirrors. The idea is to use fixed spectral grating, which masks out spectrum block components that are not needed and passes those which are.

The idea here is that the broadly illuminated dispersive element distributes spectral resolution elements in one dimension so that in the orthogonal dimension one can collect light of the same wavelengths. With reference to FIG. 6A one can see that at a particular defined plane, herein called the focal plane, one has a wavelength axis (x or columns) and a spatial axis (y or rows). If one were to increase the number of spatial resolution elements (y) that are allowed to pass energy through the system and out of the exit aperture for any given wavelength (x), or spectral resolution element (x), this would have the effect of increasing the intensity of the particular spectral resolution elements' intensity at the detector.

Figure 11B:
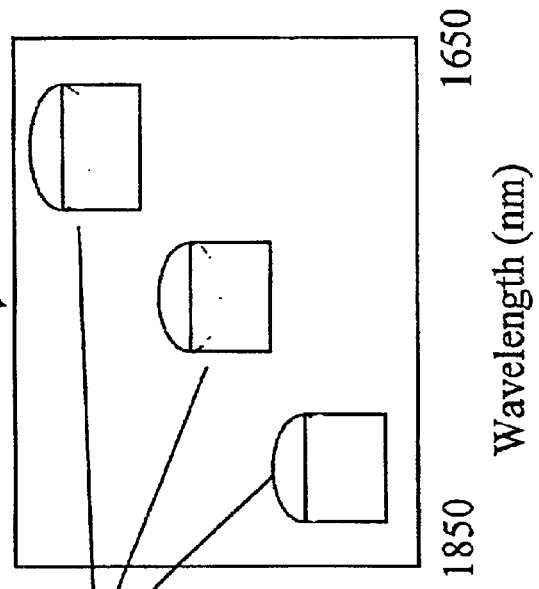
FIGS. 11A and 11B show embodiments in which the DMA is replaced with concave mirrors.
Figure 11A:
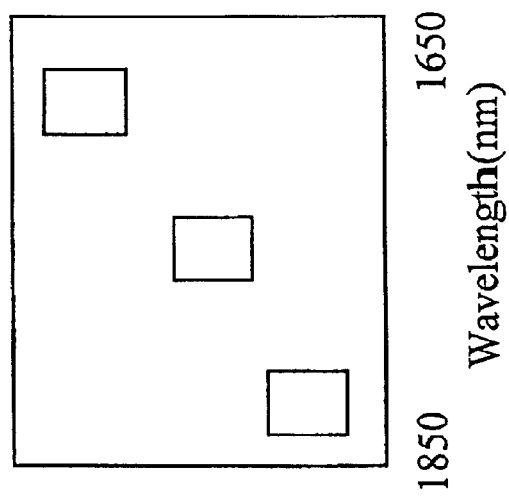

If the array of spatio/spectral resolution elements at the focal plane as shown in FIG. 6A is replaced with fixed elements, such as the concave mirrors in FIG. 11B, one can have a different device configured to perform a particular signal processing task—in this case pass the predetermined spectrum components at the desired intensity levels. FIG. 11A shows the spatio/spectral resolution elements at the focal plane to be used. The fixed optical elements are placed to interact with predetermined spatio/spectral resolution elements provided by the grating and entrance aperture geometry and to direct the specific assortment of spatio/spectral elements to specific spatial locations for modulation encoding (possibly using the barber pole arrangement, shown next).

Figure 12:
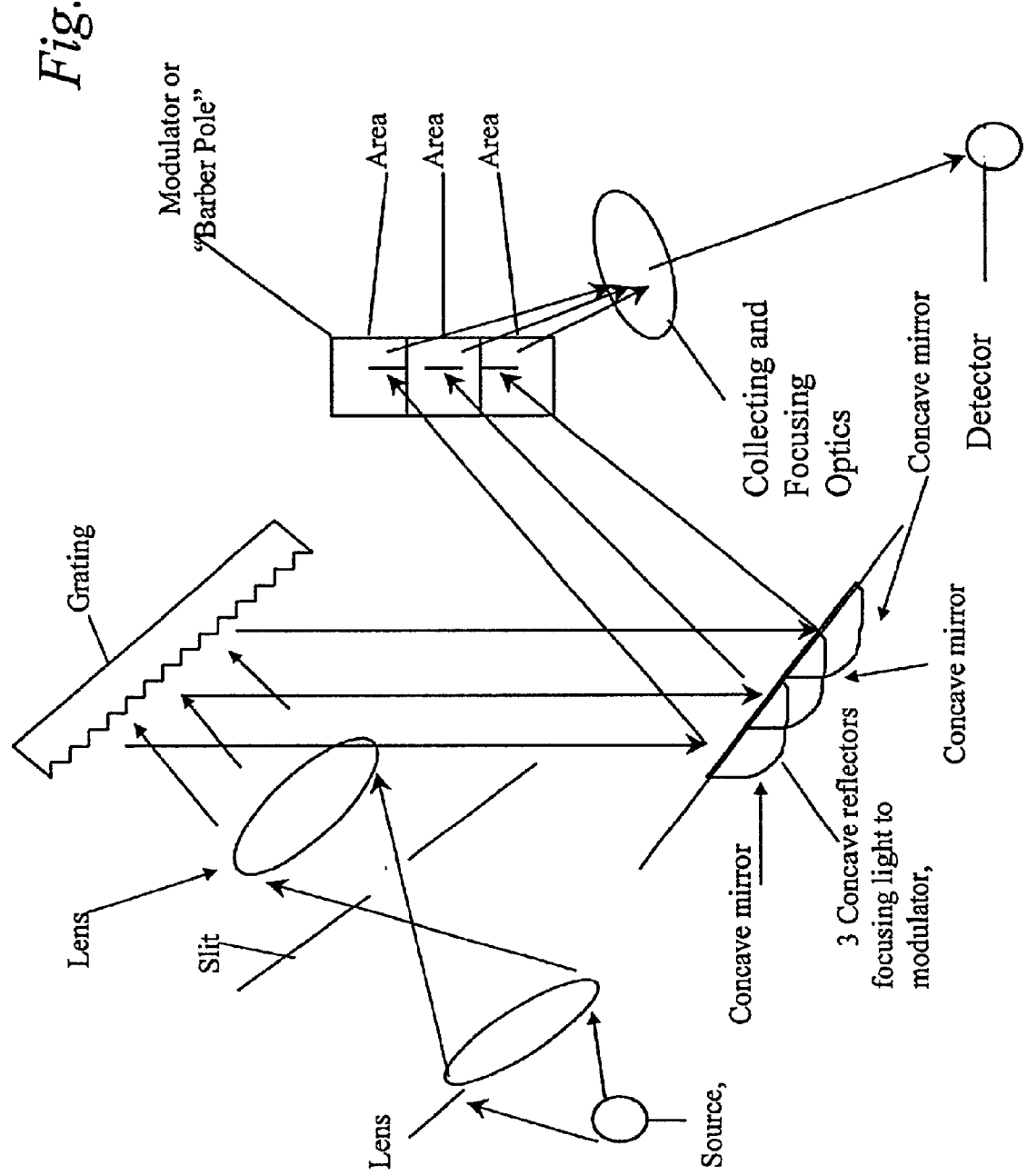
Figure 13:
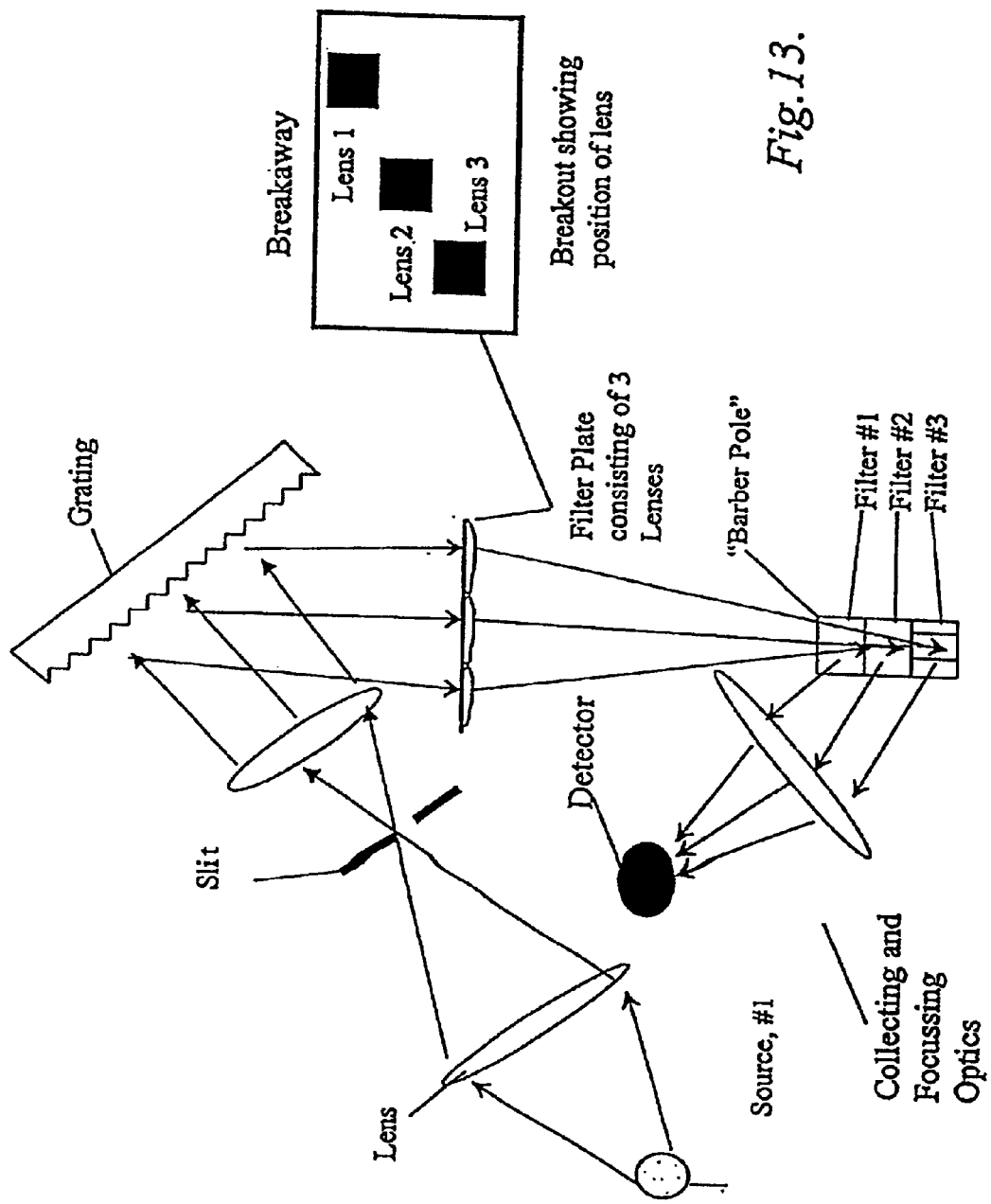

FIG. 12 illustrates an embodiment of a complete modulating spectrometer in which the DMA element is replaced by the concave mirrors of FIG. 11. FIG. 13 illustrates a modulating lens spectrometer using lenses instead of DMA, and a "barber pole" arrangement of mirrors to implement variable modulation. The "barber pole" modulation arrangement is illustrated in FIG. 14.

With reference to FIG. 14, modulation is accomplished by rotating this "barber pole" that has different number of mirrors mounted for reflecting light from the spatially separated spectral wavelengths. Thus, irradiating each vertical section will give the reflector its own distinguishable frequency. In accordance with this embodiment, light from the pole is collected and simultaneously sent to the detector. Thus, radiation from concave mirror 1 impinges upon the four-mirror modulator, concave mirror 2 radiation is modulated by the five-mirror modulator, and concave mirror 3 directs radiation to the six-mirror modulator. In the illustrated embodiment, the modulator rate is four, five, or six times per revolution of the "barber pole."

The operation of the device is clarified with reference to FIG. 12, tracing the radiation from the concave mirrors 12 to the detector of the system. In particular, concave mirror 1 reflects a selected spectral band with chosen intensity. This radiated wave impinges upon a modulator, implemented in this embodiment as a rotation barber pole. The modulating rates created by the barber pole in the exemplary embodiment shown in the figure are as shown in the table below.

| FIG. 13 | Number of mirrors Per 360° rotation | Modulation Per 360° of barber pole |
|---|---|---|
| Area A | 4 | 4/360° |
| Area B | 5 | 5/360° |
| Area C | 6 | 6/360° |

Accordingly, this arrangement yields a modulation rate of 4/360° for the radiation from Area A, FIG. 12.

By a analogy, the mirrors of Areas B and C are modulated at the rate of 5/360° and 6/360°, respectively. As illustrated, all radiation from mirrors A, B, and C is simultaneously directed to the detector. This radiation is collected by either a simple mirror lens or a toroidal mirror, which focuses the radiation onto a single detector. The signal from the detector now goes to electronic processing and mathematical analyses for spectroscopic results.

(iii) Modulating Light Sources Spectrometer.

Figures 15, 16:
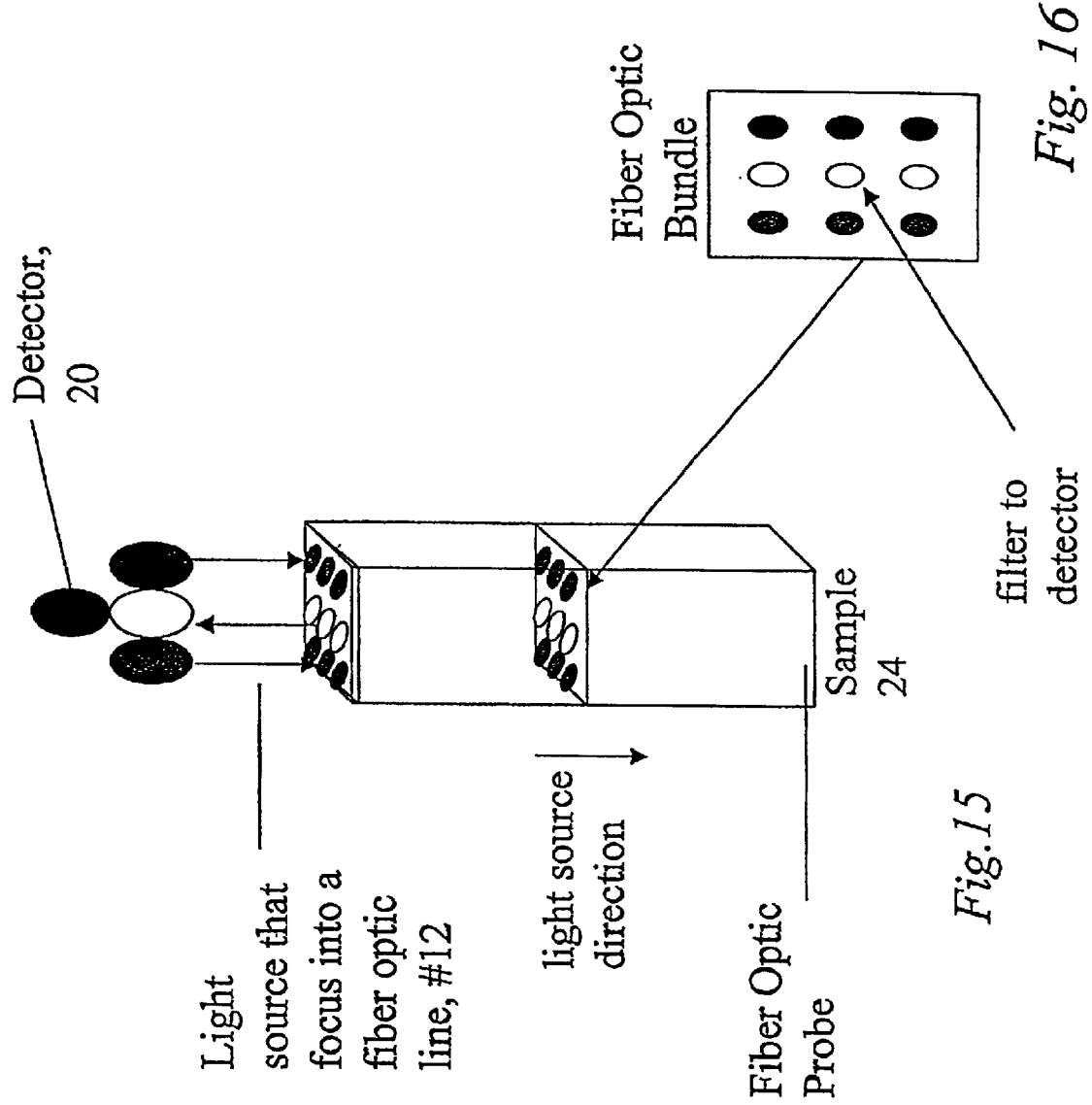
FIGS. 15 and 16 illustrate an embodiment of this invention in which one or more light sources provide several modulated spectral bands using a fiber optic bundle.

In the discussion of modulating spectrometers, a single light source of electromagnetic radiation was described. There exist yet another possibility for a unique optical design—a modulating multi-light source spectrometer. FIGS. 15 and 16 illustrate an embodiment of this invention in which a light source 12 provides several modulated spectral bands, e.g., light emitting diodes (LED), or lasers (shown here in three different light sources). The radiation from these light sources impinges upon the sample 24. One possible illumination design is one in which light from a source, e.g. LED, passes through a multitude of filters, impinging upon the sample 24. The radiation from the sample is transmitted to a detector 20, illustrated as a black fiber. The signal from the detector is electronically processed to a quantitative and qualitative signal describing the sample chemical composition.

In this embodiment, a plurality of light sources is used at differed modulating rates. FIGS. 15 and 16 illustrate the combination of several light sources in the spectrometer. The choice of several different spectral bands of electromagnetic radiation can be either light emitting diodes, LED, lasers, black body radiation and/or microwaves. Essentially the following modulation scheme can be used to identify the different light sources, in this example LED's of different spectral band wavelength.

| No. of Source | Spectral band Wavelength, nm | Modulation Rate |
|---|---|---|
| 1 | 1500–1700 | $m_1$ |
| 2 | 1600–1800 | $m_2$ |
| 3 | 1700–1900 | $m_3$ |
| . | . | . |
| . | . | . |
| . | . | . |

Note: $m_1 \neq m_2 \neq m_3 \neq \ldots$

It should be noted that either the radiation will be scattered or transmitted by the sample 24. This scattered or transmitted radiation from the sample is collected by an optical fiber. This radiation from the sample is conducted to the detector. The signal from the detector is electronically processed to yield quantitative and qualitative information about the sample.

In a particular embodiment the radiation path consists of optical fibers. However, in accordance with alternate embodiments, mirrors and lenses could also constitute the optical path for a similar modulating multi-light source spectrometer.

(iv) Modulating Multi-source Hyperspectral Imaging Spectrometer

The spectrometer described in the preceding section records spectral information about one unique area on a single detector. In a similar manner, the spectral characteristic of a multitude of areas in a sample can be recorded with a multitude of detectors in accordance with different embodiments of the invention. Such a multitude of detectors exists in an array detector. Array detectors are known in the art and include, for example Charge coupled devices (CCD), in the ultraviolet, and visible portions of the spectrum; InSb—array in near infrared; InGaAs—array in near infrared; Hg—Cd—Te—array in mid-infrared and other array detectors.

Array detectors can operate in the focal plane of the optics. Here each detector of the array detects and records the signal from a specific area, $x_i y_i$. Practical Example B in Section IV on the gray-level camera provides a further illustration. Different aspects of the embodiments discussed in sections (iii) and (iv) are considered in more detail in the following sections. As is understood by one skilled in the art, standard optical duality implies that each of the preceding configurations can be operated in reverse, exchanging the position of the source and the detector.

II. Pre-sample Processing

The preceding section described an aspect of the invention referred to as post-sample processing, i.e., signal processing performed after a sample had been irradiated. In accordance with another important aspect of this invention, significant benefits can result from irradiating a sample with pre-processed radiation, in what is referred to as pre-sample processing. Most important in this context is the use, in accordance with this invention, of one or more light sources, capable of providing modulated temporal and/or spatial patterns of input radiation. These sources are referred to next as controllable source (s) of radiation, which in general are capable of generating arbitrary combinations of spectral radiation components within a predetermined spectrum range.

Several types of prior art devices are known that are capable of providing controllable radiation. Earlier prior art devices primarily relied upon various "masking" techniques, such as electronically alterable masks interposed in the optical pathway between a light source and a detector. More recent prior art devices use a combination of two or more light-emitting diodes (LEDs) as radiation sources. Examples are provided in U.S. Pat. Nos. 5,257,086 and 5,488,474, the content of which is hereby incorporated by reference for all purposes. As discussed in the above patents, an array of LEDs or light-emitting lasers is configured for activation using a particular encoding pattern, and can be used as a controllable light source. A disadvantage of this system is that it relies on an array of different LED elements, each operating in a different, relatively narrow spectrum band. In addition, there are technological problems associated with having an array of discrete radiation elements with different characteristics.

These and other problems associated with the prior art are addressed in accordance with the present invention using a device that in a specific embodiment can be thought of as the reverse of the setup illustrated in FIG. 1A. In particular, one or more broadband radiation sources illuminate the digital micro-mirror array (DMA) 18 and the modulations of the micro-mirrors in the DMA encode the source radiation prior to impinging upon the sample. The reflected radiation is then collected from the sample and directed onto a detector for further processing.

Figure 17:
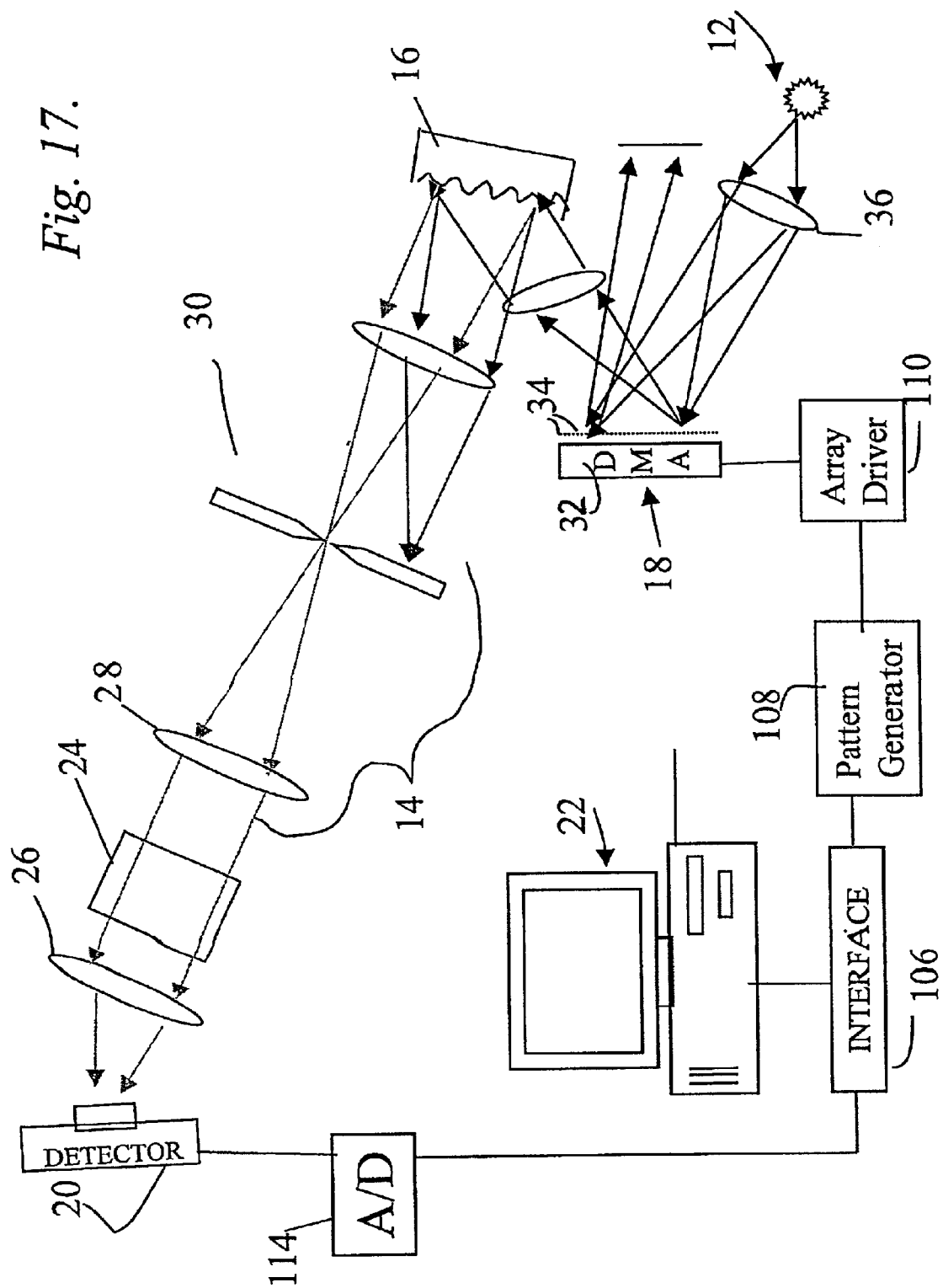
FIG. 17 illustrates in diagram form an apparatus using controllable radiation source.

FIG. 17 illustrates a schematic representation of an apparatus in accordance with the present invention using a controllable radiation source. Generally, the system includes a broadband radiation source 12, DMA 18, wavelength dispersion device 16, slit assembly 30, detector 20 and control assembly 22.

In particular, control assembly 22 may include a conventional personal computer 104, interface 106, pattern generator 108, DMA driver 110, and analog to digital (A/D) converter 114. Interface 106 operates as a protocol converter enabling communications between the computer 22 and devices 108–114.

Pattern generator 108 may include an EEPROM memory device (not shown) which stores the various encoding patterns for array 18, such as the Hadamard encoding pattern discussed below. In response to control signals from computer 22, generator 108 delivers signals representative of successive patterns to driver 110. More particularly, generator 108 produces output signals to driver 110 indicating the activation pattern of the mirrors in the DMA 18. AID converter 114 is conventional in nature and receives the voltage signals from detector 20, amplifies these signals as analog input to the converter in order to produce a digital output representative of the voltage signals.

Radiation source 12, grating 16, DMA 18 slit assembly 30 and detector 20 cooperatively define an optical pathway. Radiation from source 12 is passed through a wavelength dispersion device, which separates in space different spectrum bands. The desired radiation spectrum can them be shaped by DMA 18 using the filter arrangement outlined in Section I(B) (i). In accordance with a preferred embodiment, radiation falling on a particular micro-mirror element can also be encoded with a modulation pattern applied to it. In a specific mode of operating the device, DMA 18 is activated to reflect radiation in a successive set of encoding patterns, such as Hadamard, Fourier, wavelet or others. The resultant set of spectral components is detected by detector 20, which provides corresponding output signals. Computer 22 then processes these signals.

Computer 22 initiates an analysis by prompting pattern generator 108 to activate the successive encoding patterns. With each pattern, a set of wavelength components are resolved by grating 16 and after reflection from the DMA 18 is directed onto detector 20. Along with the activation of encoding patterns, computer 22 also takes readings from AID converter 114, by sampling data. These readings enable computer 22 to solve a conventional inverse transform, and thereby eliminate background noise from the readings for analysis.

In summary, the active light source in accordance with the present invention consists of one or more light sources, from which various spectral bands are selected for transmission, while being modulated with a temporal and/or spatial patterns. The resulting radiation is then directed at a region (or material) of interest to achieve a variety of desired tasks. A brief listing of these tasks include: (a) Very precise spectral coloring of a scene, for purposes of enhancement of display and photography; (b) Precise illumination spectrum to correspond to specific absorption lines of a compound that needs to be detected, (see FIGS. 38–42 on protein in wheat as an illustration) or for which it is desirable to have energy absorption and heating, without affecting neighboring compounds (This is the principle of the microwave oven for which the radiation is tuned to be absorbed by water molecules allowing for heating of moist food only); (c) The procedure in (b) could be used to imprint a specific spectral tag on ink or paint, for watermarking, tracking and forgery prevention, acting as a spectral bar code encryption; (d) The process of light curing to achieve selected chemical reactions is enabled by the tunable light source.

Various other applications are considered in further detail in Section IV. Duality allows one to reverse or "turn inside out" any of the post-sample processing configurations described previously, to yield a pre-sample processing configuration. Essentially, in the former case one takes post sample light, separates wavelengths, encodes or modulates each, and detects the result. The dualized version for the latter case is to take source light, separates wavelengths, encode or modulate each, interact with a sample, and detect the result.

III Optical Encoding, Decoding and Signal Processing

The preceding two sections disclosed various embodiments of systems for performing post- and pre-sample processing. In a specific embodiment, the central component of the system is a digital micro-mirror array (DMA), in which individual elements (micro-mirrors) can be controlled separately to either pass along or reject certain radiation components. By the use of appropriately selected modulation patterns, the DMA array can perform various signal processing tasks. In a accordance with a preferred embodiment of this invention, the functionality of the DMAs discussed above can be generalized using the concept of Spatial Light Modulators (SLMs), devices that broadly perform spatio-spectral encoding of individual radiation components, and of optical synapse processing units (OSPUs), basic processing blocks. This generalization is considered in subsection III.A, followed by discussions of Hadamard processing, spatio-spectral tagging, data compression, feature extraction and other signal processing tasks.

A. Basic Building Blocks (i) Spatial Light Modulators (SLMs)

In accordance with the present invention, one-dimensional (1D), two-dimensional (2D) or three dimensional (3D) devices capable of acting as a light valve or array of light valves are referred to as spatial light modulators (SLMs). More broadly, an SLM in accordance with this invention is any device capable of controlling the magnitude, power, intensity or phase of radiation or which is otherwise capable of changing the direction of propagation of such radiation. This radiation may either have passed through, or be reflected or refracted from a material sample of interest. In a preferred embodiment, an SLM is an array of elements, each one capable of controlling radiation impinging upon it. Note that in accordance with this definition an SLM placed in appropriate position along the radiation path can control either spatial or spectral components of the impinging radiation, or both. Furthermore, "light" is used here in a broad sense to encompass any portion of the electromagnetic spectrum and not just the visible spectrum. Examples of SLM's in accordance with different embodiments of the invention include liquid crystal devices, actuated micro-mirrors, actuated mirror membranes, di-electric light modulators, switchable filters and optical routing devices, as used by the optical communication and computing environments and optical switches. In a specific embodiment, Sections 1A and 1B discussed the use of a DMA as an example of spatial light modulating element. U.S. Pat. No. 5,037,173 provides examples of technology that can be used to implement SLM in accordance with this invention, and is hereby incorporated by reference.

In a preferred embodiment, a 1D, 2D, or 3D SLM is configured to receive any set of radiation components and functions to selectively pass these components to any number of receivers or image planes or collection optics, as the application may require, or to reject, reflect or absorb any input radiation component, so that either it is or is not received by one or more receivers, image planes or collection optics devices. It should be clear that while in the example discussed in Section I above the SLM is implemented as a DMA, virtually any array of switched elements may be used in accordance with the present invention.

Generally, an SLM in accordance with the invention is capable of receiving any number of radiation components, which are then encoded, tagged, identified, modulated or otherwise changed in terms of direction and/or magnitude to provide a unique encodement, tag, identifier or modulation sequence for each radiation component in the set of radiation components, so that subsequent optical receiver (s) or measuring device (s) have the ability to uniquely identify each of the input radiation components and its properties. In a relevant context, such properties include, but are not limited to, irradiance, wavelength, band of frequencies, intensity, power, phase and/or polarization. In Sections I and II above, tagging of individual radiation components is accomplished using rate modulation. Thus, in Section I, different spectral components of the input radiation that have been separated in space using a wavelength dispersion device are then individually encoded by modulating the micro-mirrors of the DMA array at different rates. The encoded radiation components are directed to a single detector, but nevertheless can be analyzed individually using Fourier analysis of the signal from the detector. Other examples for the use of "tagging" are discussed below.

(ii) The Optical Synapse Processing Unit (OSPU)

In accordance with this invention, various processing modalities can be realized with an array of digitally controlled switches (an optical synapse), which function to process and transmit signals between different components of the system. In the context of the above description, the basic OSPU can be thought of as a data acquisition unit capable of scanning an array of data, such as an image, in various modes, including raster, Hadamard, multiscale wavelets, and others, and transmitting the scanned data for further processing. Thus, a synapse is a digitally controlled array of switches used to redirect image (or generally data) components or combinations of light streams, from one location to one or more other locations. In particular it can perform Hadamard processing, as defined below, on a plurality of radiation elements by combining subsets of the elements (i.e., binning) before conversion to digital data. A synapse can be used to modulate light streams by modulating temporally the switches to impose a temporal bar code (by varying in time the binning operation). This can be built in a preferred embodiment from a DMA, or any of a number of optical switching or routing components, used for example in optical communications applications.

An OSPU unit in accordance with the present invention is shown in diagram form in FIG. 18A and 18B, as three-port device taking input from a radiation source S, and distributing it along any of two other paths, designated C (short for camera) and D (for detector). Different scanning modes of the OSPU are considered in more detail in Section III.B. below.

In the above disclosure and in one preferred embodiment of the invention an OSPU is implemented using a DMA, where individual elements of the array are controlled digitally to achieve a variety of processing tasks while collecting data. In accordance with the present invention, information bearing radiation sources could be, for example, a stream of photons, a photonic wavefront, a sound wave signal, an electrical signal, a signal propagating via an electric field or a magnetic field, a stream of particles, or a digital signal. Example of devices that can act as a synapse include spatial light modulators, such as LCDs, MEMS mirror arrays, or MEMS shutter arrays; optical switches; optical add-drop multiplexers; optical routers; and similar devices configured to modulate, switch or route signals. Clearly, DMAs and other optical routing devices, as used by the optical communication industry can be used to this end. It should be apparent that liquid crystal displays (LCD), charge coupled devices (CCD), CMOS logic, arrays of microphones, acoustic transducers, or antenna elements for electromagnetic radiation and other elements with similar functionality that will be developed in the future, can also be driven by similar methods.

Applicants' contribution in this regard is in the novel process of performing pre-transduction digital computing on analog data via adaptive binning means. Such novelty can be performed in a large number of ways. For example, one can implement adaptive current addition using a parallel/serial switch and wire networks in CMOS circuits. Further, in the acoustic processing domain, one or more microphones can be used in combination with an array of adjustable tilting sound reflectors (like a DMD for sound). In each case, one can "bin" data prior to transduction, in an adaptive way, and hence measure some desired computational result that would traditionally be obtained by gathering a "data cube" of data, and subsequently digitally processing the data. The shift of paradigm is clear: in the prior art traditionally analog signals are captured by a sensor, digitized, stored in a computer as a "data cube", and then processed. Considerable storage space and computational requirements are extended to do this processing. In accordance with the present invention, data from one or more sensors is processed directly in the analogue domain, the processed result is digitized and sent to a computer, where the desired processing result may be available directly, or following reduced set of processing operations.

In accordance with the present invention, the digitally controlled array is used as a hybrid computer, which through the digital control of the array elements performs (analog) computation of inner products or more generally of various correlations between data points reaching the elements of the array and prescribed patterns. The digital control at a given point (i.e., element) of the array may be achieved through a variety of different mechanisms, such as applying voltage differences between the row and column intersecting at the element; the modulation is achieved by addressing each row and column of the array by an appropriately modulated voltage pattern. For example, when using DMA, the mirrors are fluctuating between two tilted positions, and modulation is achieved through the mirror controls, as known in the art. The specifics of providing to the array element of signal (s) following a predetermined pattern will depend on the design implementation of the array and are not considered in further detail. Broadly, the OSPU array is processing raw data to extract desired information.

In accordance with the present invention, various assemblies of OSPU along with other components can be used to generalize the ideas presented above and enable new processing modalities. For example, FIG. 19 illustrates in block diagram form the design of a spectrograph using OSPU. As shown, the basic design brings reflected or transmitted radiation from a line in the sample or source onto a dispersing device 16, such as a grating or prism, onto the imaging fiber into the OSPU to encode and then forward to a detector 20.

Figure 20:
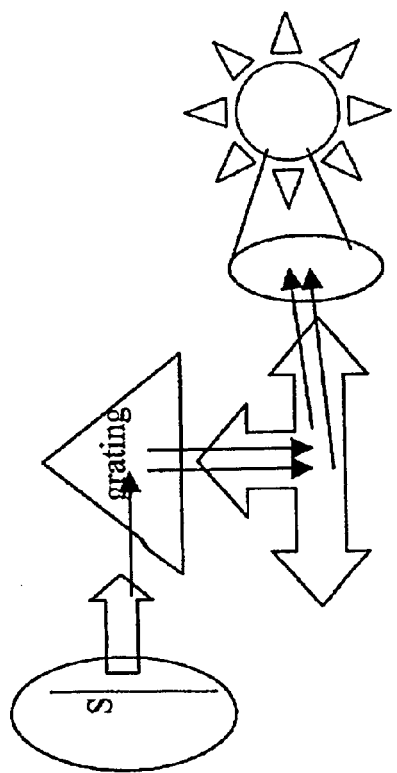
FIG. 20 illustrates in a diagram form an embodiment of a tunable light source.

FIG. 20 illustrates in a diagram form an embodiment of a tunable light source, which operates as the spectrograph in FIG. 19, but uses a broadband source. In this case, the switching elements of the OSPU array, for example the mirrors in a DMA, are set to provide a specified energy in each row of the mirror, which is sent to one of the outgoing imaging fiber bundles. This device can also function as a spectrograph through the other end, i.e., fiber bundle providing illumination, as well as spectroscopy.

Figure 21:
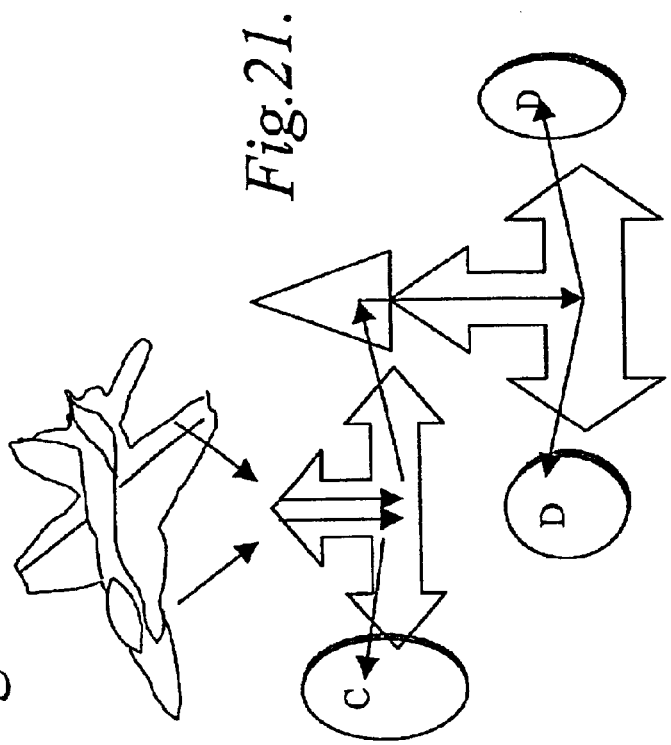
FIG. 21 illustrates in a diagram form an embodiment of the spectral imaging device, which is built using two OSPUs.
Figure 22:
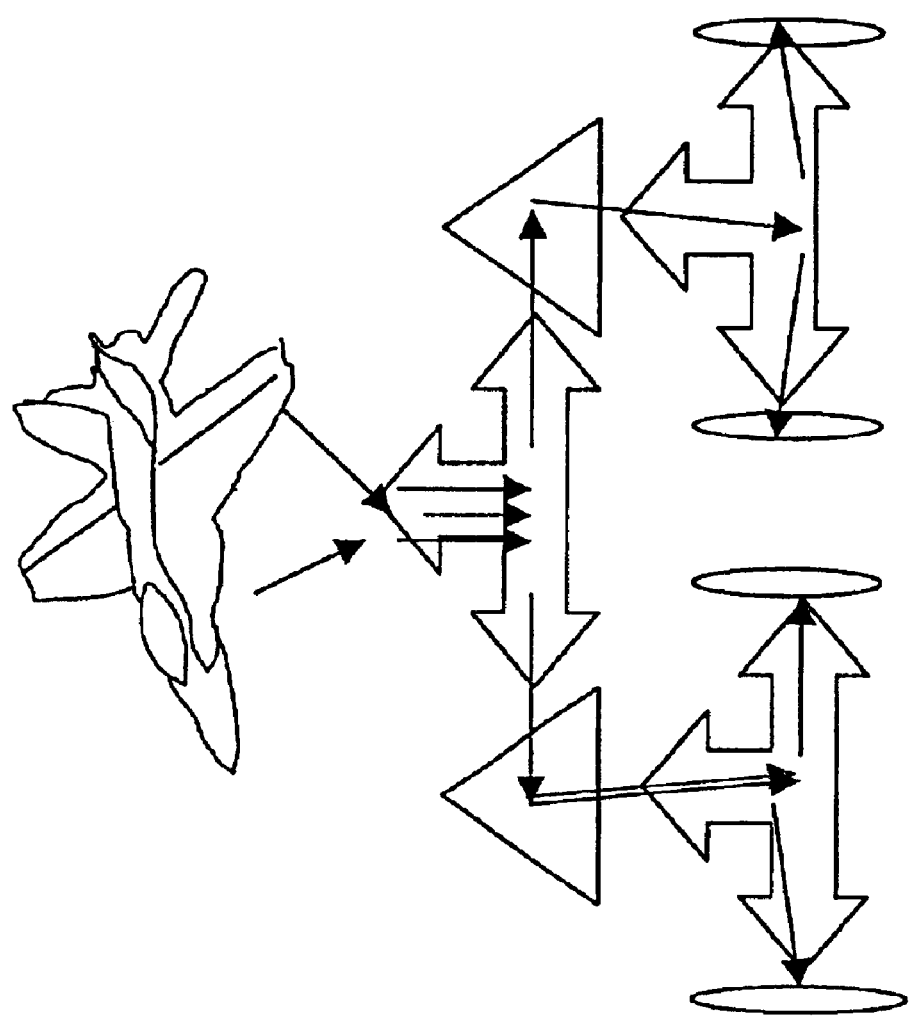
FIGS. 22 and 23 illustrate different devices built using OSPUs.
Figure 23:
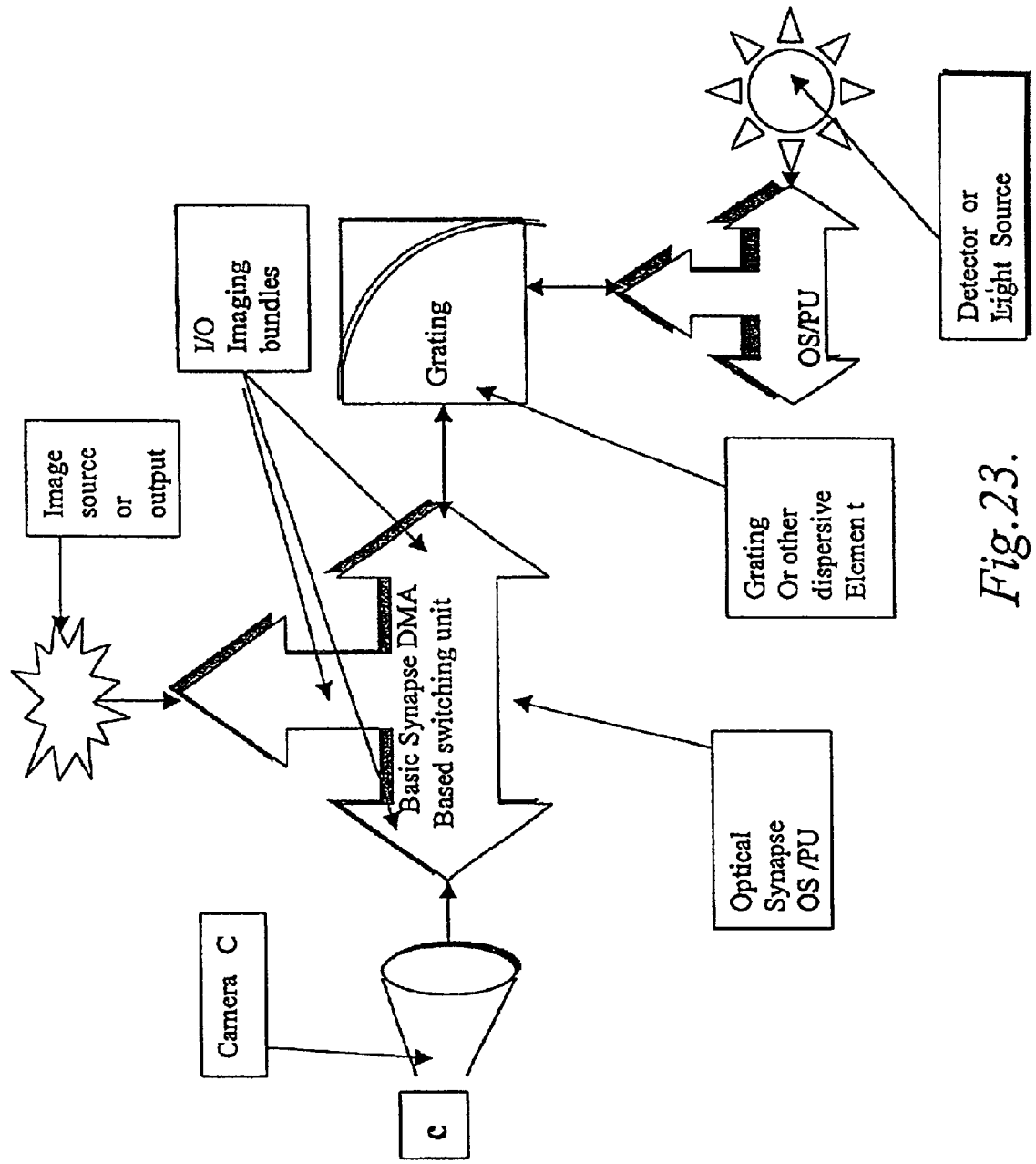

FIG. 21 illustrates in a diagram form an embodiment of the spectral imaging device discussed in Section I above, which is built with two OSPUs. Different configurations of generalized processing devices are illustrated in FIG. 22, in which each side is imaging in a different spectral band, and FIG. 23, which illustrates the main components of a system for processing input radiation using an OSPU.

B. Scanning an Area of Interest

Figure 24:
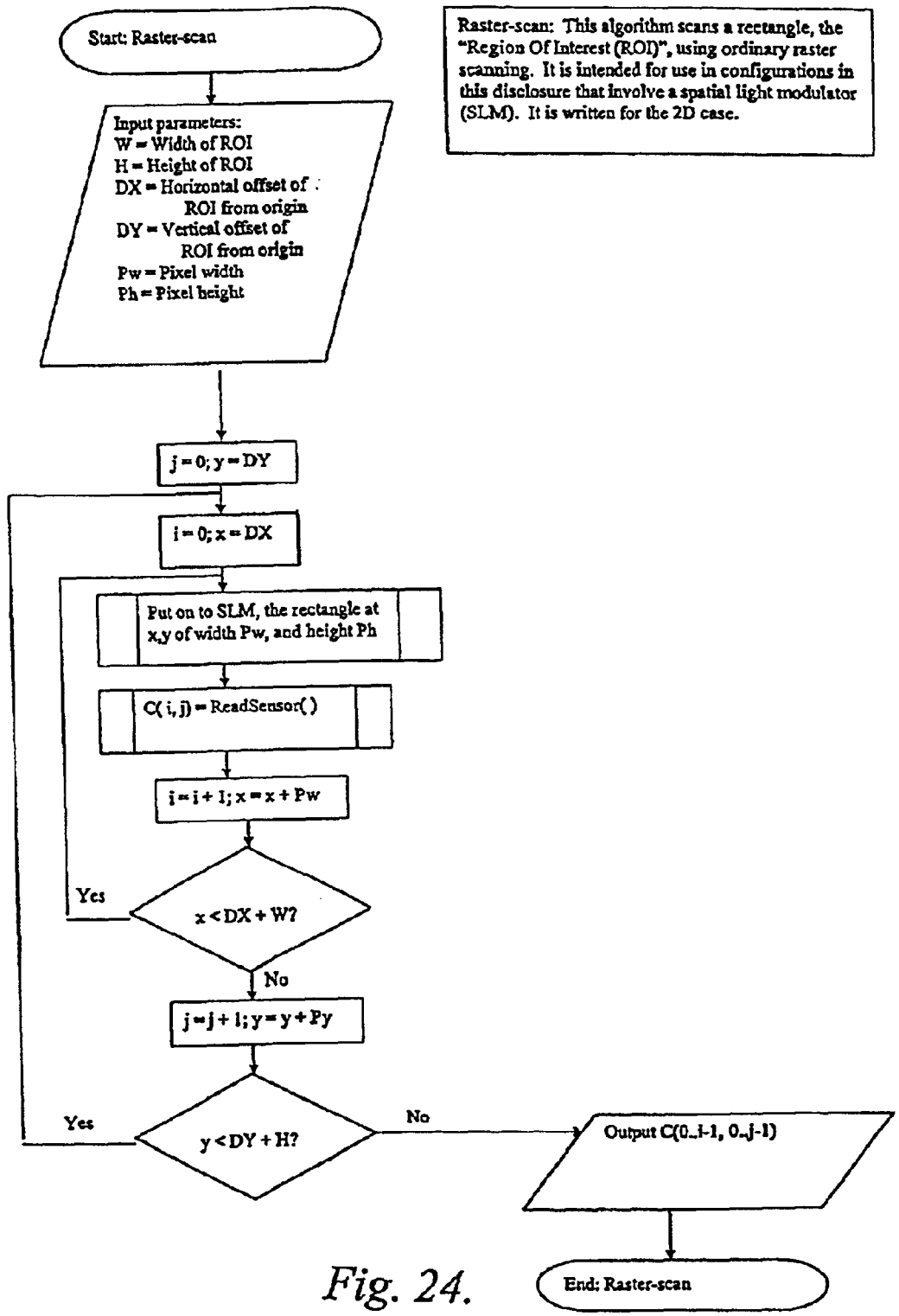
FIGS. 24–26 are flow charts of various scans used in accordance with the present invention. Specifically.
Figure 25:
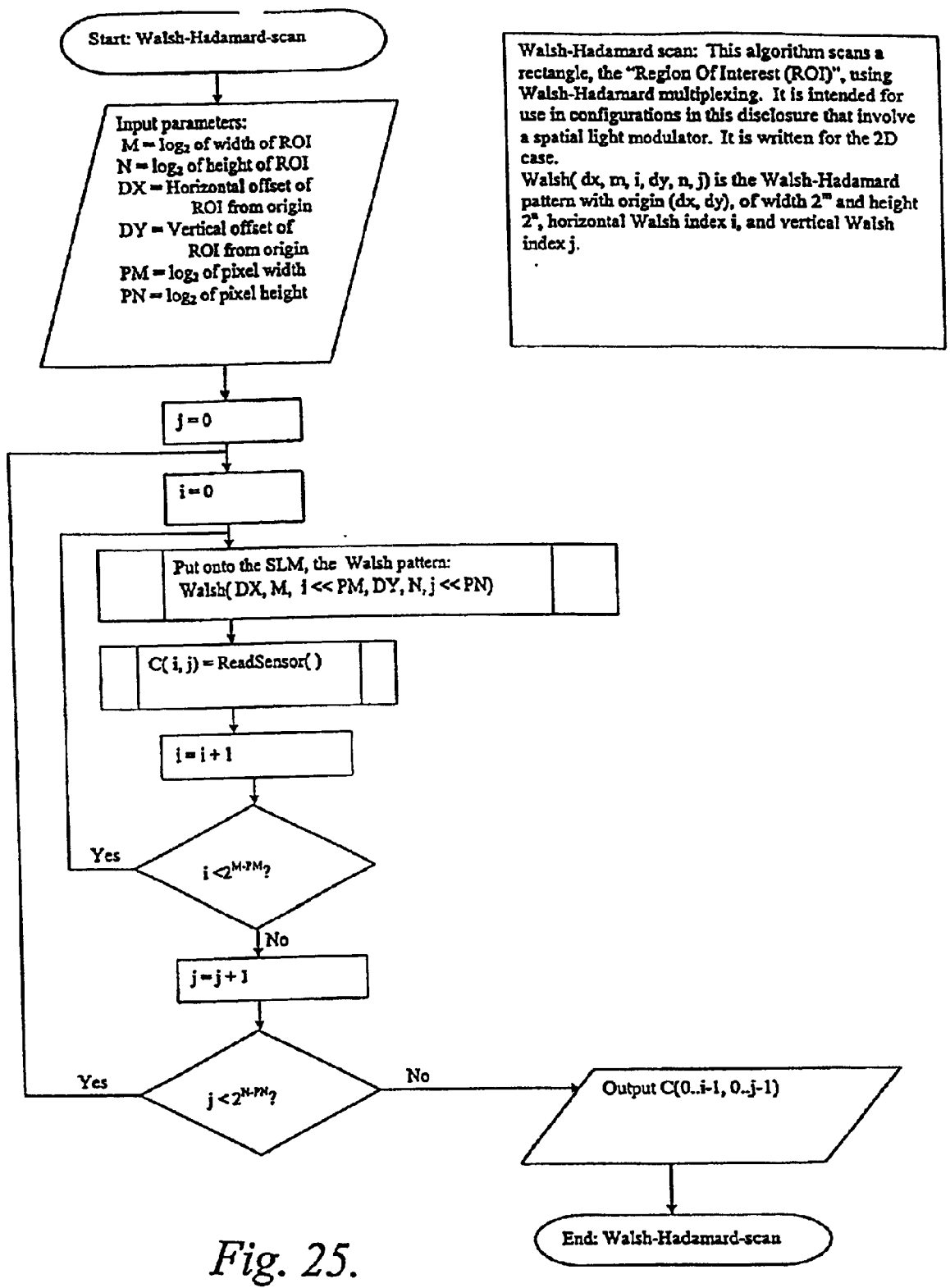
Figure 26:
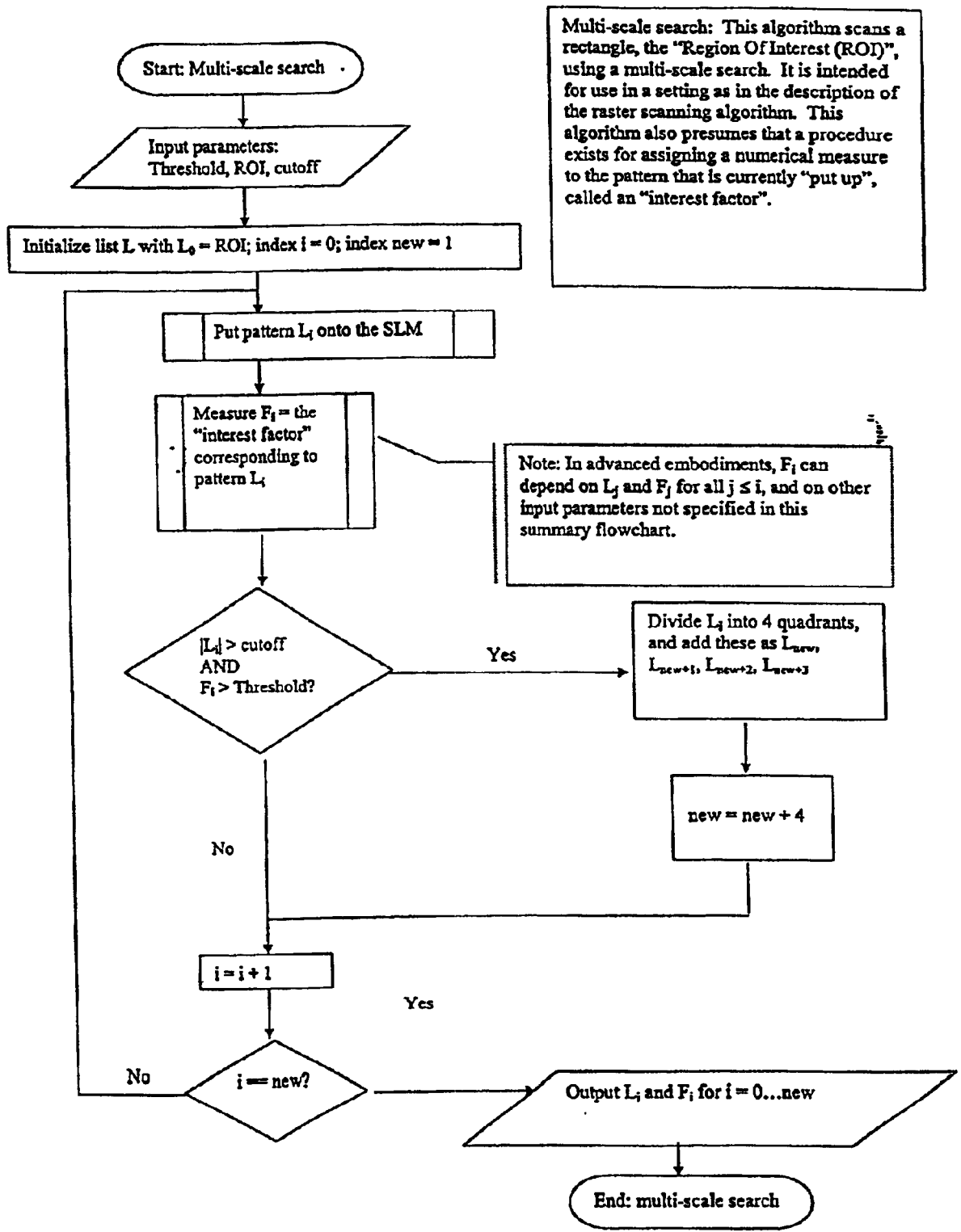

In accordance with the present invention, different scanning modes can be used in different applications, as illustrated in FIG. 24, FIG. 25 and FIG. 26. These algorithms are of use, for example, when one is using an OSPU in conjunction with a single sensor, and the OSPU is binning energy into that sensor, the binning being determined by the pattern that is put onto the SLM of the OSPU.

In particular, FIG. 24 is a flow chart of a raster-scan using in one embodiment of the present invention. This algorithm scans a rectangle, the "Region Of Interest (ROI)," using ordinary raster scanning. It is intended for use in configurations in this disclosure that involve a spatial light modulator (SLM). It is written for the 2D case, but the obvious modifications will extend the algorithm to other dimensions, or restrict to 1D.

FIG. 25 is a flowchart of a Walsh-Hadamard scan used in accordance with another embodiment of the invention. This algorithm scans a rectangle, the "Region Of Interest (ROI)", using Walsh-Hadamard multiplexing. Walsh (dx, m, i, dy, n, j) is the Walsh-Hadamard pattern with origin (dx, dy), of width $2^m$ and height $2^n$, horizontal Walsh index i, and vertical Walsh index j.

FIG. 26 is a flowchart of a multi-scale scan. This algorithm scans a rectangle, the "Region Of Interest (ROI)", using a multi-scale search. It is intended for use in a setting as in the description of the raster scanning algorithm. The algorithm also presumes that a procedure exists for assigning a numerical measure to the pattern that is currently on is called an "interest factor."

Figure 26A:
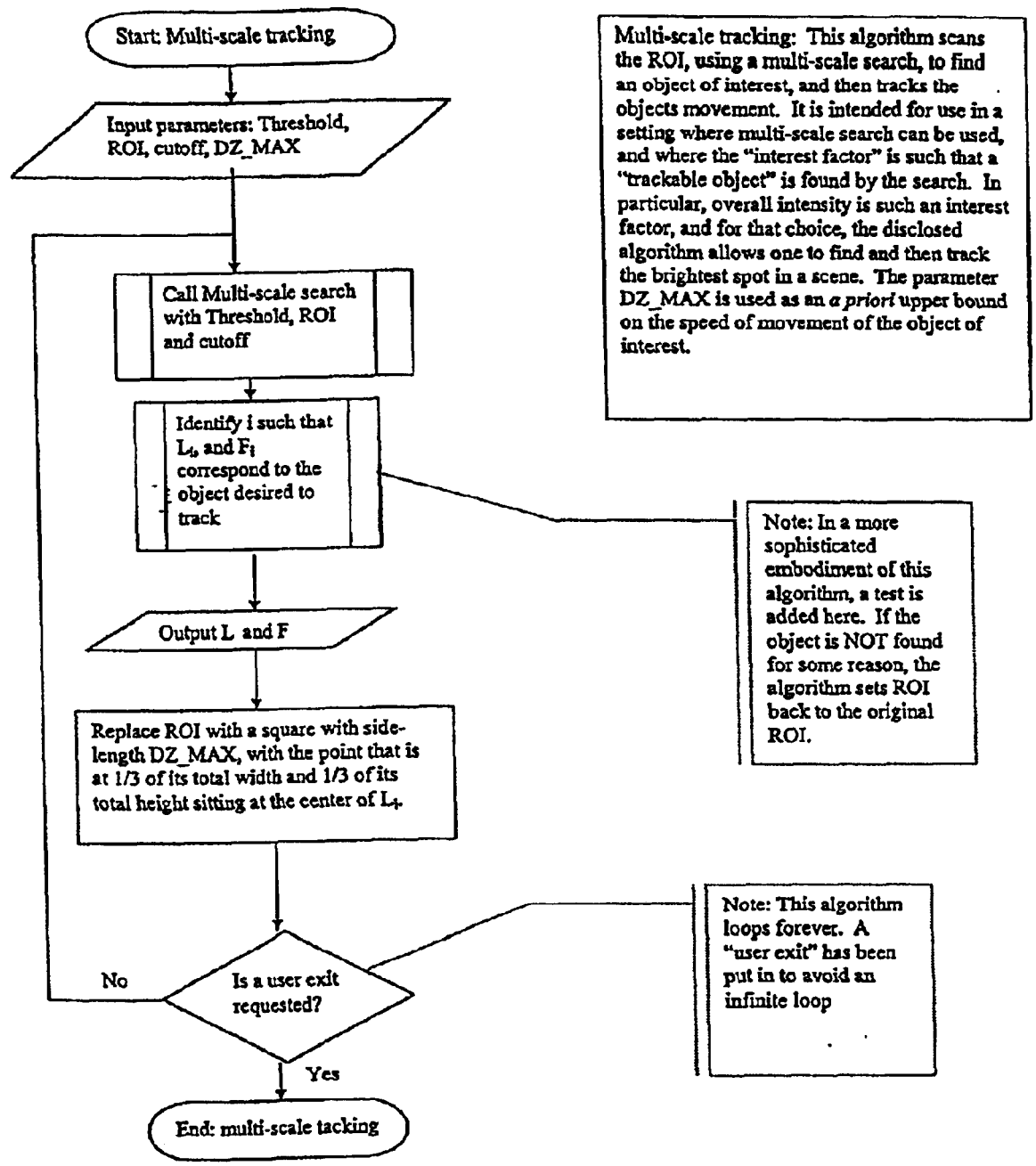
FIG. 26A illustrates a multi-scale tracking algorithm in a preferred embodiment of the present invention.

FIG. 26A illustrates a multi-scale tracking algorithm in a preferred embodiment of the present invention. The algorithm scans the region of interest, (using multi-scan search), to find an object of interest and then tracks the object's movement across the scene. It is intended for use in a setting where multi-scale search can be used, and where the "interest factor" is such that a trackable object can be found. Examples of interest factors used in accordance with a preferred embodiment (when pattern $L_i$ is put onto the SLM, the sensor reads $C_i$ and we are defining the "interest factor" $F_i$). In the preceding scan algorithms a single sensor is assumed. Thus 1. $F(L_i)=C_i$
2. $F(L_i)=C_i/\text{area}(L_i)$
3. $F(L_i)=C_i/C_k$, where $L_k$ is the rectangle that contains $L_i$, and that has N times the area of $L_i$, (for example, N=4), and which has already been scanned by the algorithm (there will always be exactly one such).

A modification of the algorithm is possible, where instead of putting up the pattern $L_i$, one can put up a set of a few highly oscillatory Walsh patterns fully supported on exactly $L_i$, and take the mean value of the sensor reading as $F_i$. This estimates the total variation within $L_i$ and will yield an algorithm that finds the edges within a scene. In different $L_i$ examples the sensor is a spectrometer. $F(L_i)$=distance between the spectrum read by the sensor, and the spectrum of a compound of interest. (distance could be, e.g., Euclidean distance of some other standard distance). This will cause the algorithm to zoom in on a substance of interest.

In another embodiment, F ($L_i$)=distance between the spectrum read by the sensor, and the spectrum already read for $L_k$, where $L_k$ is the rectangle that contains $L_i$, and that has N (N=4) times the area of $L_i$, and which has already bee scanned by the algorithm (there will always be exactly one such). This will cause the algorithm to zoom in on edges between distinct substances.

In yet another embodiment, F ($L_i$=distance between the spectrum read by the sensor, and the spectrum already read for $L_O$. This will cause the algorithm to zoom in on substances that are anomalous compared to the background.

In derived embodiments, F ($L_i$) can depend on a priori data from spectral or spatio-spectral libraries.

By defining the interest factor appropriately, one can thus cover a range of different applications. In a preferred embodiment, the interest factor definitions can be pre-stored so a user can analyze a set of data using different interest factors.

It is also clear that, in the case of Walsh functions, because of the multi-scale nature of the Walsh patterns, one can combine raster and Walsh-Hadamard scanning (raster scanning at large scales, and using Walsh-Hadamard to get extra signal to noise ratio at fine scales, where it is needed most). This allows one to operate within the linear range of the detector.

Also, one can used the combined raster/Walsh idea in variations of the Multi-scale search and tracking algorithms. For this, whenever one is studying the values of a sensor associated with the sub-rectangles of a bigger rectangle, one could use the Walsh patterns at the relevant scale, instead of scanning the pixels at that scale. This will provide for an improvement in SNR. One could again do this only at finer scales, to stay in the detectors linearity range.

C. Hadamard and Generalized Hyperspectral Processing

Several signal processing tasks, such as filtering, signal enhancement, feature extraction, data compression and others can be implemented efficiently by using the basic ideas underlying the present invention. The concept is first illustrated in the context of one-dimensional arrays for Hadamard spectroscopy and is then extended to hyperspectral imaging and various active illumination modes. The interested reader is directed to the book "Hadamard Transform Optics" by Martin Harwit, et al., published by Academic Press in 1979, which provides an excellent overview of the applied mathematical theory and the degree to which common optical components can be used in Hadamard spectroscopy and imaging applications.

Hadamard processing refers generally to analysis tools in which a signal is processed by correlating it with strings of 0 and 1 (or +/-1). Such processing does not require the signal to be converted from analogue to digital, but permits direct processing on the analog data by means of an array of switches (synapse). In a preferred embodiment of the invention, an array of switches, such as a DMA, is used to provide spatio-spectral tags to different radiation components. In alternative embodiments it can also be used to impinge spatio/spectral signatures, which directly correlate to desired features.

A simple way to explain Hadamard spectroscopy is to consider the example of the weighing schemes for a chemical scale. Assume that we need to weigh eight objects, $x_1$, $x_2 \ldots x_8$, on a scale. One could weigh each object separately in a process analogous to performing a raster scan, or balance two groups of four objects. Selecting the second approach, assuming that the first four objects are in one group, and the second four in a second group, balancing the two groups can be represented mathematically using the expression:

$$m = x_1 + x_2 + x_3 + x_4 - (x_5 + x_6 + x_7 + x_8) = (x, w),$$

where x is a vector, the components of which correspond to the ordered objects $xi_i = (1,1,1,1,-1,-1,-1,-1)$ and (x, w) designates the inner product of the two vectors. Various other combinations of object groups can be obtained and mathematically expressed as the inner product of the vector x and a vector of weights w, which has four $30$ 1 and four −1 elements.

For example, w=(1, −1, 1, 1, −1, −1, 1, −1) indicates that $x_1, x_3, x_4, x_7$ are on the left scale while $x_2, x_5, x_6, x_8$ are on the right. The inner product, or weight M=(x, w) is given by the expression:

$$m = (x, w) = x_1 - x_2 + x_3 + x_4 - x_5 - x_6 + x_7 - x_8$$

It is well known that if one picks eight mutually orthogonal vectors $w_i$ which correspond, for example, to the eight Walsh patterns, one can recover the weight $x_i$ of each object via the orthogonal expansion method $$x = [(x, w_1)w_1 + (x, w_2)w_2 + \ldots + (x, w_8)w_8],$$

or in matrix notation $$[W]x = m; \quad x = [W]^{-1}m$$

where [W] is the matrix of orthogonal vectors, m is the vector of measurements, and $[W]^{-1}$ is the inverse of matrix [W].

It is well known that the advantage of using the method is its higher-accuracy, more precisely if the error for weighing measurement is $\epsilon$, the expected error for the result calculated from the combined measurements is reduced by the square root of the number of samples. This result was proved by Hotteling to provide the best reduction possible for a given number of measurements.

Figure 27:
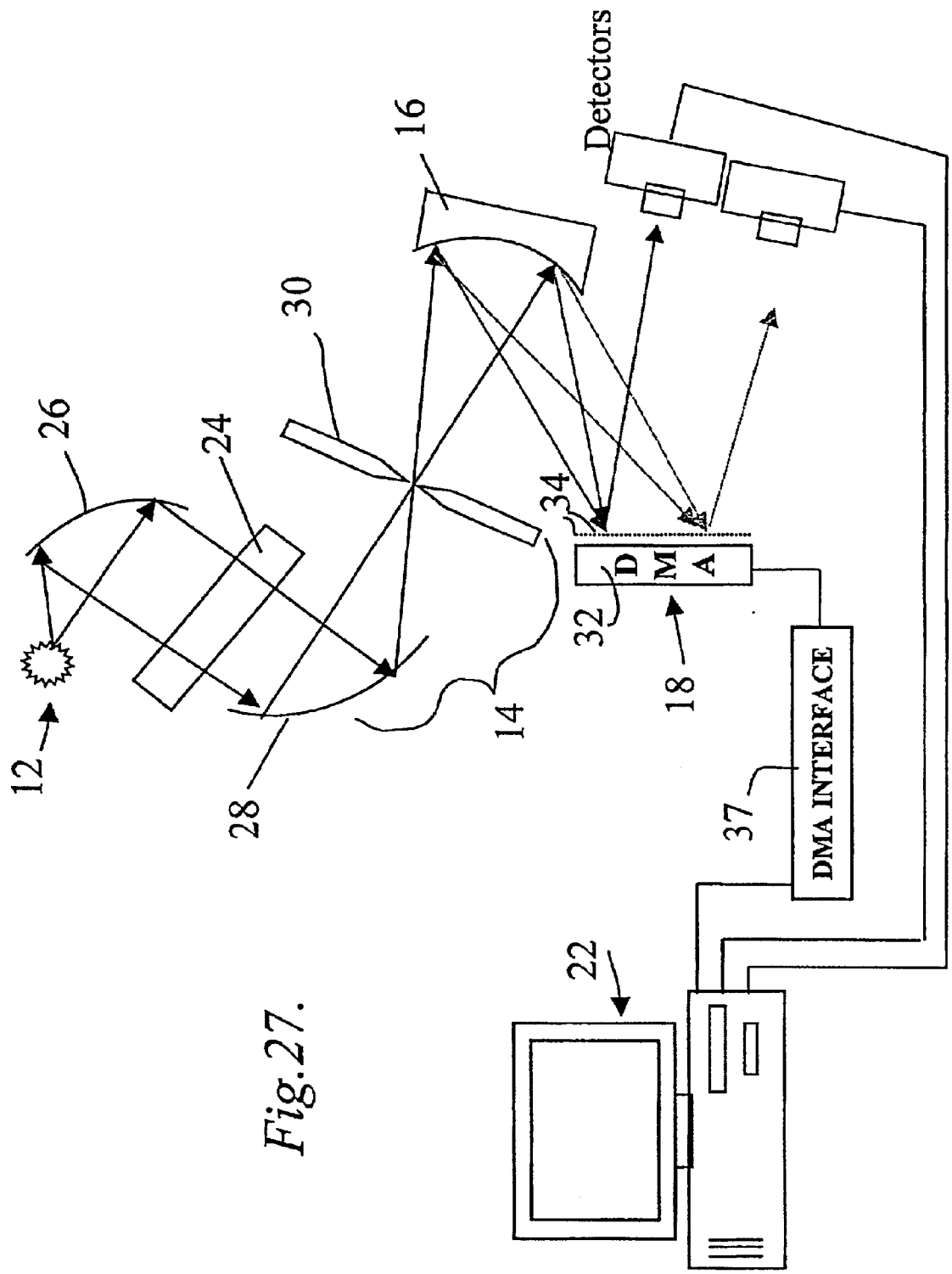
FIG. 27 is a block diagram of a spectrometer with two detectors.

In accordance with the present invention, this signal processing technique finds simple and effective practical application in spectroscopy, if we consider a spectrometer with two detectors (replacing the two arms of the scales). With reference to FIG. 27, the diffraction grating sends different spectral lines into an eight mirror array, which redistributes the energy to the 2 detectors in accordance with a given pattern of +1/−1 weights, i.e., $w_i = (1,-1,1,1,-1,-1,1,-1)$. Following the above analogy, the difference between the output values of the detectors corresponds to the inner product m=(x,$w_i$). If one is to redistribute the input spectrum energy to the 2 spectrometers using eight orthogonal vectors of weights, (following the pattern by alternating the mirror patterns to get eight orthogonal configurations), an accurate measurement of the source spectrum can be obtained. This processing method has certain advantages to the raster scan in which the detector measures one band at a time.

Clearly, for practical applications a precision requiring hundreds of bands may be required to obtain accurate chemical discrimination. However, it should be apparent that if one knows in advance which bands are needed to discriminate two compounds, the turning of the mirrors to only detect these bands could provide such discrimination with a single measurement.

Following is a description of a method for selecting efficient mirror settings to achieve discrimination using a minimum number of measurements. In matrix terminology, the task is to determine a minimum set of orthogonal vectors.

In accordance with the present invention, to this end one can use the Walsh-Hadamard Wavelet packets library. As known, these are rich collections of ±1, 0 patterns which will be used as elementary analysis patterns for discrimination. They are generated recursively as follows: (a) first, double the size of the pattern w in two ways either as (w,w) or as (w,−w). It is clear that if various n patterns wi of length n are orthogonal, then the 2n patterns of length 2n are also orthogonal. This is the simplest way to generate Hadamard-Walsh matrices.

Figure 28:
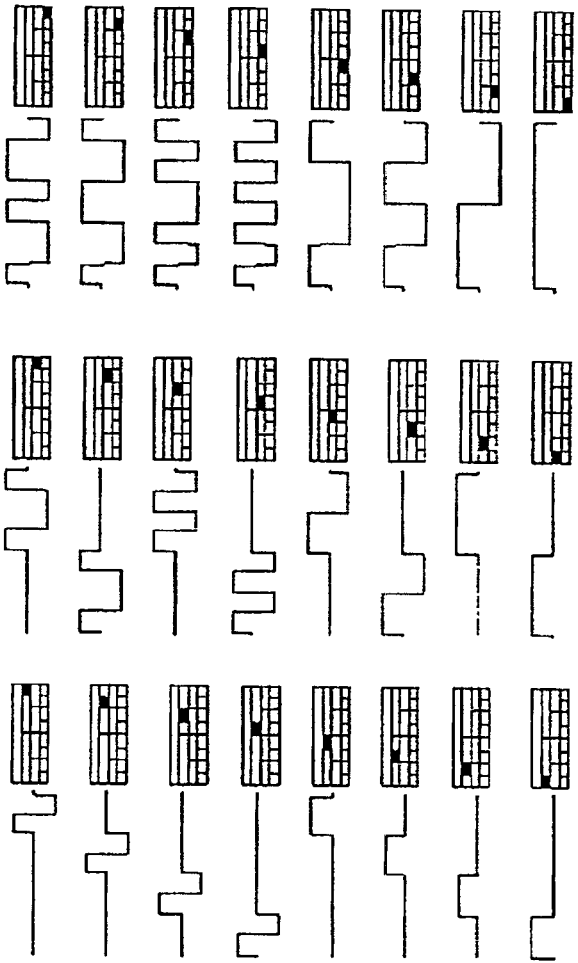
FIG. 28 illustrates a Walsh packet library of patterns for N=8.

The wavelet packet library consists of all sequences of length N having broken up in $2^m$ blocks, all except one are 0 and one block is filled with a Walsh pattern (of ±1) of length $2^l$ where l+m=n. As known, a Walsh packet is a localized Walsh string of ±1. FIG. 28 illustrates all 24 library elements for N=8.

A correlation of a vector x with a Walsh packet measures a variability of x at the location where the packet oscillates. The Walsh packet library is a simple and computationally efficient analytic tool allowing sophisticated discrimination with simple binary operations. It can be noted that in fact, it is precisely the analog of the windowed Fourier transform for binary arithmetic.

As an illustration, imagine two compounds A and B with subtle differences in their spectrum. The task is to discriminate among them in a noisy environment and design efficient mirror configurations for DMA spectroscope. In accordance with a preferred embodiment, the following procedure can be used:

(1) Collect samples for both A and B, the number of samples collected should be representative of the inherent variability of the measurements. A sample in this context is a full set x of the spectrum of the compound.

(2) Compute the inner product (x, w) for all samples X of A and (y, w) for all samples Y of B for each fixed Walsh product w.

(3) Measure the discrimination power pw of the pattern w to distinguish between compound A and B. This could be done by comparing the distribution of the numbers {(x·w)} to the distribution of the numbers {(y, w)}, where the farther apart these distributions, the better they can be distinguished..

(4) Select an orthogonal basis of patterns w maximizing the total discrimination power and order them in decreasing order.

(5) Pick the top few patterns as an input to a multidimensional discrimination method.

As an additional optional step in the above procedure, experiments can be ran using data on which to top few selected patterns failed, and repeat steps 3, 4 and 5.

Because of the recursive structure of the W-packet library, it is possible to achieve 2+3+4 in Nlog2 N computations per sample vector of length N, i.e. essentially at the rate data collection. It should be noted that this procedure of basis selection for discrimination can also be used to enhance a variety of other signal processing tasks, such as data compression, empirical regression and prediction, adaptive filter design and others. It allows to define a simple orthogonal transform into more useful representations of the raw data. Further examples are considered below and illustrated in Section IV in the wheat protein example.

In this Section we considered the use of Hadamard processing to provide simple, computationally efficient and robust signal processing. In accordance with the present invention, the concept of using multiple sensors and/or detectors can be generalized to what is known as hyperspectral processing.

As known, current spectroscopic devices can be defined broadly into two categories—point spectroscopy and hyperspectral imaging. Point spectroscopy in general involves a single sensor measuring the electromagnetic spectrum of a single sample (spatial point). This measurement is repeated to provide a point-by-point scan of a scene of interest. In contrast, hyperspectral imaging generally uses an array of sensors and associated detectors. Each sensor corresponds to the pixel locations of an image and measures a multitude of spectral bands. The objective of this imaging is to obtain a sequence of images, one for each spectral band. At present, true hyperspectral imaging devices, having the ability to collect and process the full combination of spectral and spatial data are not really practical as they require significant storage space and computational power.

Figure 29:
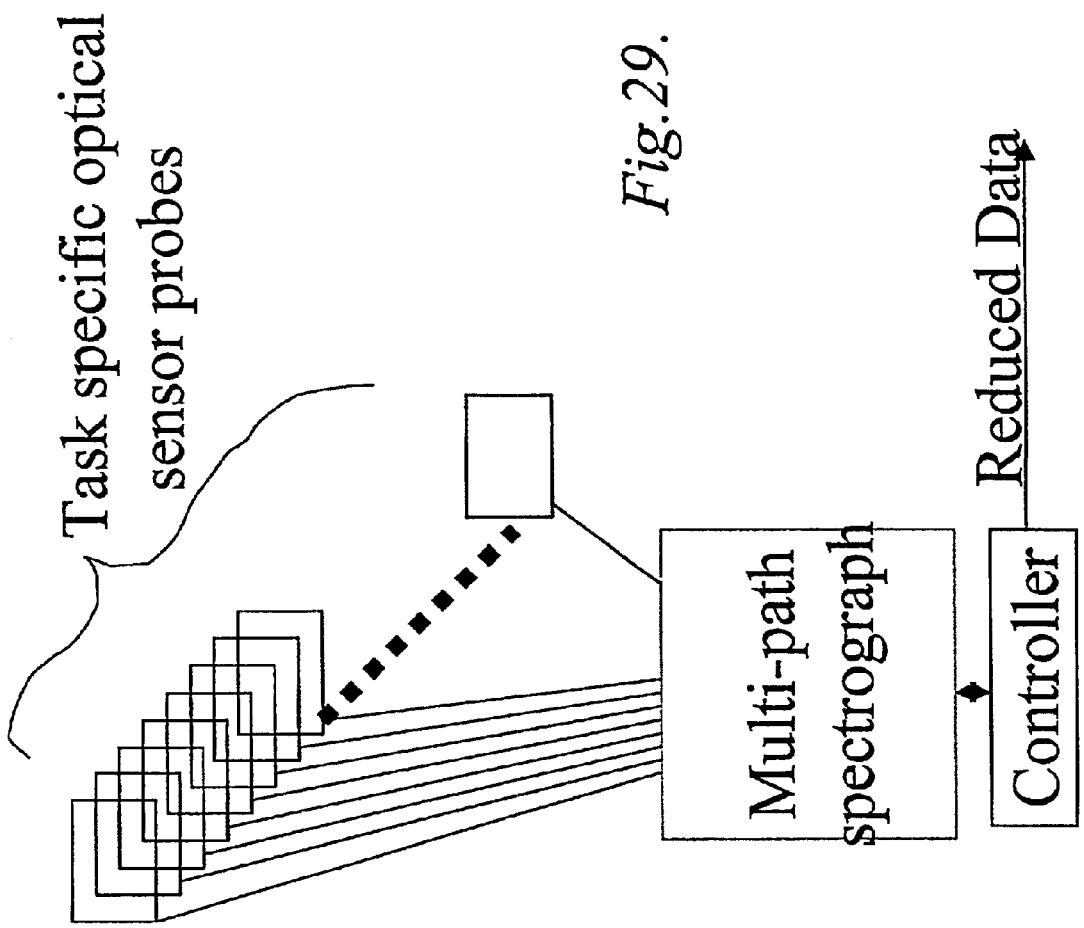
FIG. 29 is a generalized block diagram of hyperspectral processing in accordance with the invention.
Figure 30:
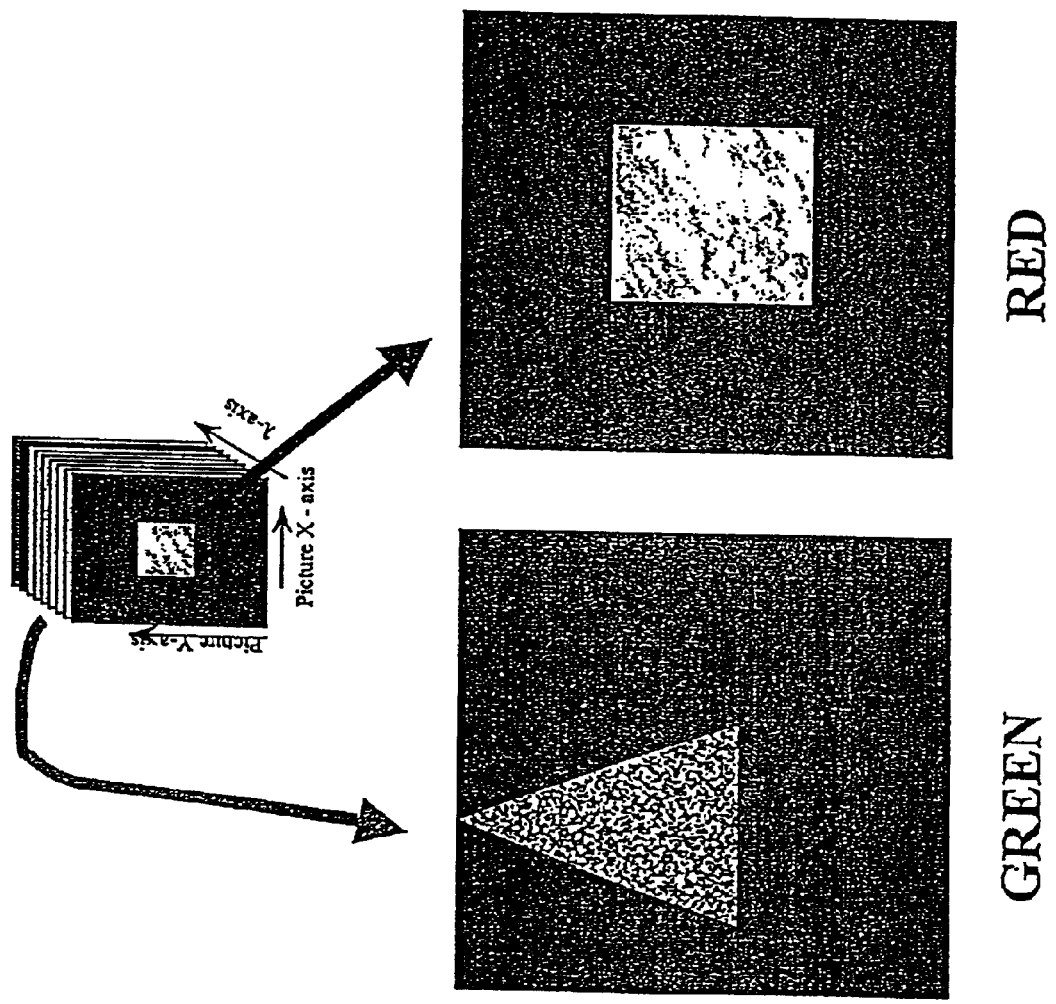
FIG. 30 illustrates the difference in two spectral components (red and green) of a data cube produced by imaging the same object in different spectral bands.
Figure 31A:
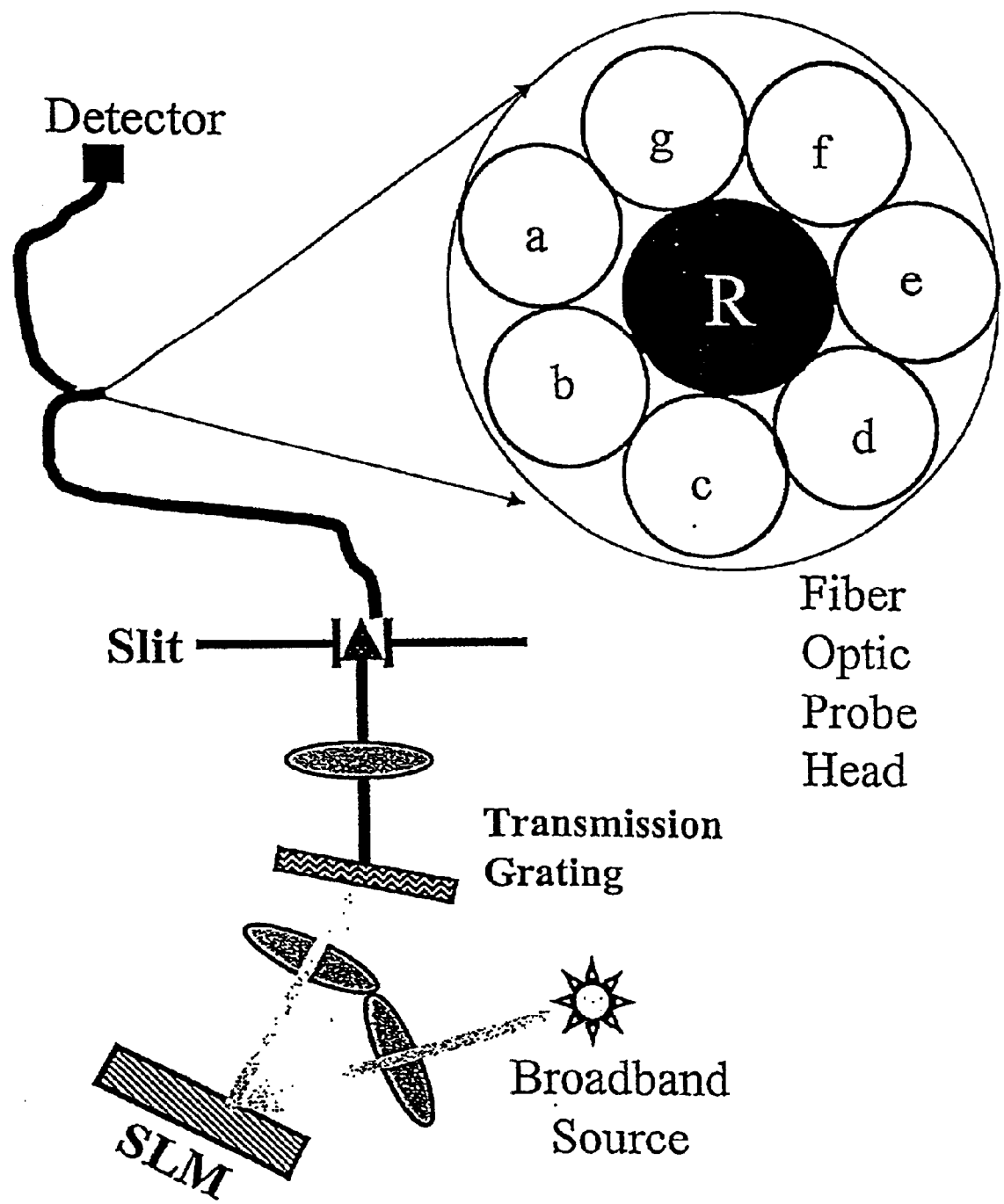
FIGS. 31A–E illustrate different embodiments of an imaging spectrograph used in accordance with this invention in de-dispersive mode.
Figure 31B:
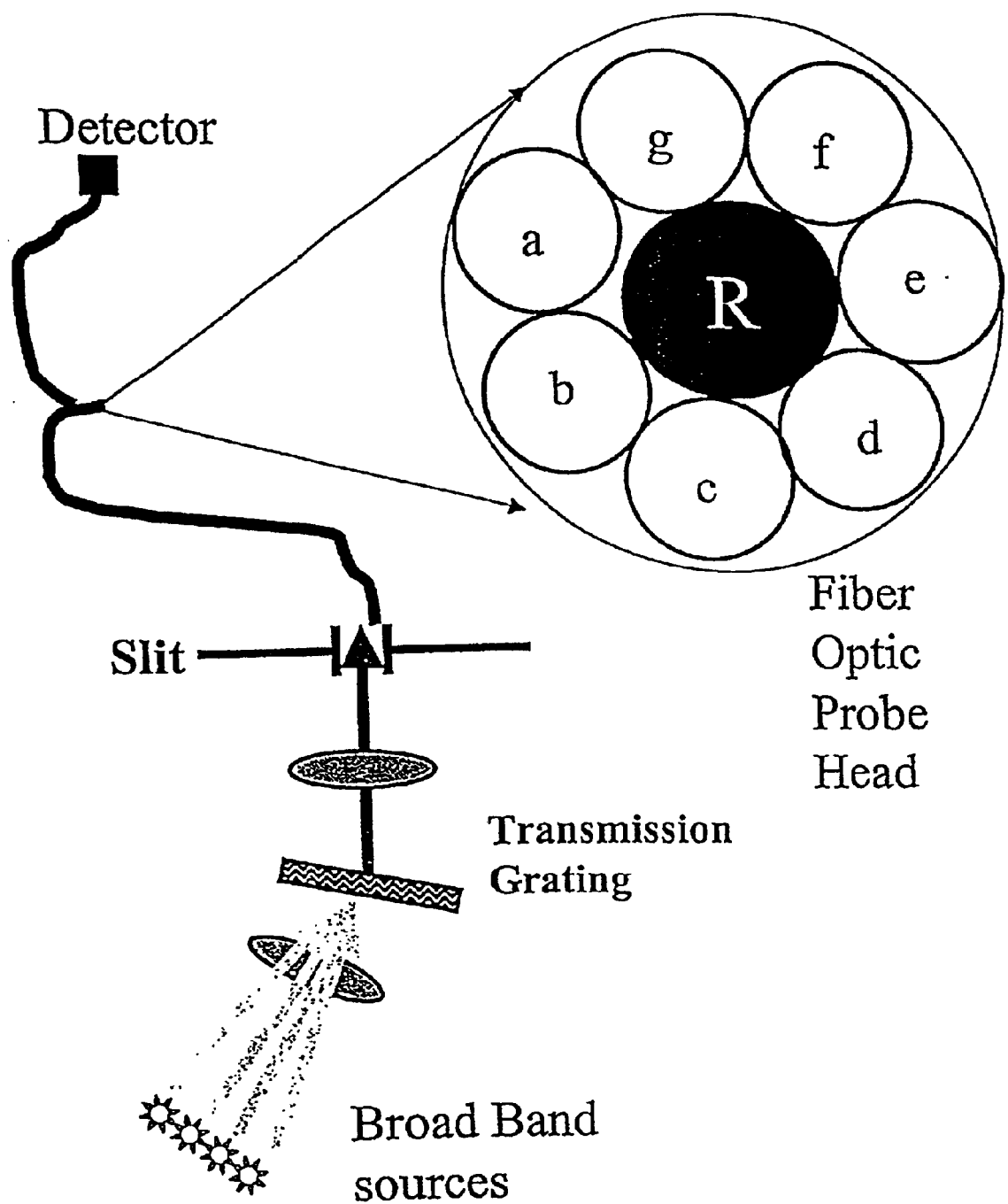
Figure 31C:
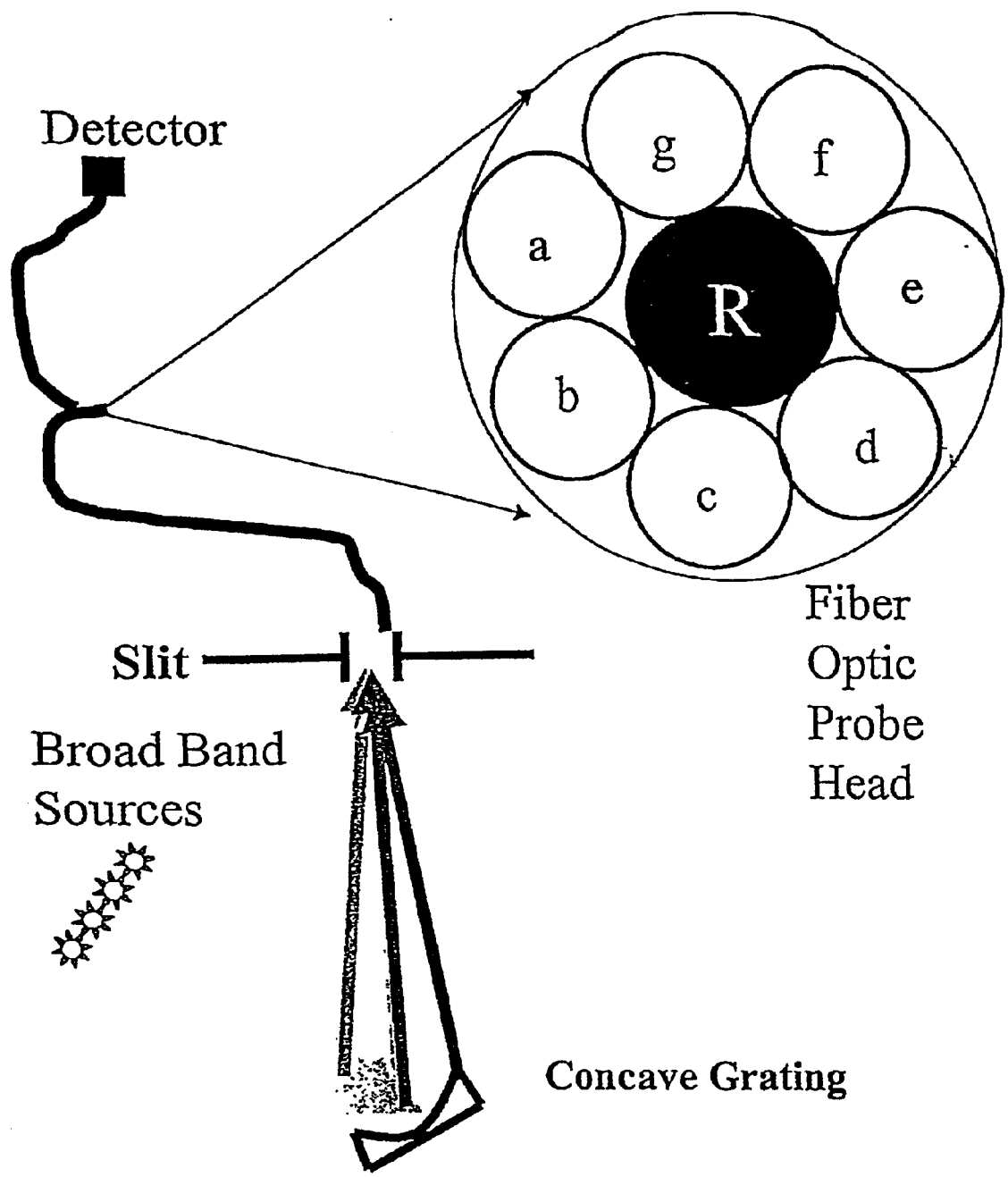
Figure 31D:
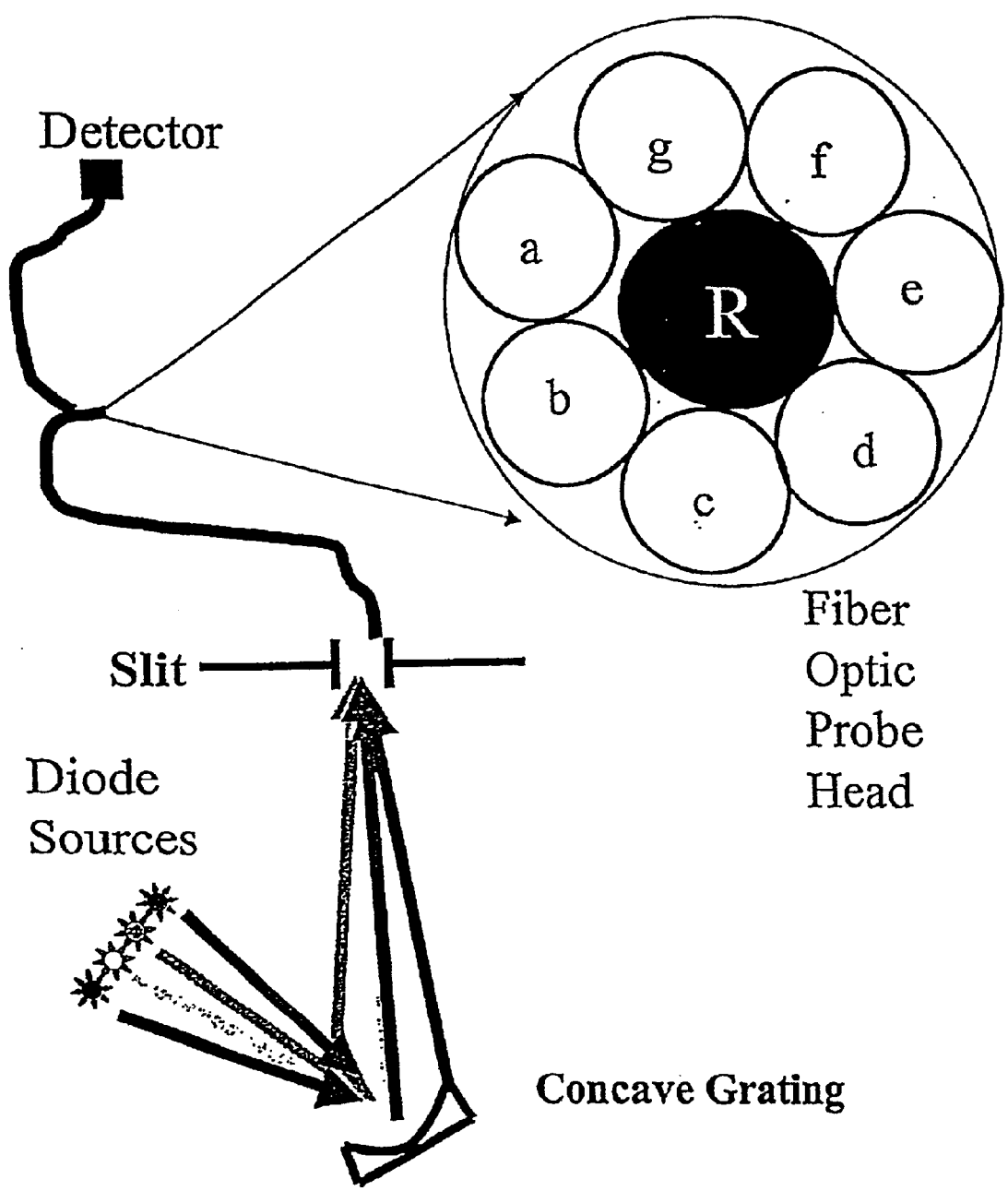
Figure 31E:
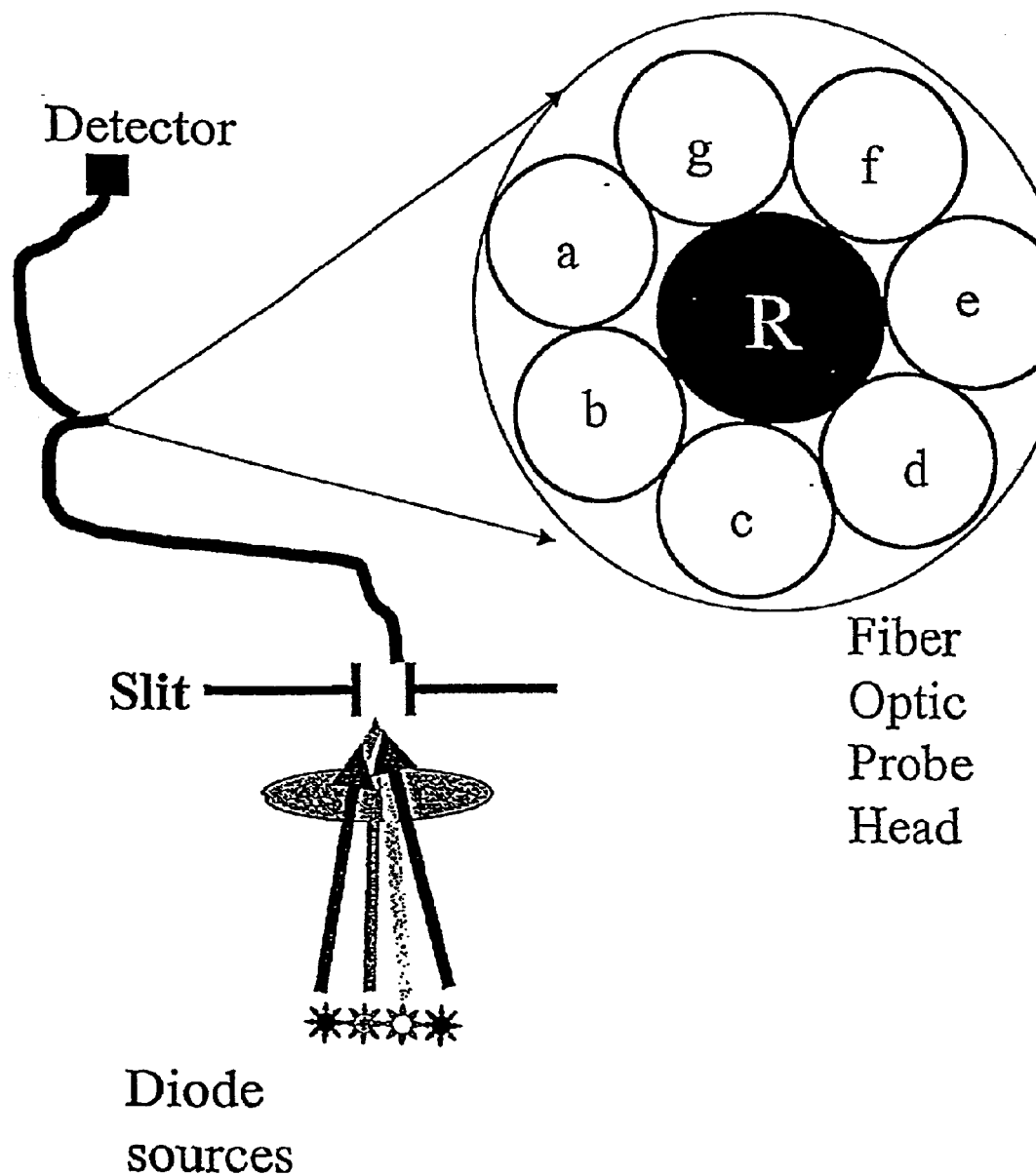

In accordance with the present invention, significant improvement over the prior art can be achieved using hyperspectral processing that focuses of predefined characteristics of the data. For example, in many cases only a few particular spectral lines or bands out of the whole data space are required to discriminate one substance over another. It is also often the case that target samples do not possess very strong or sharp spectral lines, so it may not be necessary to use strong or sharp bands in the detection process. A selection of relatively broad bands may be sufficient do discriminate between the target object and the background. It should be apparent that the ease with which different spatio-spectral bands can be selected and processed in accordance with the present invention is ideally suited for such hyperspectrum applications. A generalized block diagram of hyperspectral processing in accordance with the invention is shown in FIG. 29. FIG. 30 illustrates two spectral components (red and green) of a data cube produced by imaging the same object in different spectral bands. It is quite clear that different images contain completely different kinds of information about the object. The same idea is illustrated in FIGS. 31 and 32, where FIG. 31 illustrates hyperspectral imaging from airborne camera and shows how one can identify different crops in a scene, based on the predominant spectral characteristic of the crop. FIG. 32 is an illustration of a hyperspectral image of human skin with spectrum progressing from left to right and top to bottom, with increasing wavelength.

FIGS. 31A–E illustrate different embodiments of an imaging spectrograph in de-dispersive mode, that can be used in accordance with this invention for hyperspectral imaging in the UV, visual, near infrared and infrared portions of the spectrum. For illustration purposes, the figures show a fiber optic probe head with a fixed number of optical fibers. As shown, the fiber optic is placed at an exit slit. It will be apparent that a multitude of fiber optic elements and detectors can be used in alternate embodiments.

FIG. 32 shows an axial and cross-sectional view of the fiber optic assembly illustrated in FIGS. 31A–E .

Figure 33:
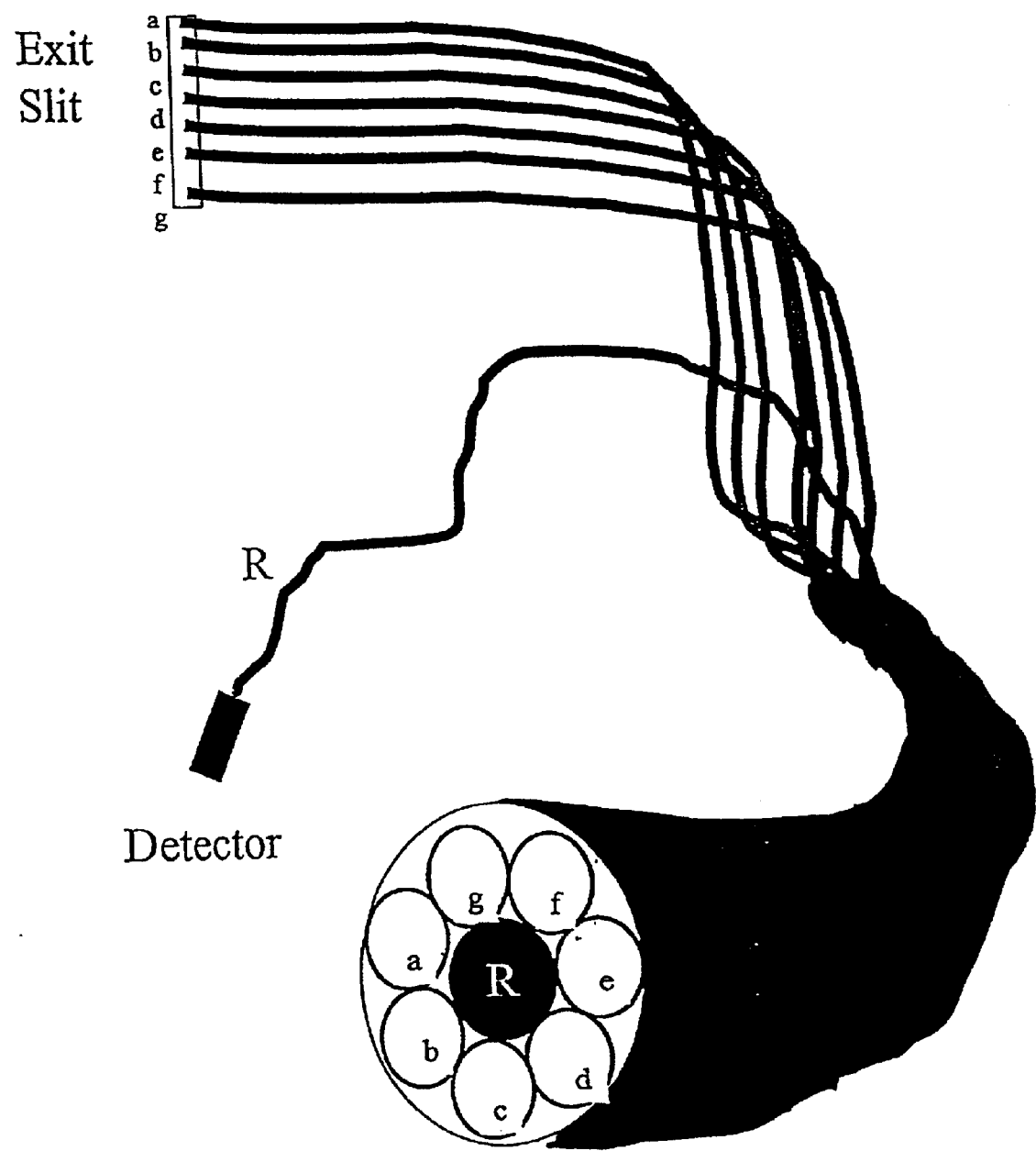
FIG. 33 shows a physical arrangement of the fiber optic cable, detector and the slit.
Figure 34:
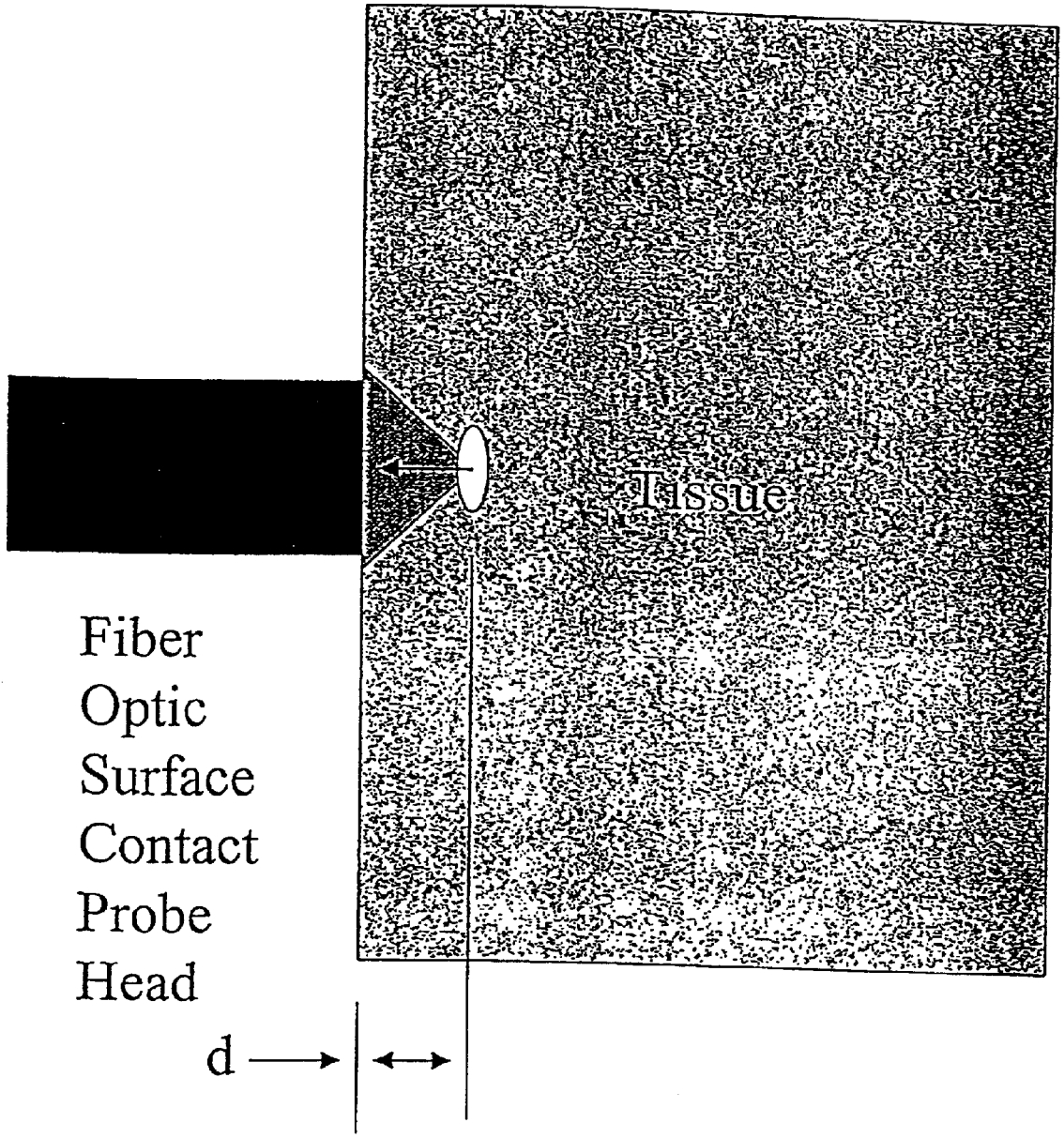
FIG. 34 illustrates a fiber optic surface contact probe head abutting tissue to be examined.
Figure 35A:
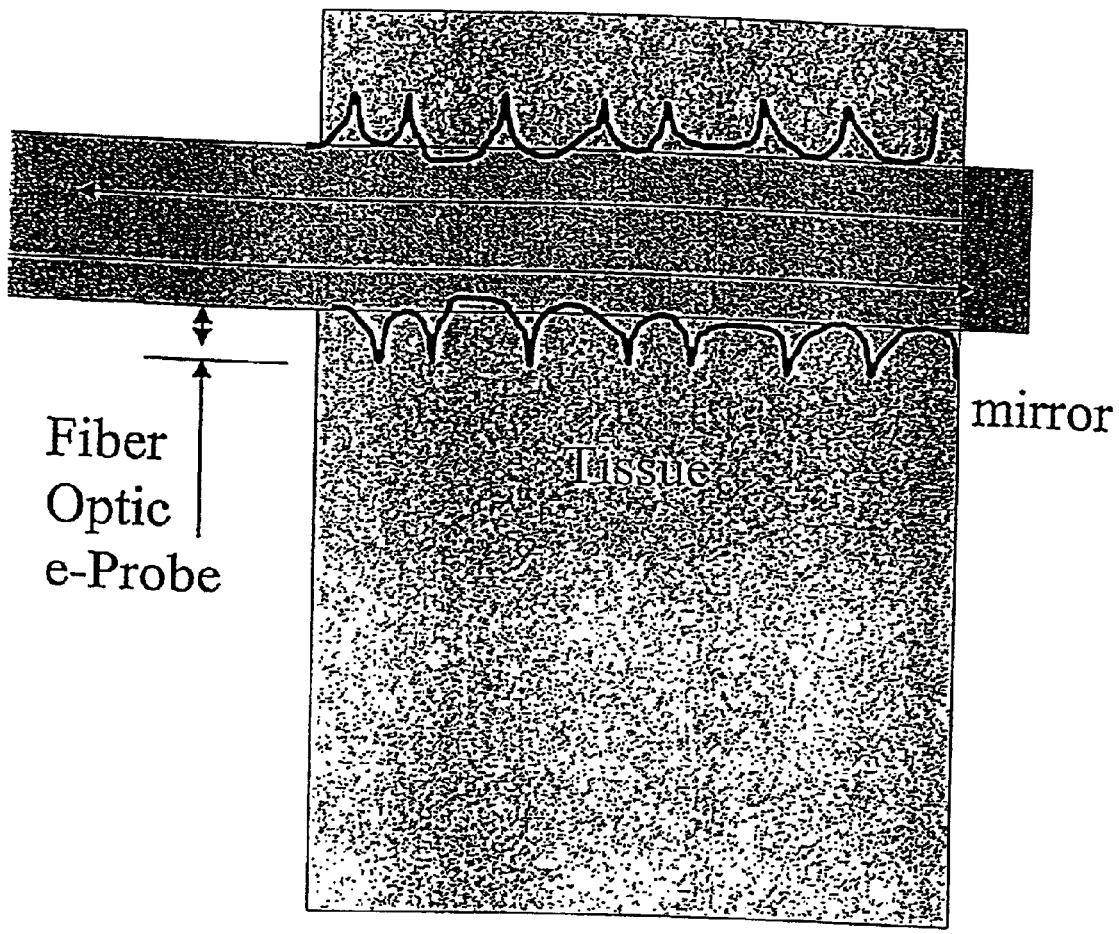
FIG. 35A and 35B illustrate a fiber optic e-Probe for pierced ears that can be used for medical monitoring applications in accordance with the present invention.
Figure 35B:
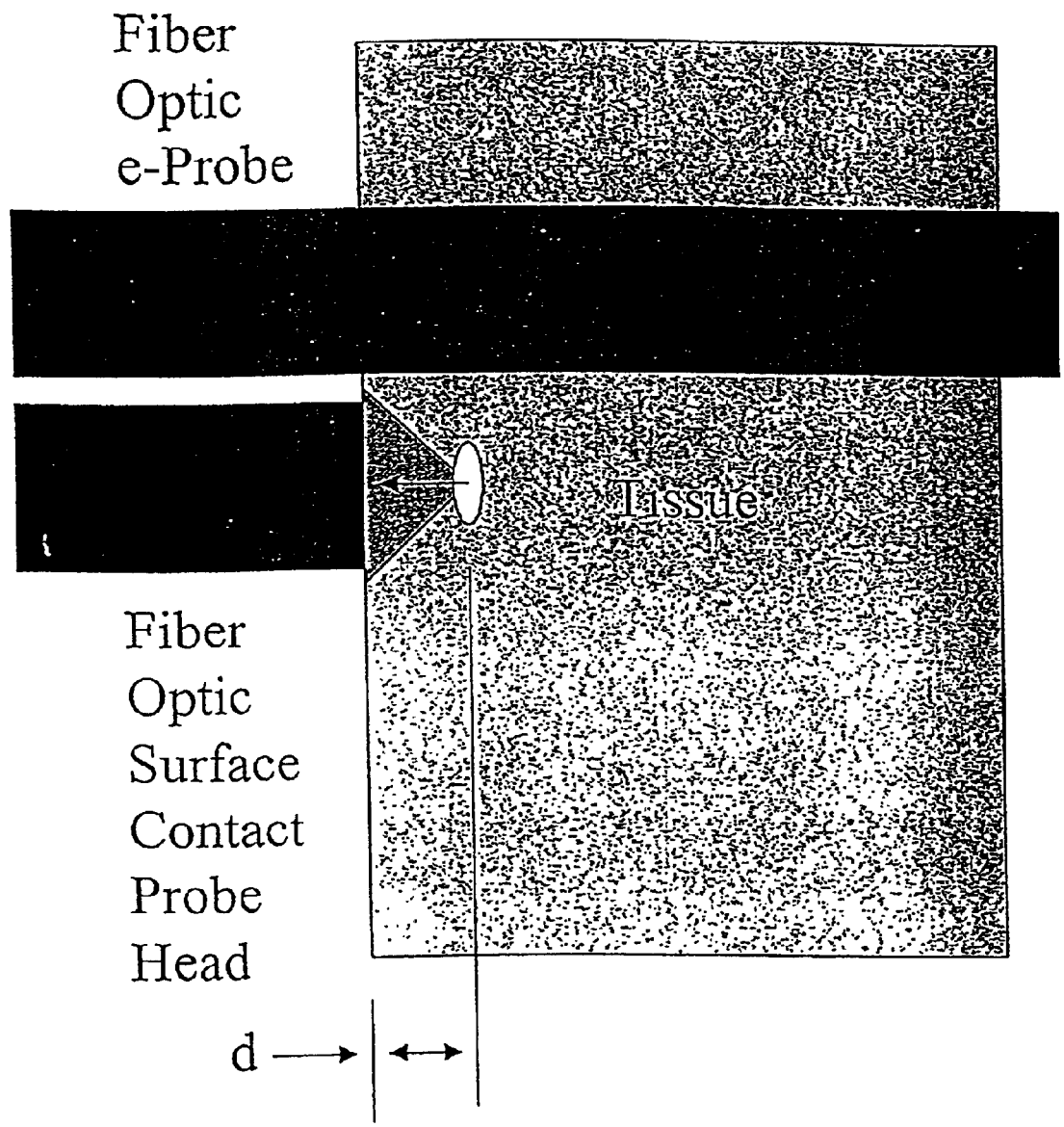

FIG. 33 shows a physical arrangement of the fiber optic cable, detector and the slit. FIG. 34 illustrates a fiber optic surface contact probe head abutting tissue to be examined;

FIGS. 35A and 35B illustrate a fiber optic e-Probe for pierced ears that can be used for medical monitoring applications in accordance with the present invention.

Figure 36A:
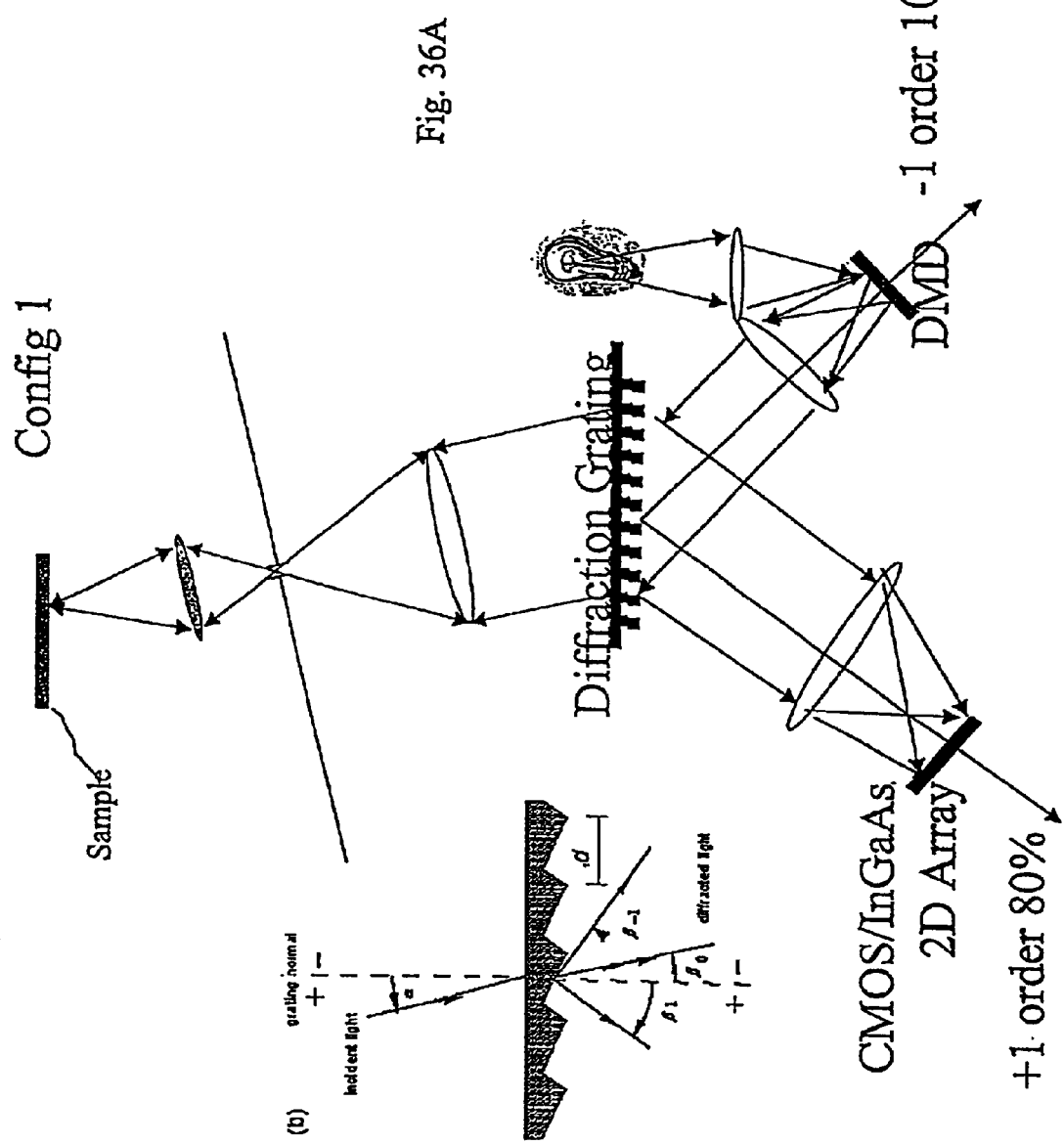
Figure 36B:
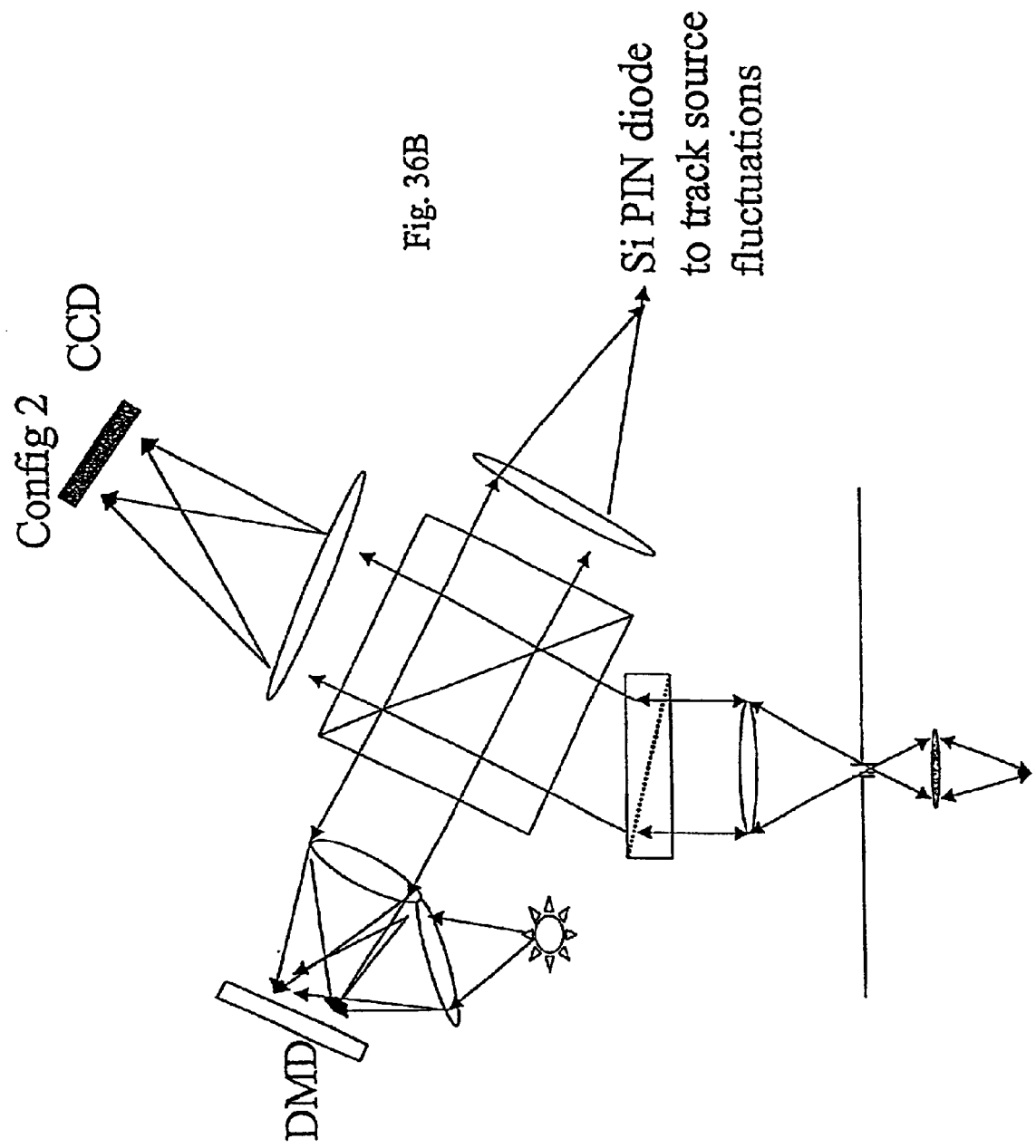

FIGS. 36A, 36B and 36C illustrate different configurations of a hyperspectral adaptive wavelength advanced illuminating imaging spectrograph (HAWAIIS).

In FIG. 36A, DMD (shown illuminating the −1 order) is a programmable spatial light modulator that is used to select spatio/spectral components falling upon and projecting from the combined entrance/exit slit. The illumination is fully programmable and can be modulated by any contiguous or non-contiguous combination at up to 50 KHz. The corresponding spatial resolution element located at the Object/sample is thus illuminated and is simultaneously spectrally imaged by the CCD (located in order +1 with efficiency at 80%) as in typical CCD imaging spectrographs used for Raman spectral imaging.

With reference to FIG. 36, the output of a broadband light source such as a TQH light bulb (1001) is collected by a collection optic (lens 1002) and directed to a spatial light modulator such as the DMA used in this example (1003). Specific spatial resolution elements are selected by computer controlled DMA driver to propagate to the transmission diffraction grating (1005) via optic (lens 1004). The DMA (1003) shown illuminating the −1 order of the transmission diffraction grating (1005) is a programmable spatial light modulator that is used to select spatio/spectral resolution elements projecting through the entrance/exit slit (#1007) collected and focused upon the sample (1009) by optic (lens 1008). The spatio/spectral resolution elements illuminating the sample are fully programmable. The sample is thus illuminated with specific and known spectral resolution elements. The reflected spectral resolution elements from specific spatial coordinates at the sample plane are then collected and focused back through the entrance/exit slit by optic (lens 1008). Optic (lens 1006) collimates the returned energy and presents it to the transmission diffraction grating (1005). The light is then diffracted preferentially into the +1 order and is subsequently collected and focused by the optic (lens 1010) onto a 2D dector array (1011). This conjugate spectral imaging device has the advantage of rejecting out of focus photons from the sample. Spectral resolution elements absorbed or reflected are measured with spatial specificity by the device.

FIGS. 43–47(A–D) illustrate hyperspectrum processing in accordance with the present invention, including data maps, encodement mask, DMA programmable resolution using different numbers of mirrors and several encodegrams.

D. Spatio-spectral Tagging

One of the most important aspects of the present invention is the use of modulation of single array elements or groups of array elements to "tag" radiation impinging on these elements with its own pattern of modulation. In essence, this aspect of the invention allows to combine data from a large number of array elements into a few processing channels, possibly a single channel, without losing the identity of the source and/or the spatial or spectral distribution of the data.

As known in the art, combination of different processing channels into a smaller number of channels is done using signal multiplexing. In accordance with the present invention, multiplexing of radiation components which have been "tagged" or in some way encoded to retain the identity of their source, is critical in various processing tasks, and in particular enables simple, robust implementations of practical devices. Thus, for example, in accordance with the principles of the present invention, using a micro mirror array, an optical router, an on-off switch (such as an LCD screen), enables simplified and robust image formation with a single detector and further makes possible increasing the resolution of a small array of sensors to any desired size, as discussed in Section IV next.

The important point in this respect is that in accordance with this invention, methods for digitally-controlled modulation of sensor arrays are used to perform signal processing tasks while collecting data. Thus, the combination and binning of a plurality of radiation sources is manipulated in accordance with this invention to perform calculations on the analog data, which is traditionally done in the digital data analysis process. As a result, a whole processing step can be eliminated by preselecting the switching modulation to perform the processing before the A/D conversion, thereby only converting data quantities of interest. This aspect of the present invention enables realtime representation of the final processed data, which in processing-intense applications can be critical.

E. Data Compression, Feature Extraction and Diagnostics

By modulating the SLM array used in accordance with this invention, so as to compute inner products with elements of an orthogonal basis, the raw data can be converted directly on the sensor to provide the data in transform coordinates, such as Fourier transform, Wavelet transform, Hadamard, and others. This is in fact a key aspect of the resent invention, and the reason why it is important is that the amount of data collected is so large that it may swamp the processor or result in insufficient bandwidth for storage and transmission. As known in the art, without some compression many imaging devices may become useless. As noted above, for hyperspectral imaging a full spectrum (a few hundred data points) is collected for each individual pixel resulting in a data glut. Thus, compression and feature extraction are essential to enable a meaningful image display. It will be appreciated that the resulting data file is typically much smaller, providing significant savings in both storage and processing requirements. A simple example is the block 8×8 Walsh expansion, which is automatically computed by appropriate mirror modulation, the data measured is the actual compressed parameters.

In another related aspect of the present invention, data compression can also be achieved by building an orthogonal basis of functions retaining the important features for the task at hand. In a preferred embodiment, this can be achieved by use of the best basis algorithm. See, for example, Coifman, R. R. and Wickerhauser, M. V., "Entropy-based Algorithms for Best Basis Selection", IEEE Trans. Info. Theory 38 (1992), 713–718, and U.S. Pat Nos. 5,526,299 and 5,384,725 to one of the inventors of this application. The referenced patents and publications are incorporated herein by reference.

By means of background, it is known that the reduction of dimensionality of a set of data vectors can be accomplished using the projection of such a set of vectors onto a orthogonal set of functions, which are localized in time and frequency. In a preferred embodiment, the projections are defined as correlation of the data vectors with the set of discretized re-scaled Walsh functions, but any set of appropriate functions can be used instead, if necessary.

The best basis algorithm to one of the co-inventors of this application provides a fast selection of an adapted representation for a signal chosen from a large library of orthonormal bases. Examples of such libraries are the local trigonometric bases and wavelet packet bases, both of which consist of waveforms localized in time and frequency. An orthonormal basis in this setting corresponds to a tiling of the time-frequency plane by rectangles of area one, but an arbitrary such tiling in general does not correspond to an orthonormal basis. Only in the case of the Haar wavelet packets is there a basis for every tiling, and a fast algorithm to find that basis is known. See, Thiele, C. and Villemoes, L., "A Fast Algorithm for Adapted Time-Frequency Tilings", Applied and Computational Harmonic Analysis 3 (1996), $91 \geqq 99$, which is incorporated by reference.

Walsh packet analysis is a robust, fast, adaptable, and accurate alternative to traditional chemometric practice. Selection of features for regression via this method reduces the problems of instability inherent in standard methods, and provides a means for simultaneously optimizing and automating model calibration.

The Walsh system $\{W_n\}_{n=0}^{\infty}$ is defined recursively by $$W_{2n}(t)=W_2 t)+(-1)^n(2t-1)$$

$$W_{2n+1}(t)=W_n(2t)-(-1)^n W_n(2t-1)$$

With $W_0(t)=1$ on $0 \leq t < 1$. If $[0,1[ \times [0, \infty[$ is the time frequency plane, dyadic rectangles are subsets of the form $$I \times \omega = [2^{-j}k, 2^{-j}(k+1)] \times [2^m n, 2^m(n+1)],$$

with j, k, m and n non-negative integers, and the tiles are the rectangles of area one (j=m). A tile p is associated with a rescaled Walsh function by the expression $$w_p(t)=2^{j/2}W_n(2^j t-k)$$

Fact: The function $w_p$ and $w_q$ are orthogonal if and only if the tiles p and q are disjoint. Thus, any disjoint tiling will give rise to an orthonormal basis of $L^2(0,1)$ consisting of rescaled Walsh functions. For any tiling B, we may represent a function f as $$f = \sum_{p \in B} \langle f, w_p \rangle w_p$$

and may find an optimal such representation for a given additive cost functional by choosing a tiling minimizing the cost evaluated on the expansion coefficients.

In Section IV we consider an example contrasting the use of adaptive Walsh packet methods with standard chemometrics for determining protein concentration in wheat. The data consists of two groups of wheat spectra, a calibration set with 50 samples and a validation set of 54 samples. Each individual spectrum is given in units of log (1/R) where R is the reflectance and is measured at 1011 wavelengths, uniformly spaced from 1001 nm to 2617 nm. Standard chemometric practice involves computing derivative-like quantities at some or all wavelengths and building a calibration model from this data using least squares or partial least squares regression.

To illustrate this, let $Y_i$ be the percent protein for the i-th calibration spectrum $S_i$, and define the feature $X_i$ to be $$X_i = \frac{S_i(2182 \text{ nm}) - S_i(2134 \text{ nm})}{S_i(2183 \text{ nm}) - S_i(2260 \text{ nm})}$$

where $S_i(\text{WLnm})$ is log(1/R) for the i-th spectrum at wavelength WL in nanometers. This feature makes use of 4 of the 1011 pieces of spectral data, and may be considered an approximate ratio of derivatives. Least squares provides a linear model $AX_i+B$ yielding a prediction $\hat{Y}_i$ of $Y_i$. An estimate of the average percentage regression error is given by:

$$\frac{100}{N} \sum_{i=1}^{N} \frac{|\hat{Y}_i - Y_i|}{|Y_i|}$$

with N being the number of sample spectra in the given data set (N is 50 for the calibration set). Retaining the same notation as for the calibration set, one can compute the feature $X_i$ for each validation spectrum $S_i$ and use the above model to predict $Y_i$ for the validation spectra. The average percentage regression error on the validation set is 0.62%, and this serves as the measure of success for the model. This model is known to be state-of-the-art in terms of both concept and performance for this data, and will be used as point of comparison.

The wavelength-by-wavelength data of each spectrum is a presentation of the data in a particular coordinate system. Walsh packet analysis provides a wealth of alternative coordinate systems in which to view the data In such a coordinate system, the coordinates of an individual spectrum would be the correlation of the spectrum with a given Walsh packet. The Walsh packets themselves are functions taking on the values 1, −1, and 0 in particular patterns, providing a square-wave analogue of local sine and cosine expansions. Examples of Walsh packets are shown in FIG. 28.

In accordance with the present invention, such functions may be grouped together to form independent coordinate systems in different ways. In particular, the Walsh packet construction is dyadic in nature and yields functions having $N=2^k$ sample values. For N=1024, the closest value of N for the example case of spectra having 1011 sample values, the number of different coordinate systems is approximately $10^{272}$. If each individual Walsh packet is assigned a numeric cost (with some restrictions), a fast search algorithm exists, which will find the coordinate system of minimal (summed) cost out of all possible Walsh coordinate systems. Despite the large range for the search, the algorithm is in not approximate, and provides a powerful tool for finding representations adapted to specific tasks.

These ideas may be applied to the case of regression for the wheat data in question. Any Walsh packet provides a feature, not unlike the computed above, simply by correlating the Walsh packet with each of the spectra. These correlations may be used to perform a linear regression to predict the protein concentration. The regression error can be used as a measure of the cost of the Walsh packet. A good coordinate system for performing regression is then one in which the cost, i.e. the regression error, is minimal. The fast algorithm mentioned above gives us the optimal such representation, and a regression model can be developed out of the best K (by cost) of the coordinates selected.

In a particular embodiment, for each of the calibration spectra $S_i$, first compute all possible Walsh packet features and then determine the linear regression error in predicting the $Y_i$ for each Walsh packet. Using this error as a cost measure, select a coordinate system optimized for regression, to provide a (sorted) set of features $\{X_i(1), \ldots, X_i(K)\}$ associated with each spectrum $S_i$. These features are coordinates used to represent the original data, in the same way that the wavelength data itself does. Four features were used in the standard model described above, and, hence, one can choose K=4 and use partial least squares regression to build a model for predicting $Y_i$. The average percentage regression error of this model on the validation data set is 0.7%, and this decreases to 0.6% for K=10. FIG. 39A shows a typical wheat spectrum together with one of the top 4 Walsh packets used in this model. The feature that is input to the regression model is the correlation of the Walsh packet with the wheat spectrum. (In this case the Walsh feature computes a second derivative, which suppresses the background and detects the curvature of the hidden protein spectrum in this region).

Figure 41A:
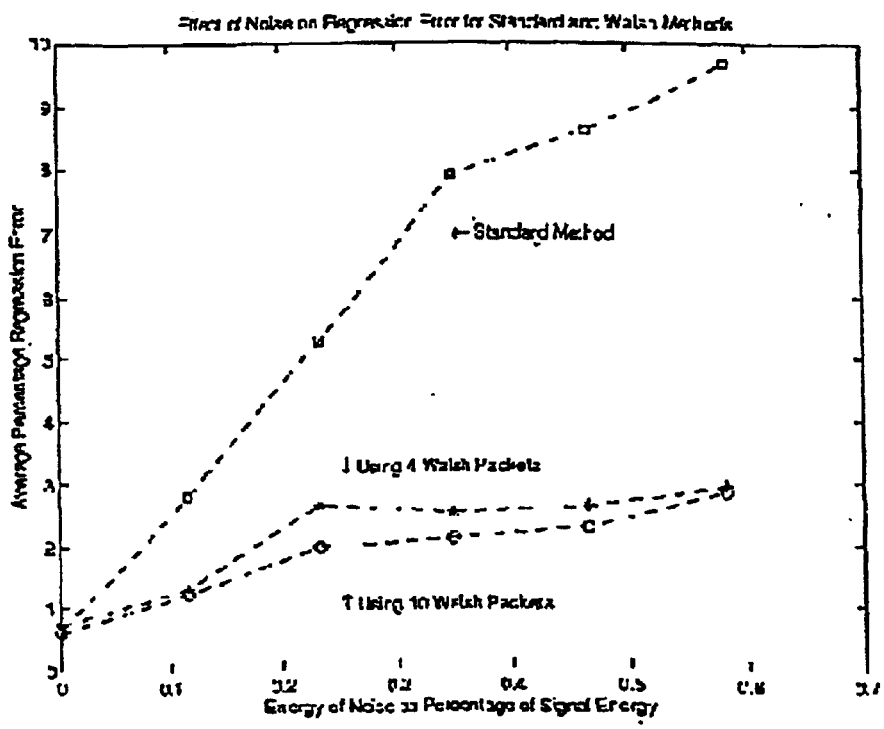
FIG. 41 illustrates PLS regression of protein content of test data.

Similar performance is achieved by Walsh packet analysis using the same number of features. The benefit of using the latter becomes clear if noise is taken into account. Consider the following simple and natural experiment: add small amounts of Gaussian white noise to the spectra and repeat the calibrations done above using both the standard model and the Walsh packet model. The results of this experiment are shown in FIG. 41A, which plots the regression error versus the percentage noise energy for both models (we show both the K=4 and the K=10 model for the Walsh packet case to emphasize their similarity). A very small amount of noise takes the two models from being essentially equivalent to wildly different, with the standard model having more than three times the percentage error as the Walsh packet model. The source of this instability for the standard model is clear. The features used in building the regression model are isolated wavelengths, and the addition of even a small amount of noise will perturb those features significantly. The advantage of the Walsh packet model is clear in FIG. 42. The feature being measured is a sum from many wavelengths, naturally reducing the effect of the noise.

The Walsh packet method described here has other advantages as well. One of the most important is that of automation. The fast search algorithm automatically selects the best Walsh packets for performing the regression. If the data set were changed to, say, blood samples and concentrations of various analytes, the same algorithm would apply off the shelf in determining optimal features. The standard model would need to start from scratch in determining via lengthy experiment which wavelengths were most relevant.

Adaptability is also an important benefit. The optimality of the features chosen is based on a numeric cost function, in this case a linear regression error. However, many cost functions may be used and in each case a representation adapted to an associated task will be chosen. Optimal coordinates may be chosen for classification, compression, clustering, non-linear regression, and other tasks. In each case, automated feature selection chooses a robust set of new coordinates adapted to the job in question.

IV. PRACTICAL APPLICATIONS

A number of applications of approaches and techniques used in accordance with the present invention were discussed or pointed to in the above disclosure. In this Section we present several applications illustrative of the advantages provided by the invention and the range of its practical utility.

A. Gray Level Camera Processing System and Method

This application concerns a processing system, in which a video camera is synchronized to modulation of a tunable light source, allowing analysis of the encoded spectral bands from a plurality of video images to provide a multispectral image. The utility of the application is due in part to the fact that it does not require special conditions—since the ambient light is not modulated it can be separated from the desired spectral information. The system is the functional equivalent of imaging the scene a number of times with a multiplicity of color filters. It allows the formation of any virtual photographic color filter with any absorption spectrum desired. A composite image combining any of these spectral bands can be formed to achieve a variety of image analysis, filtering and enhancing effects.

For example, an object with characteristic spectral signature can be highlighted by building a virtual filter transparent to this signature and not to others (which should be suppressed). In particular, for seeing the concentration of protein in a wheat grain pile (the example discussed below) it would be enough to illuminate with two different combination of bands in sequence and take the difference of the two consecutive images. More elaborate encodations may be necessary if more spectral combinations must be measured independently, but the general principle remains.

In a different embodiment, an ordinary video camera used in accordance with this invention is equipped with a synchronized tunable light source, so that odd fields are illuminated with a spectral signature that is modulated from odd field to odd field, while the even fields are modulated with the complementary spectral signature so that the combined even/odd light is white. Such an illumination system allows ordinary video imaging which after digital demodulation provides detailed spectral information on the scene with the same capabilities as a gray level camera.

This illumination processing system can be used for machine vision for tracking objects and anywhere that specific real time spectral information is useful.

In another embodiment, a gray level camera can measure several preselected light bands using, for example, 16 bands by illuminating the scene consecutively by the 16 bands and measuring one band at a time. A better result in accordance with this invention can be obtained by selecting 16 modulations, one for each band, and illuminating simultaneously the scene with all 16 colors. The sequence of 16 frames can be used to demultiplex the images. The advantages of multiplexing will be appreciated by those of skill in the art, and include: better signal to noise ratio, elimination of ambient light interference, tunability to sensor dynamic range constraints, and others.

A straightforward extension of this idea is the use of this approach for multiplexing a low resolution sensor array to obtain better image quality. For example, a 4×4 array of mirrors with Hadamard coding could distribute a scene of 400×400 pixels on a CCD array of 100×100 pixels resulting in an effective array with 16 times the number of CCD. Further, the error could be reduced by a factor of four over a raster scan of 16 scenes.

B. Chemical Composition Measurements

In accordance with the present invention by irradiating a sample of material with well-chosen bands of radiation that are separately identifiable using modulation, one can directly measure constituents in the material of interest. This measurement, for example, could be of the protein quantity in a wheat pile, different chemical compounds in human blood, or others. It should be apparent that there is no real limitation on the type of measurements that can be performed, although the sensors, detectors and other specific components of the device, or its spectrum range may differ.

In the following example we illustrate the measurement of protein in wheat, also discussed in Section III.E. above. The data consists of two groups of wheat spectra, a calibration set with 50 samples and a validation set of 54 samples.

Figure 37:
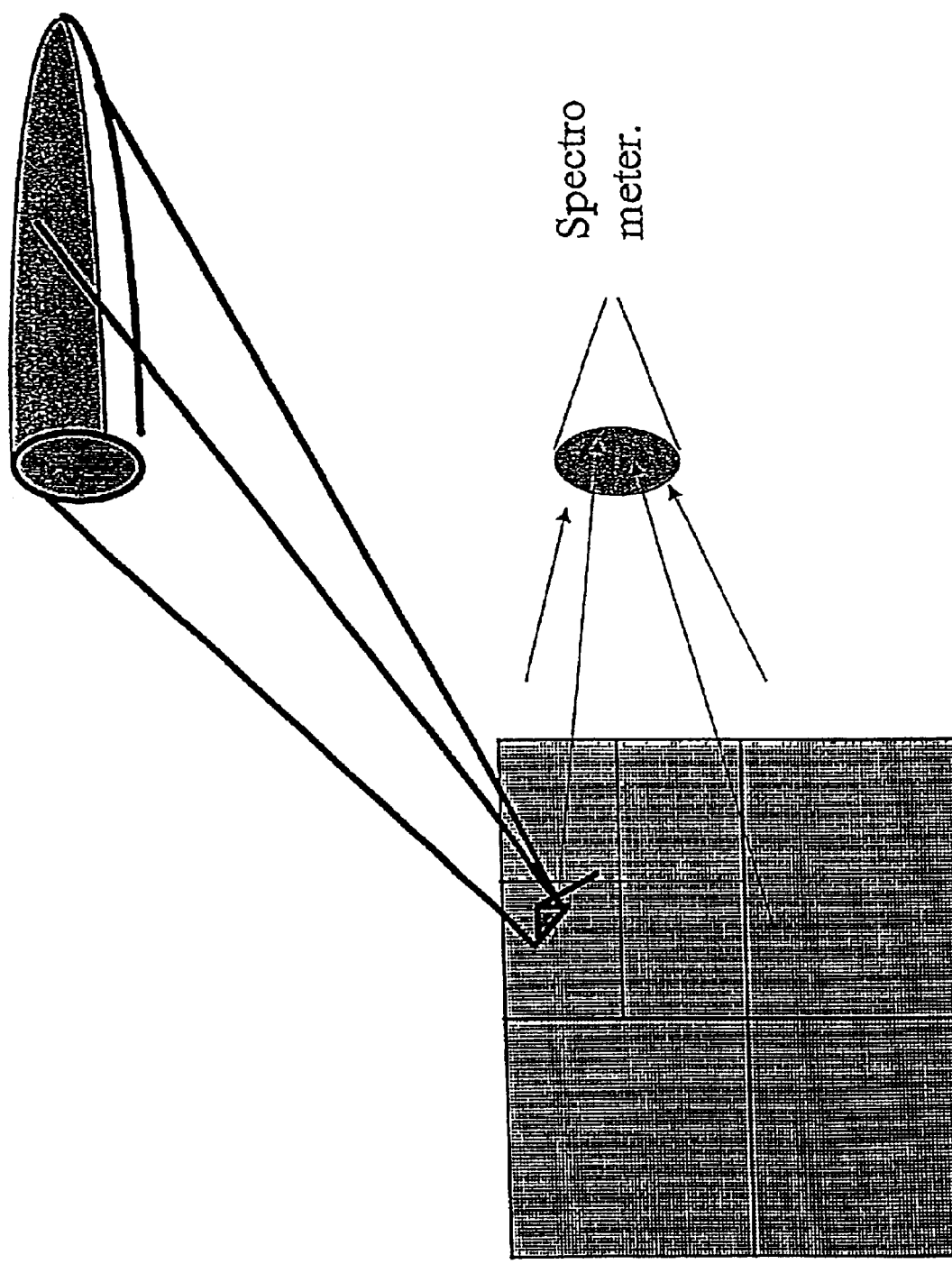
FIG. 37 illustrates a DMA search by splitting the scene.

With further reference to Section III.B, FIG. 37 shows a DMA search by splitting the scene. The detection is achieved by combining all photons from the scene into a single detector, then splitting the scene in parts to achieve good localization. In this example, one is looking for a signal with energy in the red and blue bands. Spectrometer with two detectors, as shown in FIG. 27 can be used, so that the blue light goes to the top region of the DMA, while the red goes to the bottom.

First, the algorithm checks if it is present in the whole scene by collecting all photons into the spectrometer, which looks for the presence of the spectral energies. Once the particular spectrum band is detected, the scene is split into four quarters and each is analyzed for presence of target. The procedure continues until the target is detected.

Figure 38:
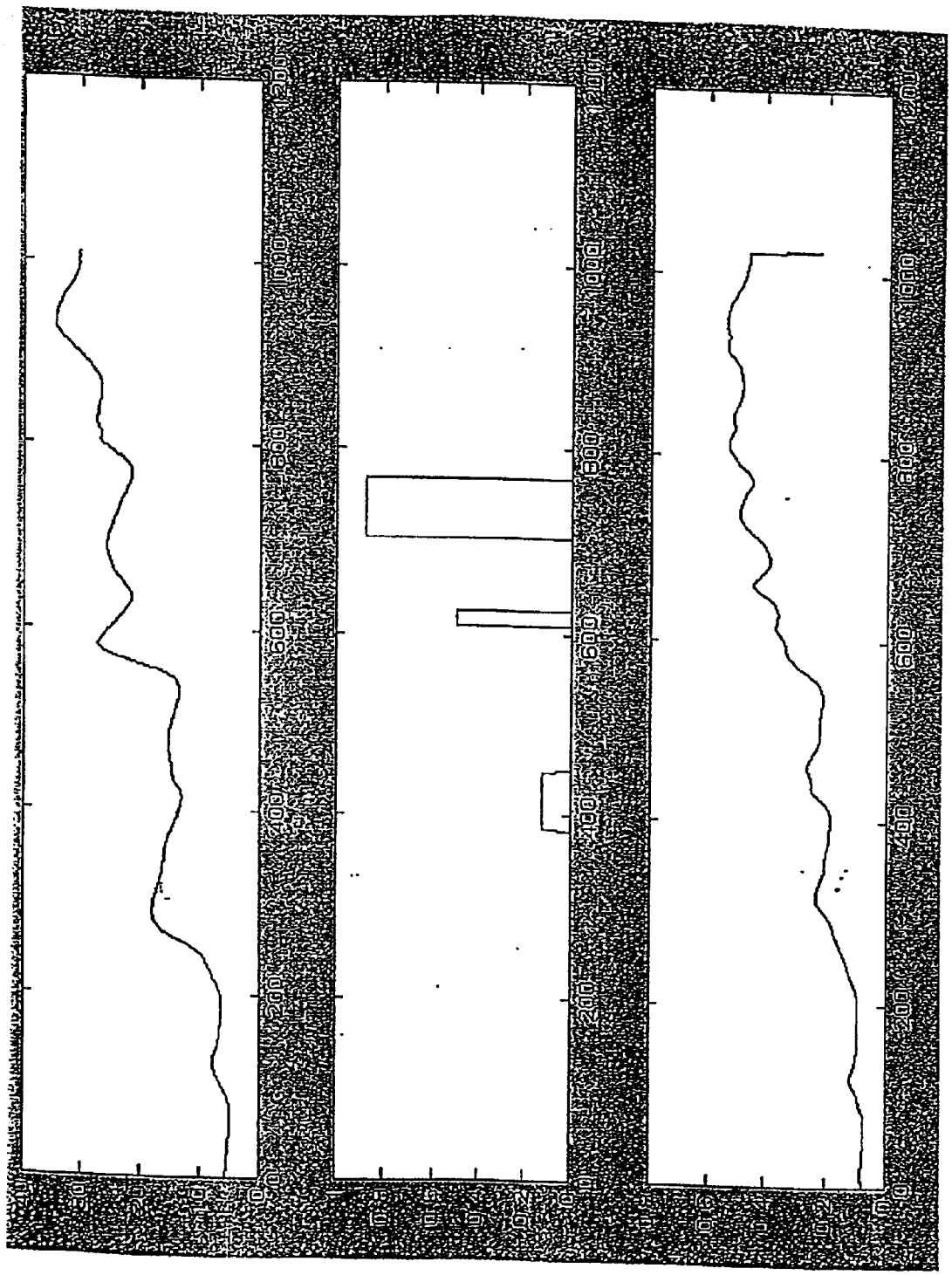
FIG. 38 illustrates wheat spectra data (training) and wavelet spectrum in an example of determining protein content in wheat.

FIG. 38 illustrates the sum of wheat spectra training data (top), sum of |w| for top 10 wavelet packets (middle), and an example of protein spectra—soy protein (bottom). The goal is to estimate the amount of protein present in wheat. The middle portion of the figure shows the region where the Walsh packets provide useful parameters for chemo-metric estimation.

Figure 39:
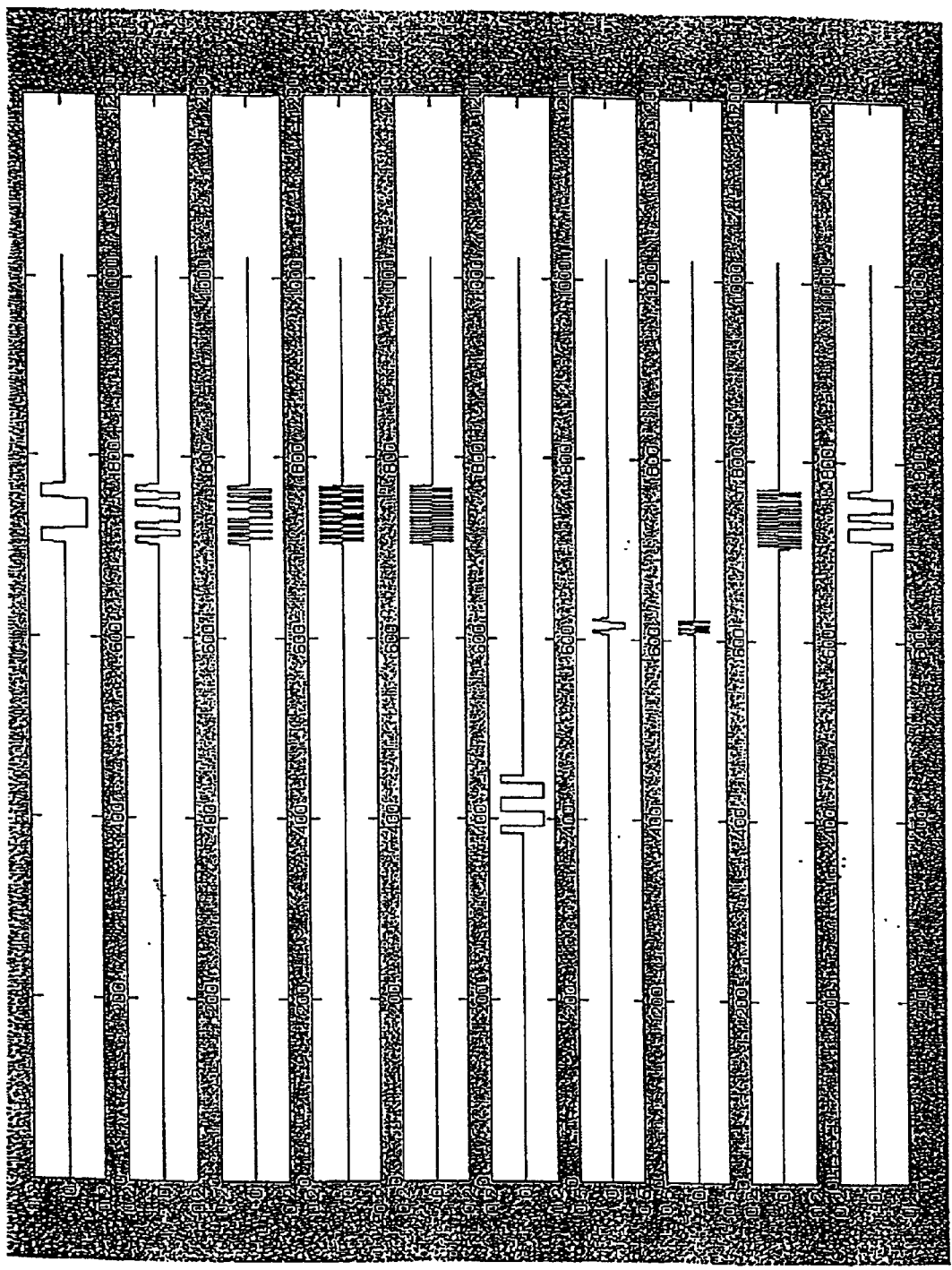
FIG. 39 illustrates the top 10 wavelet packets in local regression basis selected using 50 training samples in the example of FIG. 38.
Figure 39A:
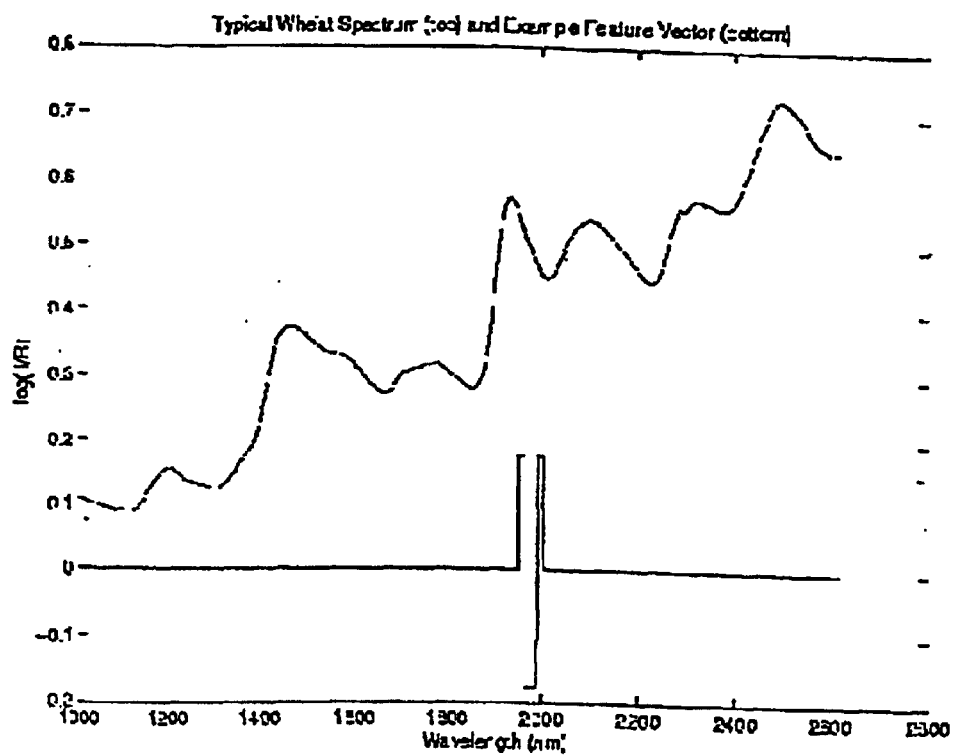
Figure 40:
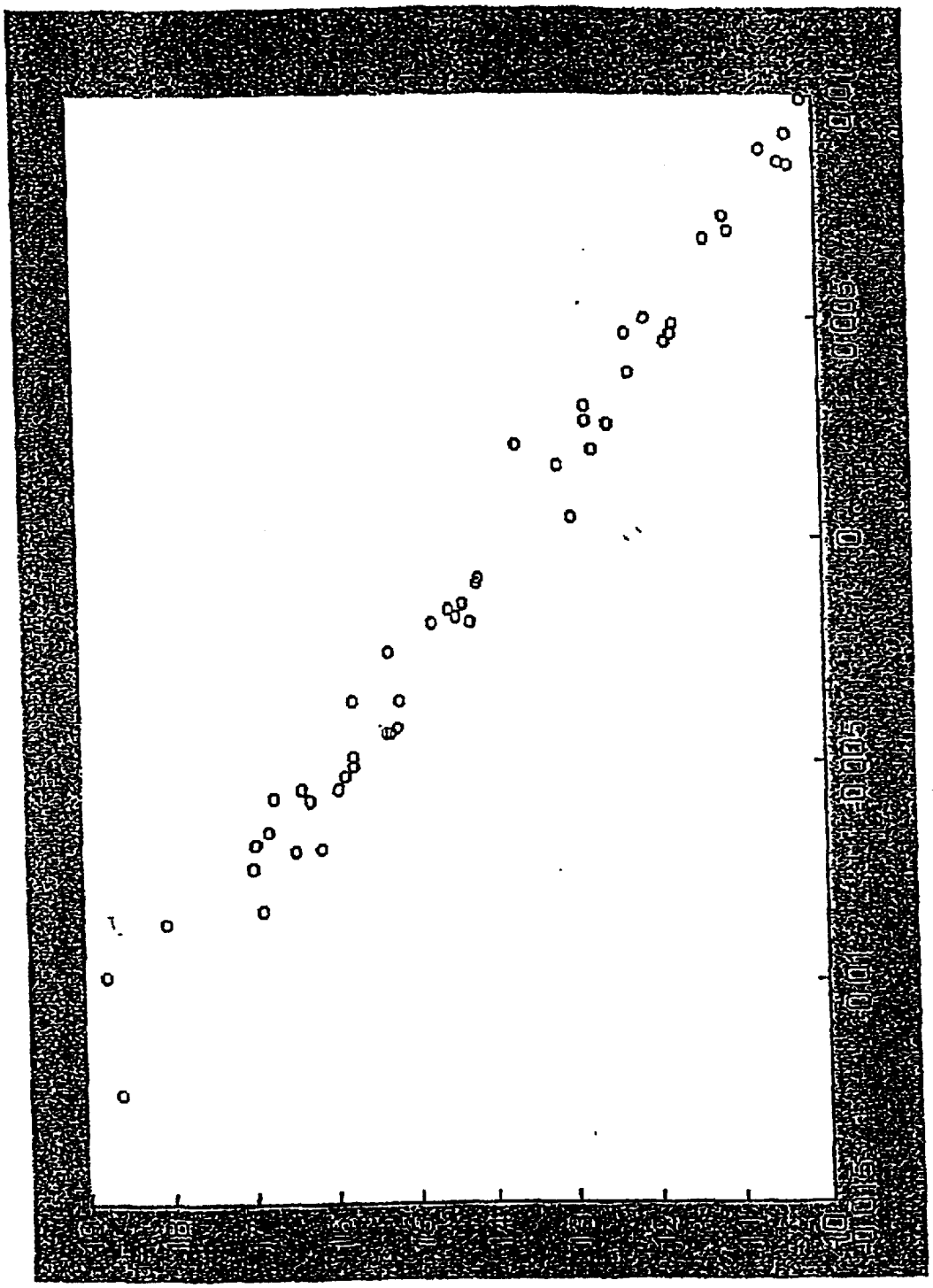
FIG. 40 is a scatter plot of protein content (test data) vs. correlation with top wavelet packet.

FIG. 39 illustrates the top 10 wavelet packets in local regression basis selected using 50 training samples. Each Walsh packet provides a measurement useful for estimation. For example, the top line indicates that by combining the two narrow bands at the ends and the subtracting the middle band we get a quantity that is linearly related to the protein concentration. FIG. 40 is a scatter plot of protein content (test data) vs. correlation with top wavelet packet. This illustrates a simple mechanism to directly measure relative concentration of desired ingredients of a mixture using the present invention.

It will be appreciated that in this case one could use an LED-based flashlight illuminating in the three bands with a modulated light, which is then imaged with a CCD video camera that converts any group of consecutive three images into an image of protein concentration. Another implementation is to replace the RGB filters on a video camera by three filters corresponding to the protein bands, to be displayed after substraction as false RGB. Various other alternative exist and will be appreciated by those of skill in the art.

Figure 41:
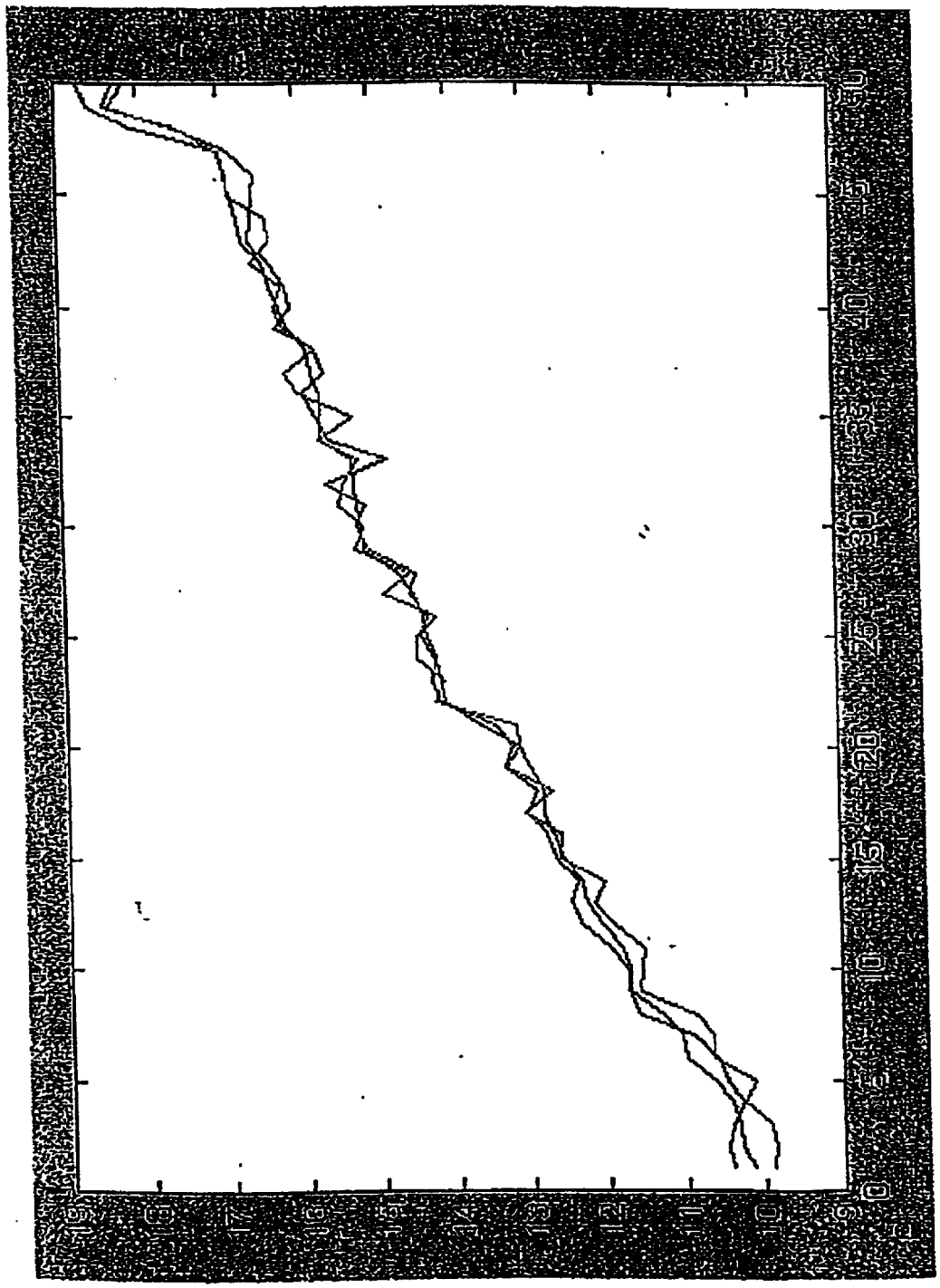

FIG. 41 illustrates PLS regression of protein content of test data: using top 10 wavelet packets (in green −1.87% error, from 6 LVs) and top 100 (in red −1.54% error from 2 LVs)—compare with error of 1.62% from 14 LVs using all original data. This graph compares the performance of the simple method described above to the true concentration values.

Figure 42:
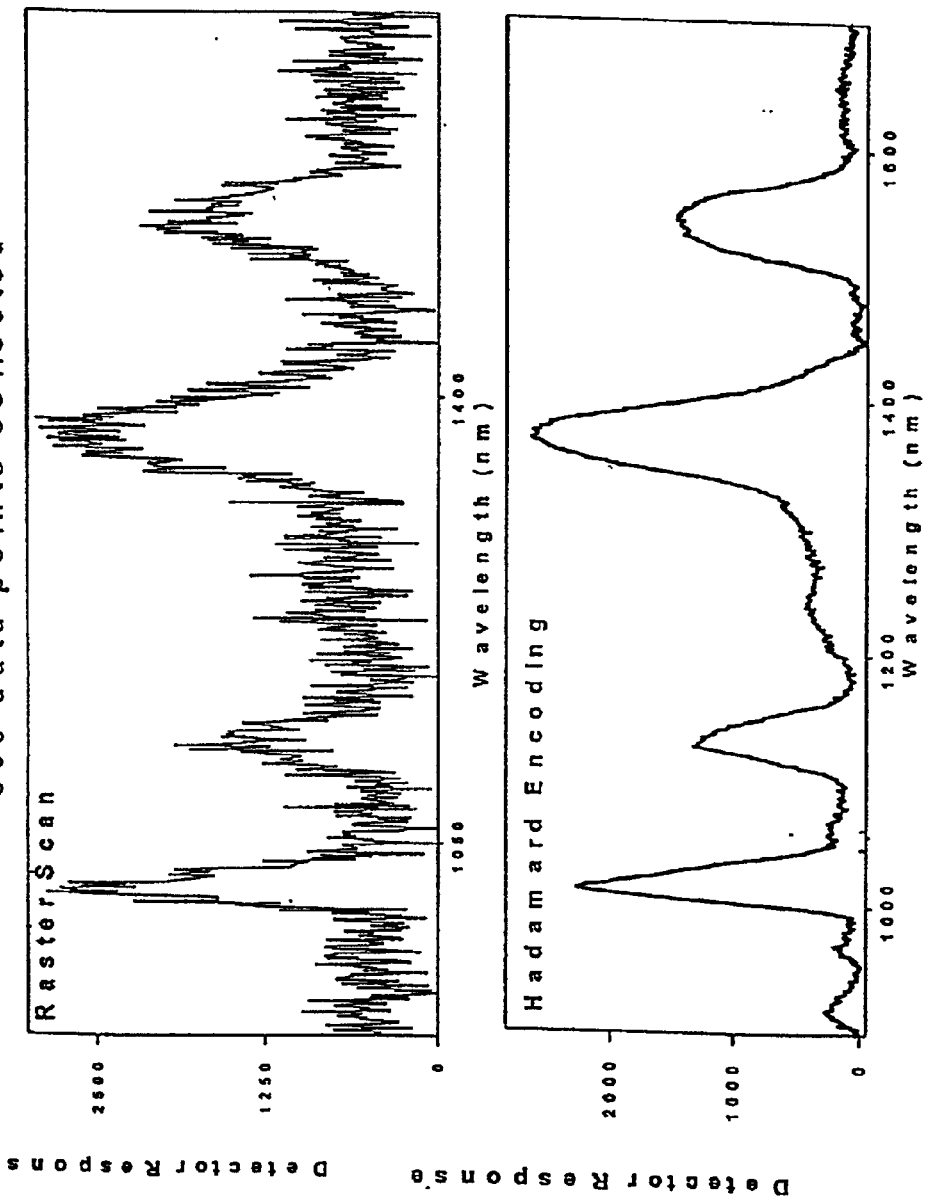
FIG. 42 illustrates the advantage of DNA-based Hadamard Spectroscopy used in accordance with the present invention over the regular raster scan.
Figure 43:
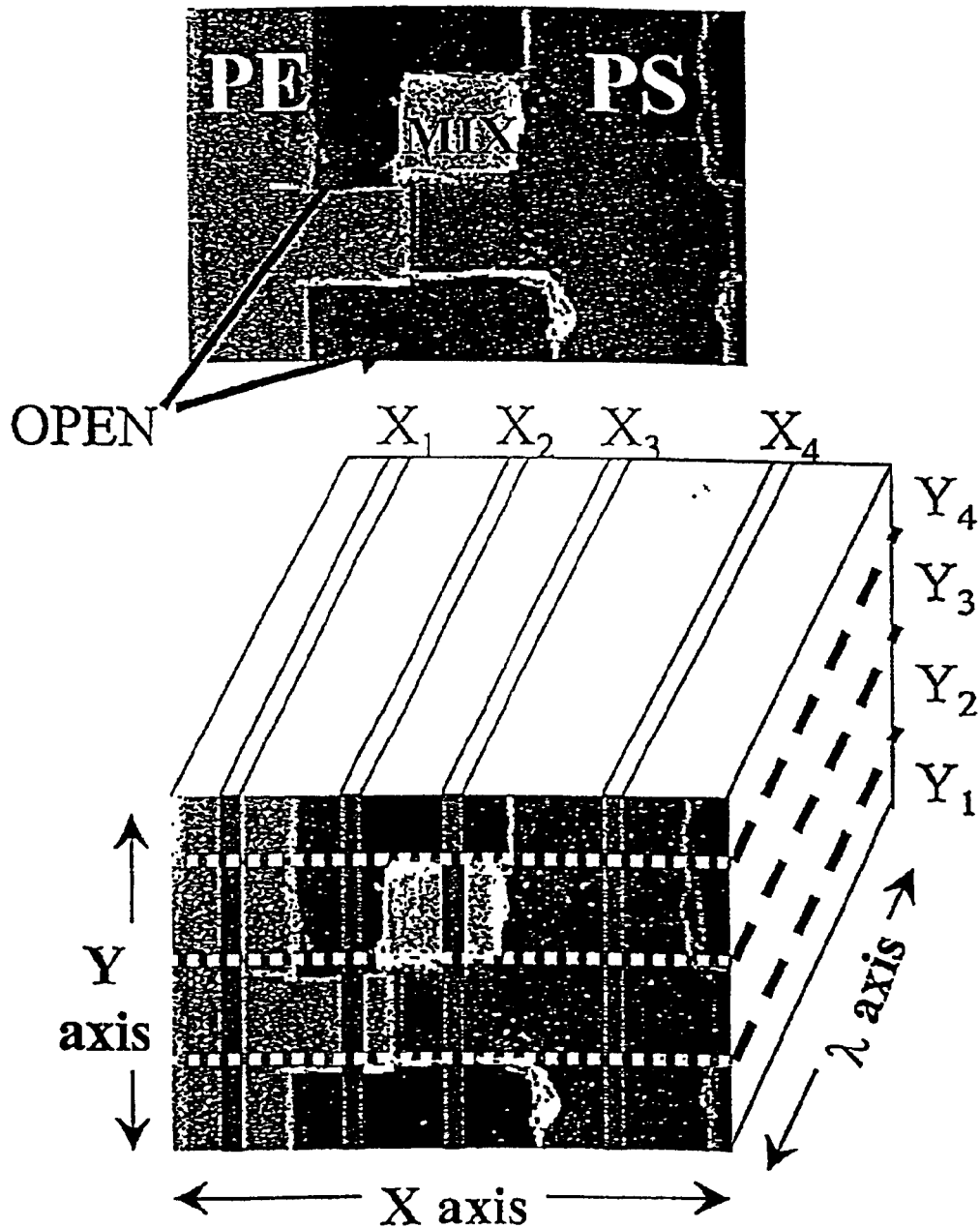
FIGS. 43–47(A–D) illustrate hyperspectrum processing in accordance with the present invention.
Figure 44:
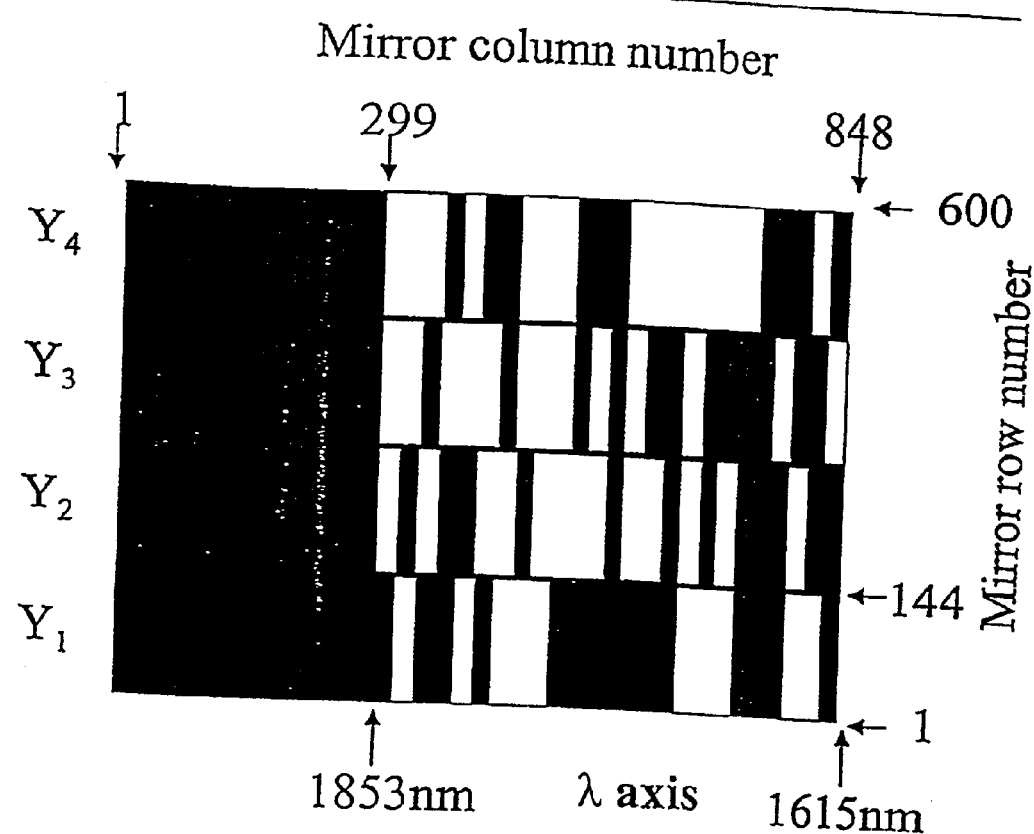
Figure 45:
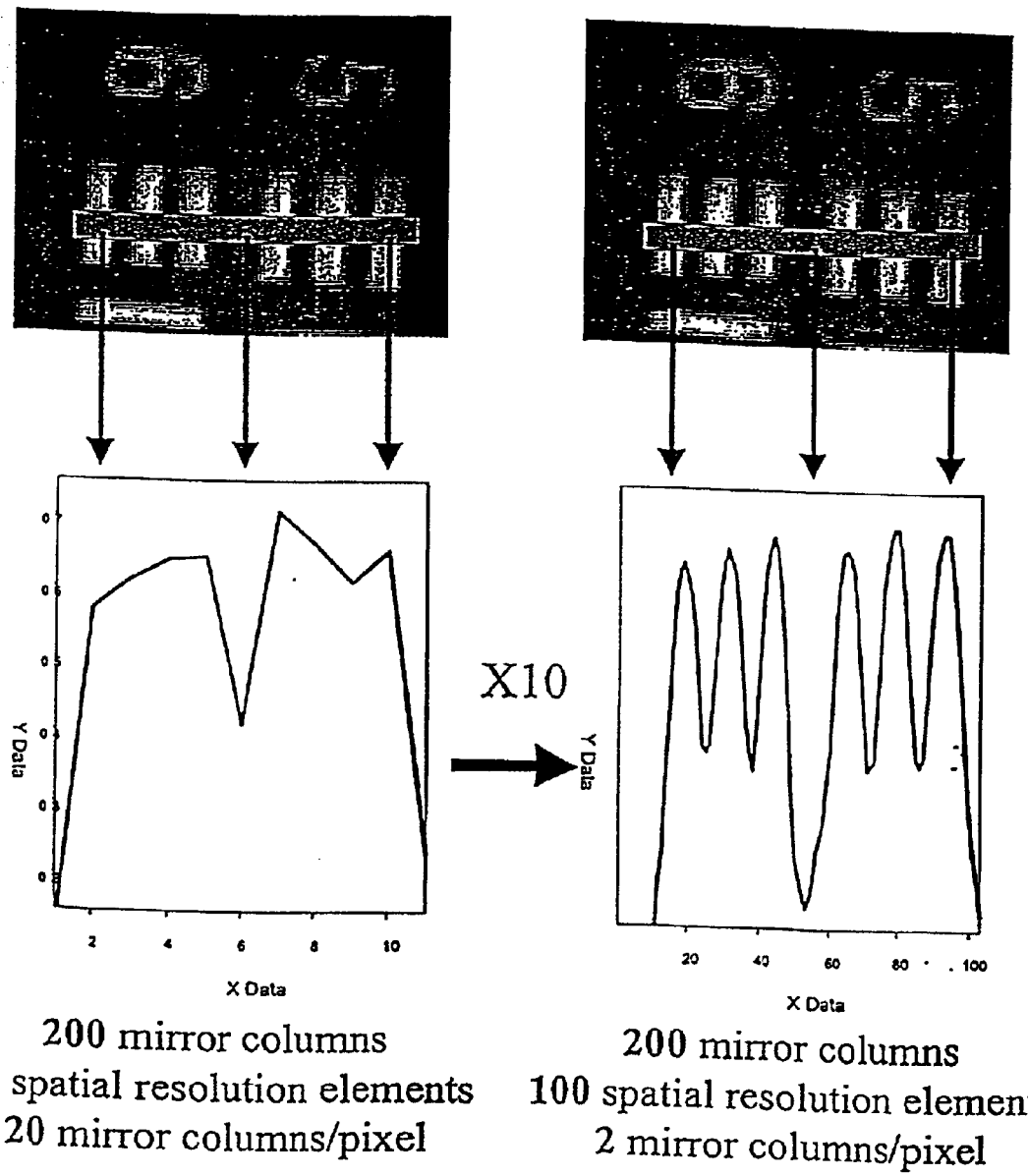
Figure 46:
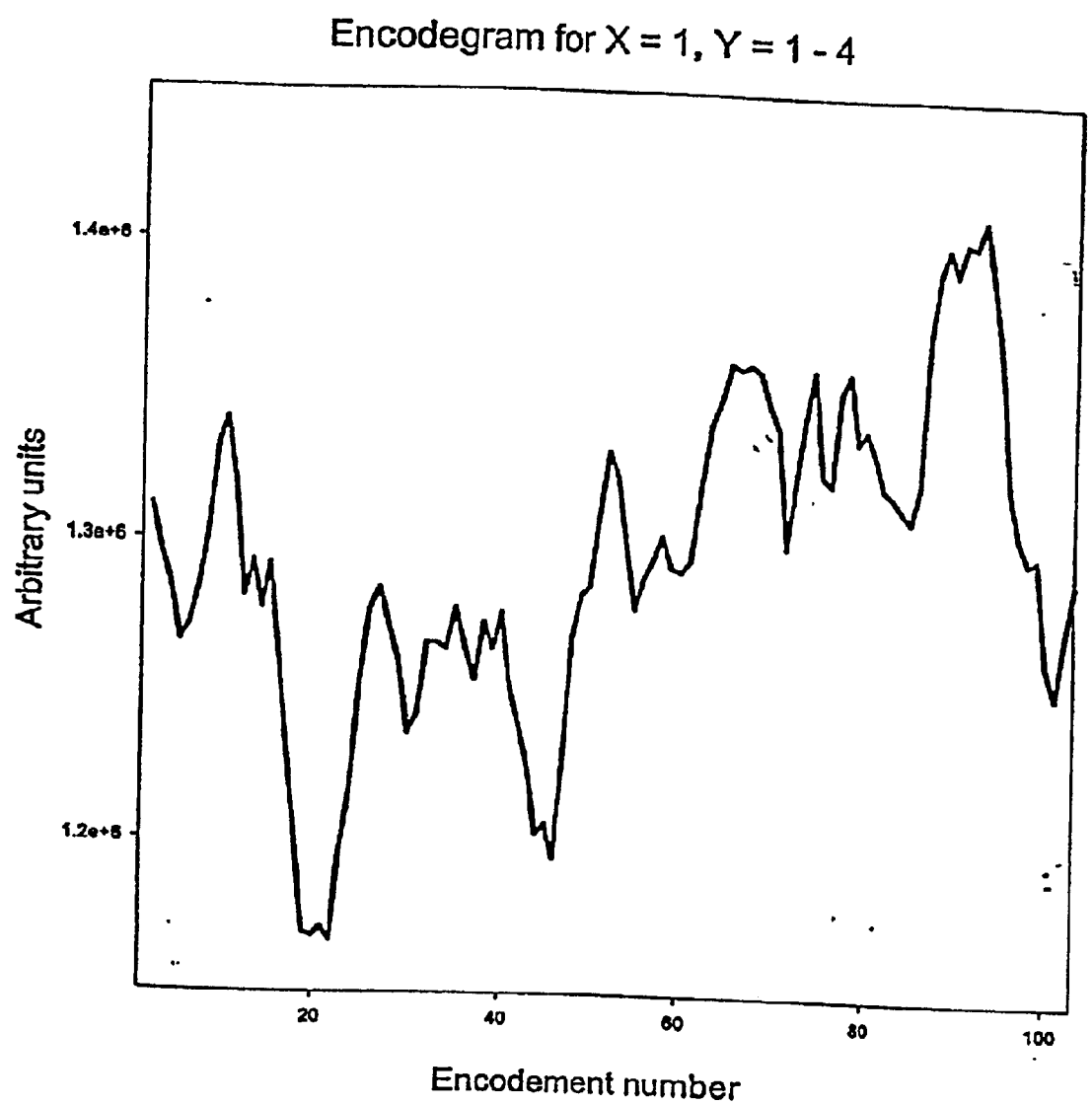
Figure 47A:
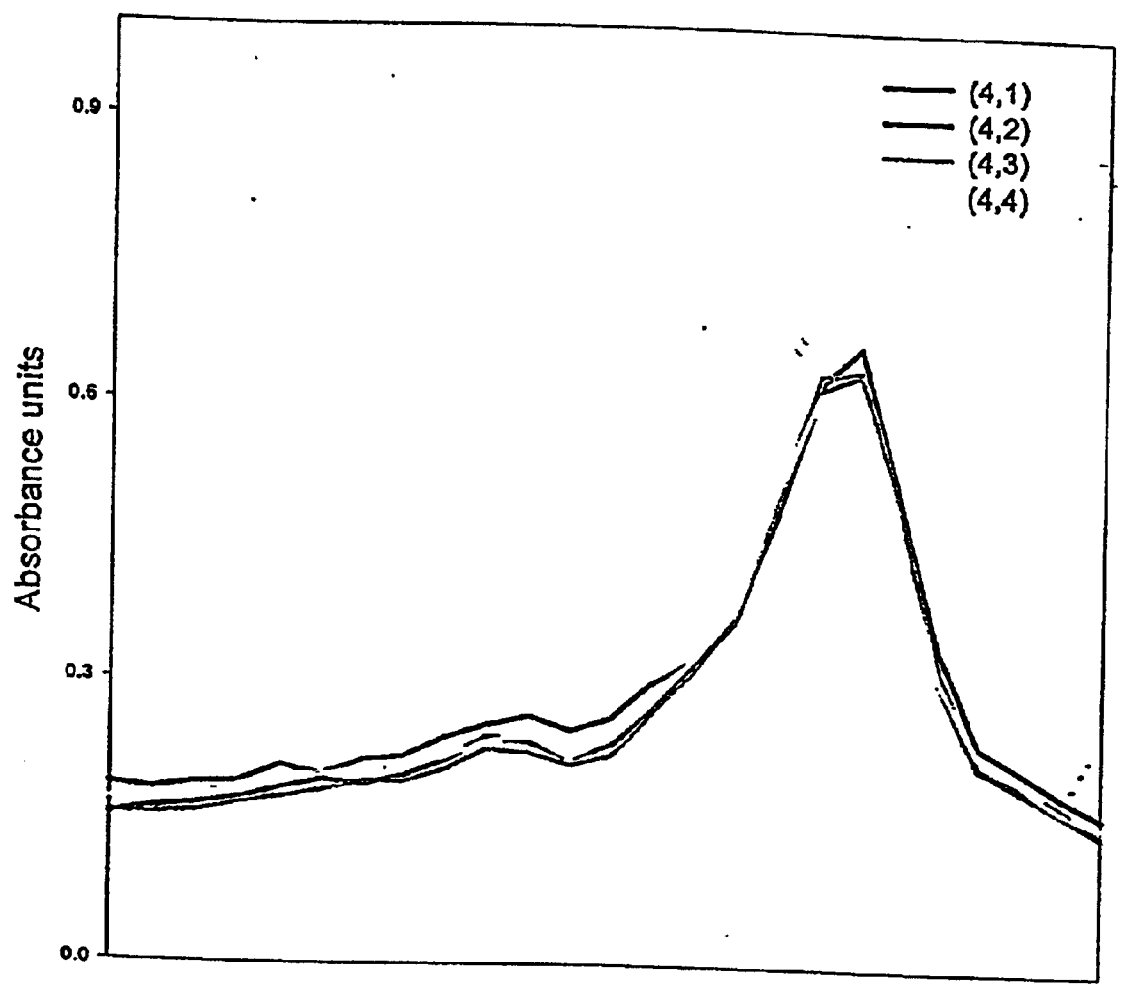
Figure 47B:
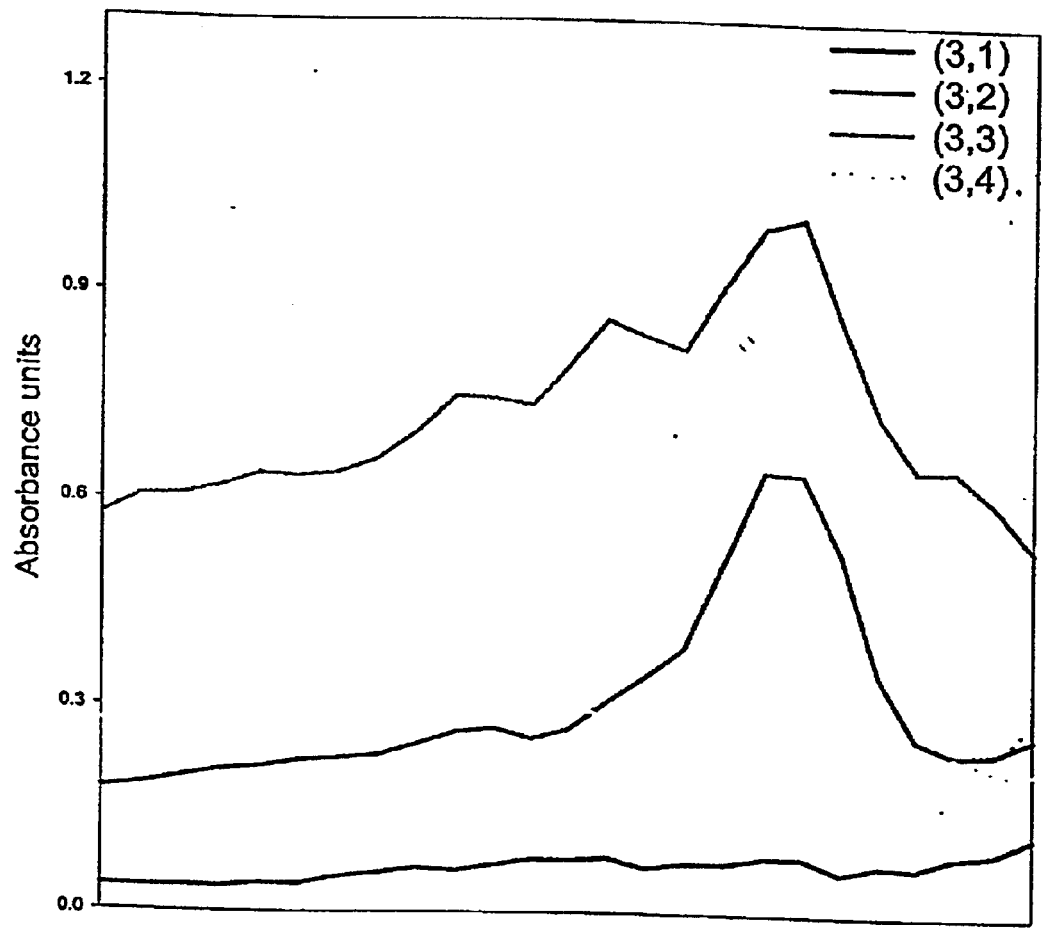
Figure 47C:
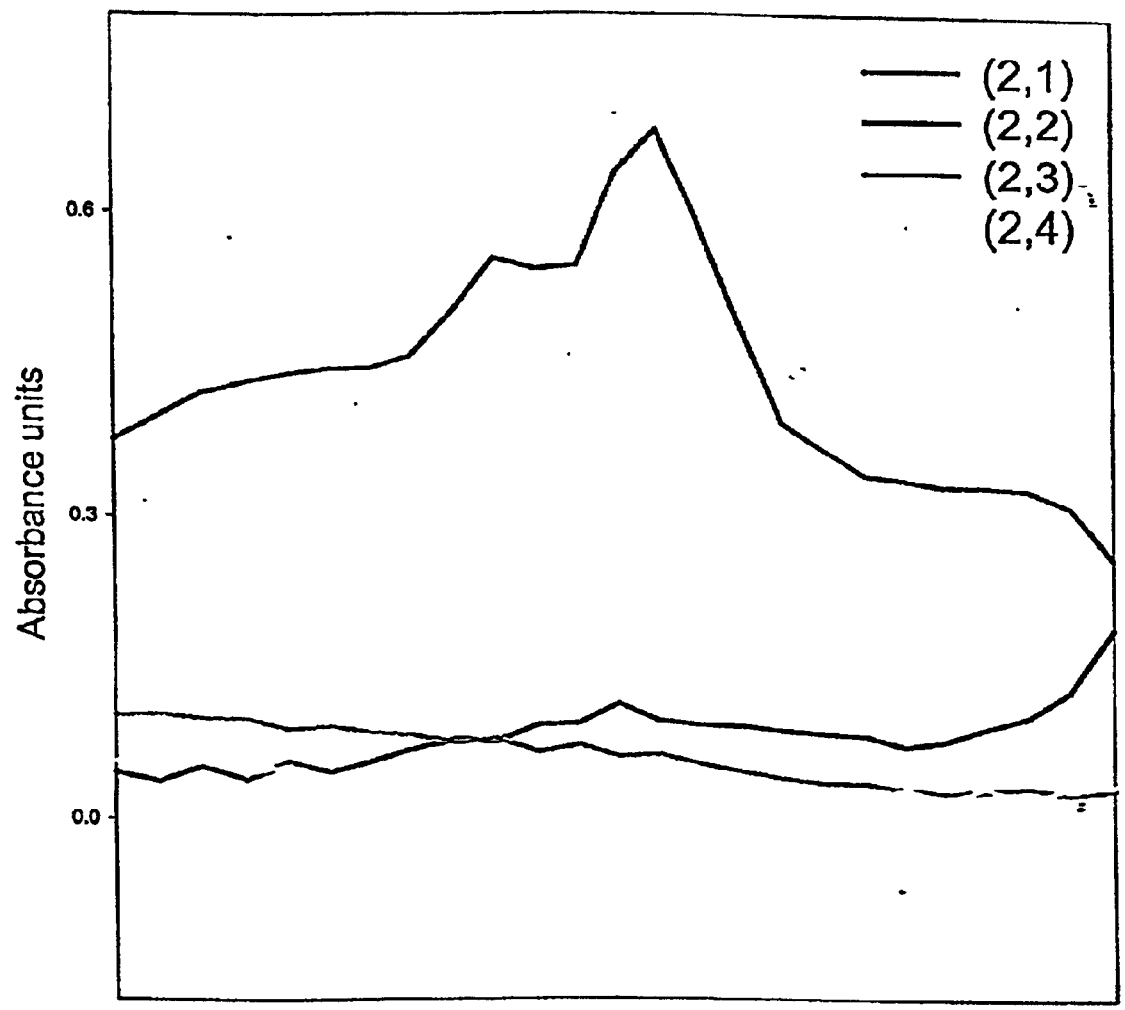
Figure 47D:
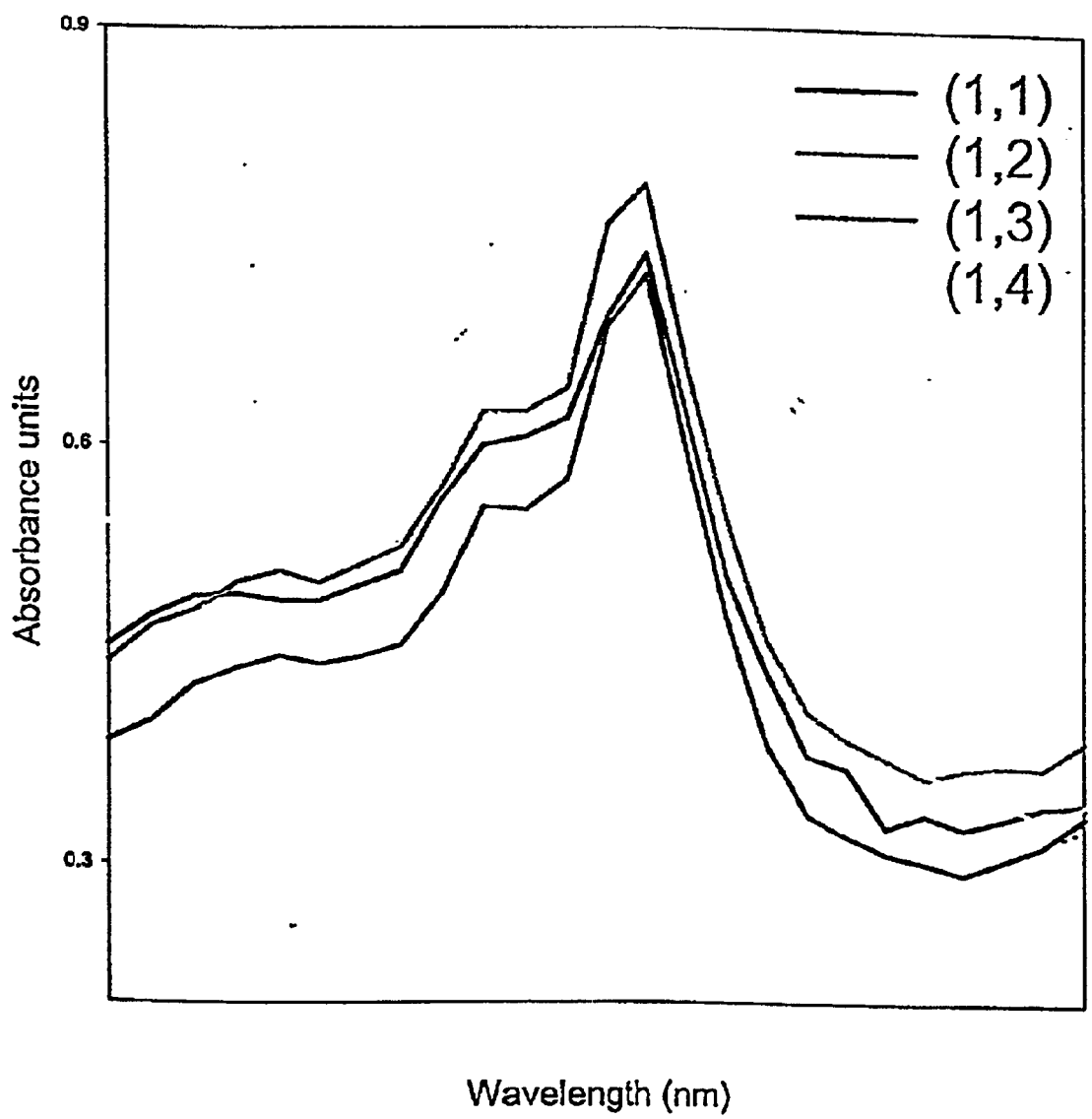

FIG. 42 illustrates the advantage of DNA-based Hadamard Spectroscopy in terms of visible improvement in the SNR of the signal for the Hadamard Encoding over the regular raster scan.

It will be appreciated that the above approach can be generalized to a method of detecting a chemical compound with known absorption lines. In particular, a simple detection mechanism for compounds with known absorption is to use an active illumination system that transmits radiation (such as light) only in areas of the absorption spectrum of the compound. The resulting reflected light will be weakest where the compound is present, resulting in dark shadows in the image (after processing away ambient light by, for example, subtracting the image before illumination). Clearly, this approach can be used to dynamically track objects in a video scene. For example, a red ball could be tracked in a video sequence having many other red objects, simply by characterizing the red signature of the ball, and tuning the illumination to it, or by processing the refined color discrimination. Clearly this capability is useful for interactive TV or video-gaming, machine vision, medical diagnostics, or other related applications. Naturally, similar processing can be applied in the infrared range (or UV) to be combined with infrared cameras to obtain a broad variety of color night vision or (heat vision), tuned to specific imaging tasks. To encode the received spatial radiation components one can use pulse code modulation (PCM), pulse width modulation (PWM), time division multiplexing (TDM) and any other modulation technique that has the property of identifying specific elements of a complex signal or image.

In accordance with the invention, in particular applications one can rapidly switch between the tuned light and its complement, arranging that the difference will display the analate of interest with the highest contrast. In addition, it is noted that the analate of interest will flicker, enabling detection by the eye. Applications of this approach in cancer detection in vivo, on operating table, can easily be foreseen.

C. Miscellaneous

A straightforward extension of the present invention is a method for initiating select chemical reactions using a tunable light source. In accordance with this aspect of the invention, the tunable light source of this invention can be tuned to the absorption profile of a compound that is activated by absorbing energy to achieve, for example, curing, drying, heating, cooking of specific compounds in a mixture and other desired results. Applications further include photodynamic therapy, such as used in jaundice treatment, chemotherapy, and others.

Yet another application is a method for conducting spectroscopy with determining the contribution of individual radiation components from multiplexed measurements of encoded spatio-spectral components. In particular a multiplicity of coded light in the UV band could be used to cause fluorescence of biological materials, the fluorescent effect can be analyzed to relate to the specific coded UV frequency allowing a multiplicity of measurements to occur in a multiplexed form. An illumination spectrum can be designed to dynamically stimulate the material to produce a detectable characteristic signature, including fluorescence effects and multiple fluorescent effects, as well a Raman and polarization effects. Shining UV light in various selected wavelengths is known to provoke characteristic fluorescence, which when spectrally analyzed can be used to discriminate between various categories of living or dead cells.

Another important application of the system and method of this invention is the use of the OSPU as a correlator or mask in an optical computation device. For example, an SLM, such as DMA can act as a spatial filter or mask placed at the focal length of a lens or set of lenses. As illustrated above, the SLM can be configured to reject specific spatial the resolution elements, so that the subsequent image has properties that are consistent with spatial filtering in Fourier space. It will be apparent that the transform of the image by optical means is spatially effected, and that the spatial resolution of images produced in this manner can be altered in a desired way. Exactly how the spatial resolution is altered will depend on the particular application and need not be considered in further detail.

Yet another area of use is performing certain signal processing functions in an analog domain. For example, spatial processing with a DMA can be achieved directly in order to acquire various combinations of spatial patterns. Thus, an array of mirrors can be arranged to have all mirrors of the center of the image point to one detector, while all the periphery may point to another. Another useful arrangement designed to detect vertical edges will raster scan a group of, for example, 2×2 mirrors pointing left combined with an adjacent group of 2×2 mirrors pointing right. This corresponds to a convolution of the image with an edge detector. The ability to design filters made out of patterns of 0,1,−1 i.e., mirror configurations, will enable the imaging device to only measure those features which are most useful for display, discrimination or identification of spatial patterns.

The design of filters can be done empirically by using the automatic best basis algorithms for discrimination, discussed above, which is achieved by collecting data for a class of objects needing detection, and processing all filters in the Walsh Hadamard Library of wavelet packets for optimal discrimination value. The offline default filters can then be upgraded online in realtime to adapt to filed conditions and local clutter and interferences.

While the foregoing has described and illustrated aspects of various embodiments of the present invention, those skilled in the art will recognize that alternative components and techniques, and/or combinations and permutations of the described components and techniques, can be substituted for, or added to, the embodiments described herein. It is intended, therefore, that the present invention not be defined by the specific embodiments described herein, but rather by the appended claims, which are intended to be construed in accordance with the well-settled principles of claim construction, including that: each claim should be given its broadest reasonable interpretation consistent with the specification; limitations should not be read from the specification or drawings into the claims; words in a claim should be given their plain, ordinary, and generic meaning, unless it is readily apparent from the specification that an unusual meaning was intended; an absence of the specific words "means for" connotes applicants' intent not to invoke 35 U.S.C. §112 (6) in construing the limitation; where the phrase "means for" precedes a data processing or manipulation "function," it is intended that the resulting means-plus-function element be construed to cover any, and all, computer implementation (s) of the recited "function"; a claim that contains more than one computer-implemented means-plus-function element should not be construed to require that each means-plus-function element must be a structurally distinct entity (such as a particular piece of hardware or block of code); rather, such claim should be construed merely to require that the overall combination of hardware/firmware/software which implements the invention must, as a whole, implement at least the function (s) called for by the claim's means-plus-function element (s).

We claim:

1. A tunable source of radiation, comprising:
   a broad-band radiation source providing a substantially continuous spectrum of radiation components within a predetermined portion of the spectrum;
   a spatial light modulator (SLM) illuminated by the broad-band radiation source and spatially modulating the broad-band radiation; and
   a wavelength dispersing device dispersing the broad-band radiation modulated by the SLM.

2. The tunable source of radiation of claim 1, wherein the SLM is an optical switch array.

3. The tunable source radiation of claim 2, wherein the SLM is a digital micro-mirror array (DMA).

4. The tunable source of radiation of claim 1, wherein the SLM encodes at least some of said series of radiation bands in a known manner.

5. The tunable source of radiation of claim 1, further comprising an exit aperture disposed to receive a selected subset of the dispersed radiation, wherein no integrating device (device for remixing the dispersed wavelengths) is interposed between the wavelength dispersing device and the exit aperture.

6. The tunable source of radiation of claims, wherein the broad-band radiation source comprises a LED.

7. The tunable source of radiation of claim 1, wherein the SLM comprises a MEMS array.

8. The tunable source of radiation of claim 1, wherein the wavelength dispersing device comprises a diffracting grating.

9. The tunable source of radiation of claim 1, wherein the wavelength dispersing device comprises a prism.

10. A device for measuring interaction of electromagnetic radiation with samples of material, comprising:
    a radiation source for irradiating at least one sample of the material with electromagnetic radiation, said source having predetermined characteristics;
    means for encoding arbitrary radiation bands from the sample with a unique code;
    processing means for processing encoded radiation bands in the analog domain;
    detector means receiving input from said processing means and providing on output an indication of the interaction between the electro-magnetic radiation from the source with the sample of material.

11. The device of claim 10, wherein the means for encoding apply an orthogonal basis of encoding functions.

12. The device of claim 10, wherein the processing means is configured to perform Hadamard processing.

13. The device of claim 10, wherein the processing means is configured to perform hyperspectral imaging.

14. The device of claim 10, wherein the detector means comprises a radiation transducer.

* * * * *